US012648953B2

(12) United States Patent
Purves et al.

(10) Patent No.: US 12,648,953 B2
(45) Date of Patent: Jun. 9, 2026

(54) COMPOSITIONS AND METHODS FOR THE TREATMENT OF INFLAMMATION IN UROLOGICAL PATHOLOGY

(71) Applicant: Duke University, Durham, NC (US)

(72) Inventors: Todd Purves, Durham, NC (US); Francis Hughes, Durham, NC (US)

(73) Assignee: Duke University, Durham, NC (US)

( * ) Notice: Subject to any disclaimer, the term of this patent is extended or adjusted under 35 U.S.C. 154(b) by 149 days.

(21) Appl. No.: 18/146,665

(22) Filed: Dec. 27, 2022

(65) Prior Publication Data

US 2023/0277559 A1 Sep. 7, 2023

Related U.S. Application Data

(62) Division of application No. 16/879,693, filed on May 20, 2020, now Pat. No. 11,559,536.

(60) Provisional application No. 62/850,015, filed on May 20, 2019.

(51) Int. Cl.
| | |
|---|---|
| *A61K 31/64* | (2006.01) |
| *A61K 45/06* | (2006.01) |
| *A61P 25/24* | (2006.01) |

(52) U.S. Cl.
CPC .............. *A61K 31/64* (2013.01); *A61K 45/06* (2013.01); *A61P 25/24* (2018.01)

(58) Field of Classification Search
CPC ................................ A61K 31/64; A61P 25/24
See application file for complete search history.

(56) References Cited

U.S. PATENT DOCUMENTS

| | | | | | |
|---|---|---|---|---|---|
| 5,698,549 A | * | 12/1997 | Steers | .................... | G01N 33/74 514/211.07 |
| 11,559,536 B2 | | 1/2023 | Purves et al. | | |

OTHER PUBLICATIONS

Hughes et al., "Inflammasomes Are Important Mediators Of Cyclophosphamide-Induced Bladder Inflammation", The Journal of Urology, vol. 191, No. 4S, Supplement, p. e80, abstract No. MP8-15 (May 2014).*

Lamkanfi M., et al., "Glyburide Inhibits the Cryopyrin/Nalp3 Inflammasome," Journal of Cell Biology, Oct. 2009, vol. 187, pp. 61-70.

Li J., et al., "Tumor Necrosis Factor Alpha Mediates Lipopolysaccharide-induced Microglial Toxicity to Developing Oligodendrocytes when Astrocytes are present," The Journal of Neuroscience, May 14, 2008, vol. 28(20), pp. 5321-5330.

Liu B., et al., "Spinal Astrocytic Activation Contributes to Mechanical Allodynia in a Rat Model of Cyclophosphamide-Induced Cystitis," Molecular Pain, Nov. 2016, vol. 12(1-12), 12 pages.

Liu D., et al., "Role of NLRP3 Inflammasome in the Pathogenesis of Cardiovascular Diseases," Basic Research in Cardiology, Dec. 2017, vol. 113(1), 14 pages.

Liu G., et al., "Diabetic Bladder Dysfunction," Chinese Medical Journal, 2014, vol. 127(7), pp. 1357-1364.

Lutolf R., et al., "NLRP3/IL-1 Mediates Denervation During Bladder Outlet Obstruction in Rats," Neurourology and Urodynamics, Mar. 2018, vol. 37(3), pp. 952-959.

Martinon F., et al., "Gout-associated Uric Acid Crystals Activate the NALP3 Inflammasome," Nature, Mar. 9, 2006, vol. 440, pp. 237-241.

McKernan C.L., et al., "Psychosocial Co-morbidities in Interstitial Cystitis/Bladder Pain syndrome (IC/BPS): A Systematic Review," Neurourology and Urodynamics, Mar. 2018, vol. 37(3), pp. 926-941.

McTigue M.D., et al., "The Life, Death, and Replacement of Oligodendrocytes in the adult CNS," Journal of Neurochemistry, Oct. 2008, vol. 107 (1-19), 19 pages.

Meijlink M.J, "Bladder pain: The Patient Perspective," Urologia, Sep. 2017, vol. 84(1), pp. 55-57.

Melone A.M., et al., "Verapamil Inhibits Ser202/Thr205 Phosphorylation of Tau by Blocking TXNIP/ROS/p38 MAPK Pathway," Pharmaceutical Research, Feb. 2018, vol. 35(2), 14 Pages.

Michaelides A., et al., "Depression, Anxiety and Acute Pain: Links and Management Challenges," Postgraduate Medicine, Sep. 2019, vol. 131(7), pp. 438-444.

Michels M., et al., "The Role of Microglia Activation in the Development of Sepsis-induced Long-term Cognitive Impairment," Brain, Behaviour Immunity, Jan. 2015, vol. 43, pp. 54-59.

Miller H.A., et al., "Inflammation and its Discontents: The Role of Cytokines in the Pathophysiology of Major Depression," Biological Psychiatry, May 2009, vol. 65(9), pp. 732-741.

Miller H.A., et al., "The Role of Inflammation in Depression: From Evolutionary Imperative to Modern Treatment Target," Nature Reviews, Immunology, Jan. 2016, vol. 16(1) , pp. 22-34.

Milsom I., et al., "Effect of Bothersome Overactive Bladder Symptoms on Health-related Quality of Life, Anxiety, Depression, and Treatment Seeking in the United States: results from EpiLUTS," Urology, Jul. 2012, vol. 80, pp. 90-96.

Minutoli L., et al., "ROS-Mediated NLRP3 Inflammasome Activation in Brain, Heart, Kidney, and Testis Ischemia/Reperfusion Injury," Oxidative Medicine and Cellular Longevity, 2016, 15 pages.

Mokhtari V., et al., "A Review on Various Uses of N-Acetyl Cysteine," Cell Journal, 2017, vol. 19(1), pp. 11-17.

Muere A., et al., "Depression and Coping Behaviors are Key Factors in Understanding Pain in Interstitial Cystitis/Bladder Pain Syndrome," Oct. 2018, Pain Management Nursing, vol. 19(5), pp. 497-505.

Noto C., et al., "Targeting the Inflammatory Pathway as a Therapeutic Tool for Major Depression," Neuroimmunomodulation, 2014, vol. 21, pp. 131-139.

Panigrahy R., et al., "Diabetic Uropathy and Bladder Dysfunctions," Diabetes Metabolic Syndrome, 2017, pp. 81-82.

Patel N.M., et al., "Inflammasome Priming in Sterile Inflammatory Disease," Trends in Molecular Medicine, Feb. 2017, vol. 23(2), pp. 165-180.

(Continued)

*Primary Examiner* — Kevin E Weddington

(74) *Attorney, Agent, or Firm* — Polsinelli PC

(57) ABSTRACT

The present disclosure provides compositions and methods for the treatment of inflammation in urological pathologies.

10 Claims, 36 Drawing Sheets

Specification includes a Sequence Listing.

(56) References Cited

OTHER PUBLICATIONS

Petrilli V., et al., "The Inflammasome: A Danger Sensing Complex Triggering Innate Immunity," Current Opinion in Immunology, Dec. 2007, vol. 19(6), pp. 615-622.

Purves J.T., et al., "Inflammasomes in the Urinary Tract: A Disease-based Review," Oct. 2016, American Journal of Physiology, Renal Physiology, vol. 311(4), pp. F635-F662.

Renard J., et al., "Recurrent Lower Urinary Tract Infections Have a Detrimental Effect on Patient Quality of Life: A Prospective, Observational Study," Infectious Disease and Theraphy, Dec. 2014, vol. 4(1), pp. 125-135.

Rheinheimer J., et al., "Current Role of the NLRP3 Inflammasome on Obesity and Insulin Resistance: A Systematic Review," Metabolism: Clinical and experimental, Sep. 2017, vol. 74, pp. 1-9.

Roberts W.M., et al., "Ureteral Stricture Formation After Removal of Impacted Calculi," Journal of Urology, Mar. 1998, vol. 159 (3), pp. 723-726.

Sarica K., et al., "Effect of Verapamil on Urinary Stone-forming Risk Factors," Urological Research, Feb. 2007, vol. 35(1), pp. 23-27.

Sarma V.A., et al., "Risk Factors for Urinary Incontinence Among Women with Type 1 Diabetes: Findings from the Epidemiology of Diabetes Interventions and Complications Study," Urology, Jun. 2009, vol. 73(6), pp. 1203-1209.

Savage D.C., et al., "NLRP3-Inflammasome Activating DAMPs Stimulate an Inflammatory Response in Glia in the Absence of Priming Which Contributes to Brain Inflammation After Injury," Frontiers in Immunology, Sep. 2012, vol. 3, Article 288, 11 Pages.

Sayana P., et al., "A Systematic Review of Evidence for the Role of Inflammatory Biomarkers in Bipolar Patients," Journal of Psychiatric Research, Sep. 2017, vol. 92, pp. 160-182.

Schwarcz R., et al., "Manipulation of Brain Kynurenines: Glial Targets, Neuronal Effects, and Clinical Opportunities," Journal of Pharmacology and Experimental Therapeutics, Oct. 2002, vol. 303(1), pp. 1-10.

Selvin E., et al., "Trends in Prevalence and Control of Diabetes in the United States 1988-1994 and 1999-2010," Annals of Internal Medicine, Apr. 2014, vol. 160(8), pp. 517-525.

Sepehri Z., et al., "Inflammasomes and Type 2 Diabetes: An Updated Systematic Review," Immunology Letters, Dec. 2017, vol. 192, pp. 97-103.

Shin J.J., et al., "Damage-associated Molecular Patterns and Their Pathological Relevance in Diabetes Mellitus," Ageing Research Review, Nov. 2015, vol. 24, pp. 66-76.

Silva T.M., et al., "Anxiogenic-like Effect of Acute and Chronic Fluoxetine on Rats Tested on the Elevated Plus-maze," Brazilian Journal of Medical and Biological Research, Mar. 1999, 32(3), pp. 333-339.

Stokum A.J., et al., "Glibenclamide Pretreatment Protects Against Chronic Memory Dysfunction and Glial Activation in Rat Cranial Blast Traumatic Brain Injury," Behavioural Brain Research, 2017, pp. 43-53.

Tanik N., et al., "Association Between Overactive Bladder and Polyneuropathy in Diabetic Patients," International Neurourology Journal, Sep. 2016, vol. 20(3), pp. 232-239.

Taylor E.S., "Mechanisms Linking Early Life Stress to Adult Health Outcomes," PNAS, May 11, 2010, vol. 107(19), pp. 8507-8512.

Teixeira L.A., et al., "Immunology of Psychiatric Disorders," Neuroimmunomodulation, Feb. 2014, vol. 21(71), 1 page.

Thompson J.R., et al., "PGP 9.5—a New Marker for Vertebrate Neurons and Neuroendocrine Cells, " Brain Research, Nov. 1983, vol. 278, pp. 224-228.

Tzeng N., et al., "Risk of Psychiatric Disorders in Overactive Bladder Syndrome: a Nationwide Cohort Study in Taiwan," Journal of Investigative Medicine, Feb. 2019, vol. 67(2), pp. 312-318.

Wu P., et al., "Urinary Microbiome and Psychological Factors in Women with Overactive Bladder," Frontiers in Cellular and Infection Microbiology, Nov. 2017, vol. 7 (488), 11 pages.

Xu G., et al., "Preventing Beta-cellloss and Diabetes with Calcium Channel Blockers," Diabetes, Apr. 2012, vol. 61(4), pp. 848-856.

Xu L., et al., "Verapamil Attenuated Prediabetic Neuropathy in High-Fat Diet-Fed Mice through Inhibiting TXNIP-Mediated Apoptosis and Inflammation," Oxidation Medicine and Cellular Longetivity, Jan. 2019, Article ID 1896041, 14 pages.

Abais M.J., et al., "Nod-like Receptor Protein 3 (NLRP3) Inflammasome Activation and Podocyte Injury Via Thioredoxin-Interacting Protein (TXNIP) During Hyperhomocysteinemia," Journal of Biological Chemistry, Sep. 26, 2014, vol. 289(39), pp. 27159-27168.

Al-Gayyar M.M., et al., "Thioredoxin Interacting Protein is a Novel Mediator of Retinal Inflammation and Neurotoxicity," British Journal of Pharmacalogy, Sep. 2011, vol. 164(1), pp. 170-180.

Ali A.S., et al., "Comparision of Uroprotective Activity of Reduced Glutathione with Mesna in Ifosfamide Induced Hemorrhagic Cystitis in Rats," Indian Journal of Pharmacology, 2014, vol. 46(1), pp. 105-108.

Belayev L., et al., "Quantitative Evaluation of Blood-brain Barrier Permeability following Middle Cerebral Artery Occlusion in Rats," Brain Research, Nov. 11, 1996, vol. 739(1-2), pp. 88-96.

Berry H.S., et al., "Prevalence of Symptoms of Bladder Pain Syndrome/interstitial Cystitis Among Adult Females in the United States," Journal of Urology, Aug. 2011, vol. 186(2), pp. 540-544 . . . .

Borland M.L., et al., "Voltammetric Study of the Control of Striatal Dopamine Release by Glutamate," Oct. 2004, Journal of Neurochemistry, vol. 91, pp. 220-229.

Buntinx M., et al., "Cytokine-induced Cell Death in Human Oligodendroglial Cell Lines: I. Synergistic Effects of IFN-gamma and TNF-alpha on Apoptosis," Journal of Neuroscience Research, Jun. 15, 2004, vol. 76, pp. 834-845.

Camoillo-Gimenez L., et al., "Inflammatory Potential of Four Different Phases of Calcium Pyrophosphate Relies on NF-kappaB Activation and MAPK Pathways," Frontiers in Immunology, Oct. 2018, vol. 9, Article 2248, 15 pages.

Carless., et al., "The Selection and Use of Essential Medicines," World Health Organization Technical Report Series, Oct. 2007, 188 pages.

Chen J., et al., "Diabetes Induces and Calcium Channel Blockers Prevent Cardiac Expression of Proapoptotic Thioredoxin-interacting Protein," American Journal of Physiology, Endocrinology and Metabolism, May 2009, vol. 296 (5), pp. E1133-E1139.

Colpo D.G., et al., "Immune-based Strategies for Mood Disorders: Facts and Challenges," Expert Review of Neurotherapeutics, Feb. 2018, vol. 18(2), pp. 139-152.

Coyne S.K., et al., "The Burden of Lower Urinary Tract Symptoms: Evaluating the Effect of LUTS on Health-related Quality of Life, Anxiety and Depression: EpiLUTS," BJU International, Apr. 2009, vol. 103(3), pp. 4-11.

Daneshgari F., et al., "Diabetic uropathy," Seminar in Nephrology, Mar. 2006, vol. 26(2), pp. 182-185.

Dantzer R., et al., "From Inflammation to Sickness and Depression: When the Immune System Subjugates the Brain," Nature Review Neuroscience, Jan. 2008, vol. 9(1), pp. 46-56.

Daulatzai A.M., "Chronic Functional Bowel Syndrome Enhances Gut-brain Axis Dysfunction, Neuroinflammation, Cognitive Impairment, and Vulnerability to Dementia," Neurochemical Research, Apr. 2014, vol. 39(4), pp. 624-644.

D'Mello C., et al., "Cerebral Microglia Recruit Monocytes into the Brain in Response to Tumor Necrosis Factoralpha Signaling During Peripheral Organ Inflammation," Journal of Neuroscience, Feb. 18, 2009, vol. 29(7), pp. 2089-2102.

Dong H., et al., "Prevention Strategies for Ureteral Stricture Following Ureteroscopic Lithotripsy," Asian Journal of Uralogy, Apr. 2018, vol. 5(2), pp. 94-100.

Dunphy C., et al., "Relationship Between Depression and Lower Urinary Tract Symptoms Secondary to Benign Prostatic Hyperplasia," Reviews in Urology, 2015, vol. 17(2), pp. 51-57.

Fowler J.C., et al., "Bladder Afferents and their Role in the Overactive Bladder," Urology, May 2002, vol. 59(1), pp. 37-42.

Fujigaki H., et al., "The Signal Transducer and Activator of Transcription 1alpha and Interferon Regulatory Factor 1 are not Essen-

(56) References Cited

OTHER PUBLICATIONS tial for the Induction of Indoleamine 2, 3-dioxygenase by Lipopolysaccharide: Involvement of p38 Mitogen-activated Protein Kinase and Nuclear Factor-KappaB Pathways, and Synergistic Effect of Several Proinflammatory Cytokines," Journal of Biochemistry, Apr. 2006, vol. 139(4), pp. 655-662.

Genuth S., "Insights from the Diabetes Control and Complications Trial/epidemiology of Diabetes Interventions and Complications Study on the Use of Intensive Glycemic Treatment to Reduce the Risk of Complications of Type 1 Diabetes," Endocrine Practice, Jan./Feb. 2006, vol. 12(1), pp. 34-41.

Giannantoni A., et al., "Abstract MP27-11-Overactive Bladder, Urinary Incontinence And Depression," Journal of Urology, May 19, 2018, vol. 199(4), e350-e351.

Golabek T., et al., "Lower Urinary Tract Symptoms, Nocturia and Overactive Bladder in Patients with Depression and Anxiety," Psychiatria Polska, 2016, vol. 50(2), pp. 417-430.

Gomez S.C., et al., "Bladder Dysfunction in Patients with Diabetes," Current Urology Reports, Dec. 2011, vol. 12(6), pp. 419-426.

Goshen I., et al., "A Dual Role for Interleukin-1 in Hippocampal-dependent Memory Process," Psychoneuroendocrinology, 2007, vol. 32, pp. 1106-1115.

Goshen I., et al., "Brain Interleukin-1 Mediates Chronic Stress-induced Depression in Mice Via Adrenocortical Activation and Hippocampal Neurogenesis Suppression," Molecular Psychiatry, Jul. 2008, vol. 13(7), pp. 717-728.

Gotoh D., et al., "Tadalafil, a Phosphodiesterase Type 5 Inhibitor, Improves Bladder Blood Supply and Restores the Initial Phase of Lower Urinary Tract Dysfunction in Diabetic Rats," Neurourology and Urodynamics, Feb. 2018, vol. 37(2), pp. 666-672.

Guan N.N., et al., "Receptors Involved in the Modulation of Guinea Pig Urinary Bladder Motility by Prostaglandin D2," British Journal of pharmacology, Aug. 2015, vol. 172(16), pp. 4024-4037.

Haldar S., et al., "Inflammation and Pyroptosis Mediate Muscle Expansion in an Interleukin-1(IL-1)-dependent Manner," The Journal of Biological Chemistry, Mar. 6, 2015, vol. 290(10), pp. 6574-6583.

Hamasaki Y.M., et al., "Animal Models of Neuroinflammation Secondary to Acute Insults Originated Outside the Brain," Journal of Neuroscience, Mar. 2018, vol. 96(3), pp. 371-378.

Hameed I., et al., "Type 2 Diabetes Mellitus: From a Metabolic Disorder to an Inflammatory Condition," World Journal of Diabetes, May 15, 2015, vol. 6(4), pp. 598-612.

Hamilton C., et al., "Immunity to Uropathogens: The Emerging Roles of Inflammasomes," Nature Reviews Urology, May 2017, vol. 14 (5), pp. 284-295.

Haroon E., et al., "Inflammation, Glutamate, and Glia: A Trio of Trouble in Mood Disorders," Neuropsychopharmacology, 2017, vol. 42, pp. 193-215.

Hepner A.K., et al., "Suicidal Ideation Among Patients with Bladder Pain Syndrome/interstitial Cystitis," Aug. 2012, vol. 80(2), pp. 280-285.

Hsieh Y., et al., "Intestinal Ischemia-reperfusion Injury Leads to Inflammatory Changes in the Brain," Oct. 2011, vol. 36(4), pp. 424-430.

Hughes M.F. Jr., et al., "Bladder Decompensation and Reduction in Nerve Density in a Rat Model of Chronic Bladder Outlet Obstruction are Attenuated with the NLRP3 Inhibitor Glyburide," American Journal of Physiology Renal Physiology, Jan. 1, 2019, vol. 316, pp. F113-F120.

Hughes M.F. Jr., et al., "Inflammasomes are Important Mediators of Cyclophosphamide-induced Bladder Inflammation," American journal of physiology Renal physiology, Feb. 2014, vol. 306(3), F299-308.

Hughes M.F. Jr., et al., "The NLPR3 Inflammasome Mediates Inflammation Produced by Bladder Outlet Obstruction," Journal of Urology, May 2016, vol. 195(5), pp. 1598-1605.

Hughes M.F. Jr., et al., "The Potential Repertoire of the Innate Immune System in the Bladder: Expression of Pattern Recognition Receptors in the Rat Bladder and a Rat Urothelial Cell Line (MYP3 cells)," International Urology and Nephrology, Dec. 2015, vol. 47(12), pp. 1953-1964.

Hughes M.F. Jr., et al., "NLRP3 Promotes Diabetic Bladder Dysfunction and Changes in Symptom-Specific Bladder Innervation," Diabetes, Feb. 2019, vol. 68(2), pp. 430-440.

Hughes M.F.Jr., et al., "The NACHT, LRR and PYD Domains-Containing Protein 3 (NLRP3) Inflammasome Mediates Inflammation and Voiding Dysfunction in a Lipopolysaccharide-Induced Rat Model of Cystitis," Journal Clinical & Cellular Immunology, Feb. 2016, vol. 7(1), 15 Pages.

Iguchi M., et al., "Effect of Verapamil on Urinary Calcium and Oxalate Excretion in Renal Stone Formers," Hinyokika Kiyo, May 1993, vol. 39(5), pp. 425-431.

Inouye M.B., et al., "The Emerging Role of Inflammasomes as Central Mediators in Inflammatory Bladder Pathology," Current Urology, Feb. 2018, vol. 11(2), pp. 57-72.

Joshi S., et al., "Wang Activation of the NLRP3 Inflammasome in Association with Calcium Oxalate Crystal Induced Reactive Oxygen Species in Kidneys," Journal of Uranology, May 2015, vol. 193(5), pp. 1684-1691.

Kaplan A.S., et al., "Diabetic Cystopathy," Journal of Diabet Complications, 1988, pp. 133-139.

Kim H.S., et al., "Diallyl Disulfide Prevents Cyclophosphamide-Induced Hemorrhagic Cystitis in Rats through the Inhibition of Oxidative Damage, MAPKs, and NF-KB Pathways," Biomolecule Therapautics, 2015, vol. 23(2), pp. 180-188.

Kloskowski T., et al., "How to Isolate Urothelial Cells. Comparison of Four Different Methods and Literature Review," Human Cell, Apr. 2014, vol. 27(2), pp. 85-93.

Koo W.J., et al., "IL-1B is an Essential Mediator of the Anti Neurogenic and an Hedonic Effects of Stress," Proceedings of the National Academy of Sciences of the United States of America, Jan. 15, 2008, vol. 105(2), pp. 751-756.

Lahmann C. et al., "Systemic Administration of Glibenclamide Fails to Achieve Therapeutic Levels in the Brain and Cerebrospinal Fluid of Rodents," Jul. 30, 2015, PLoS One, vol. 10(7), e0134476 (18 Pages).

Lai H., et al., "Correlation Between Psychological Stress Levels and the Severity of Overactive Bladder Symptoms," BMC Urology, Mar. 2015, vol. 15, 7 pages.

* cited by examiner

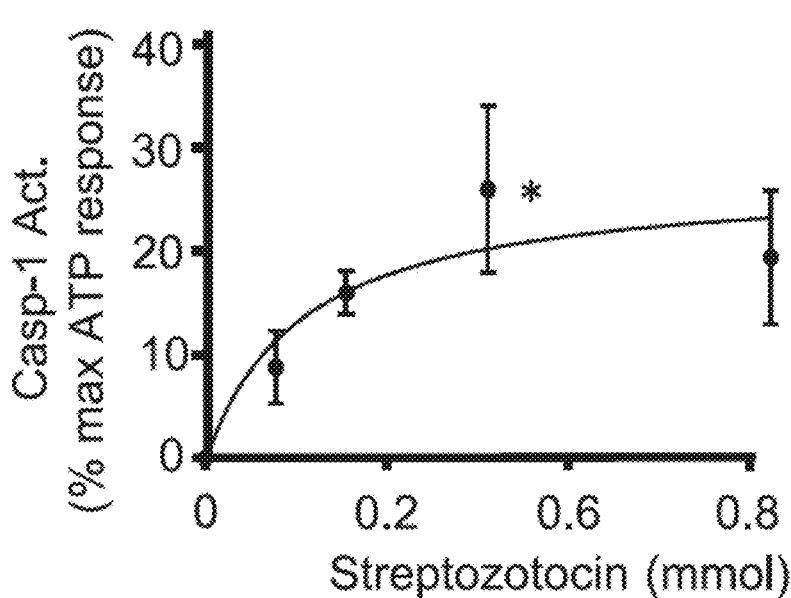
FIG. 1C
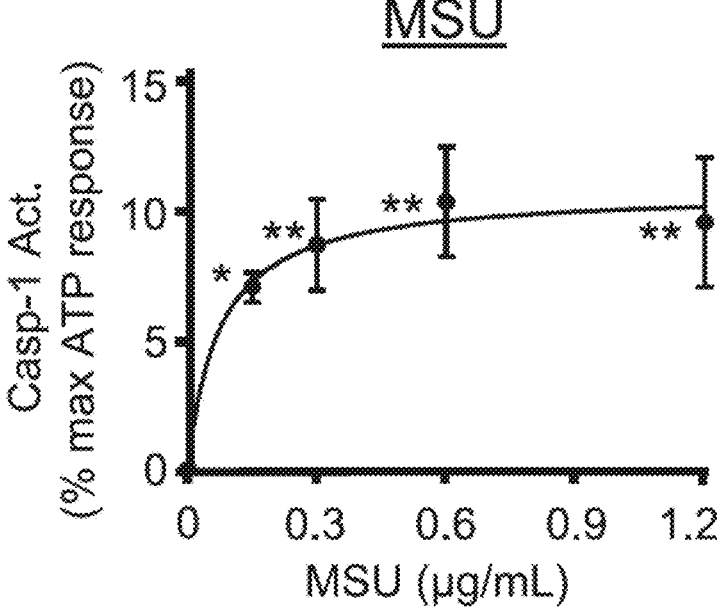
FIG. 1D

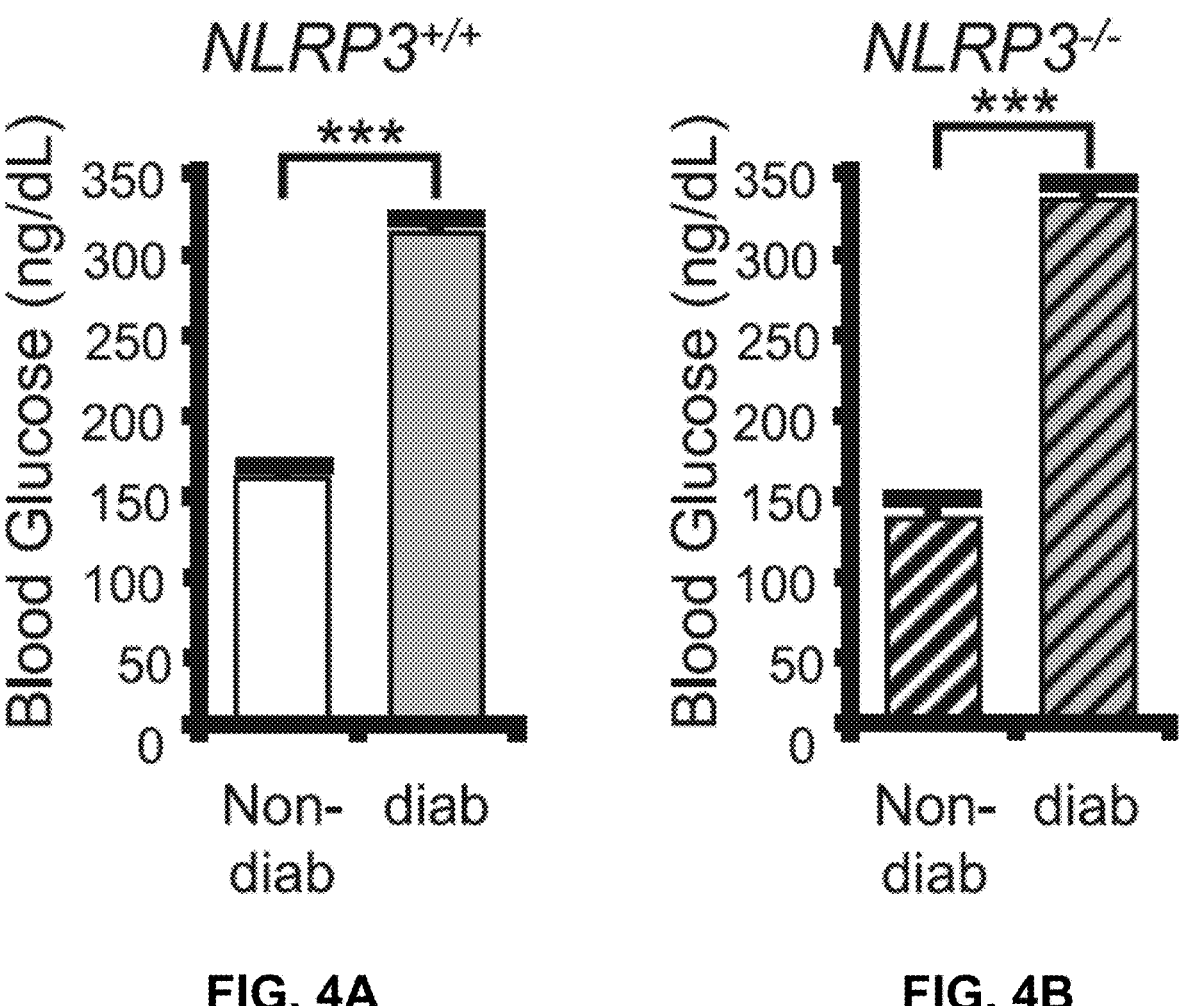
FIG. 4A                    FIG. 4B

Void Volume
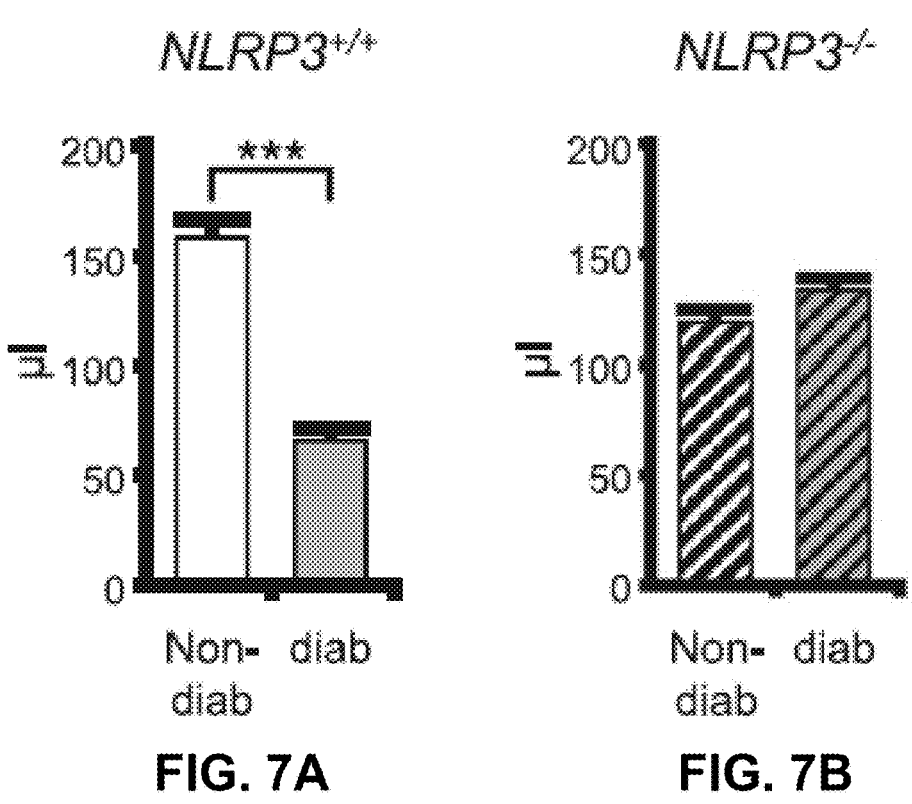
FIG. 7A
FIG. 7B
Frequency
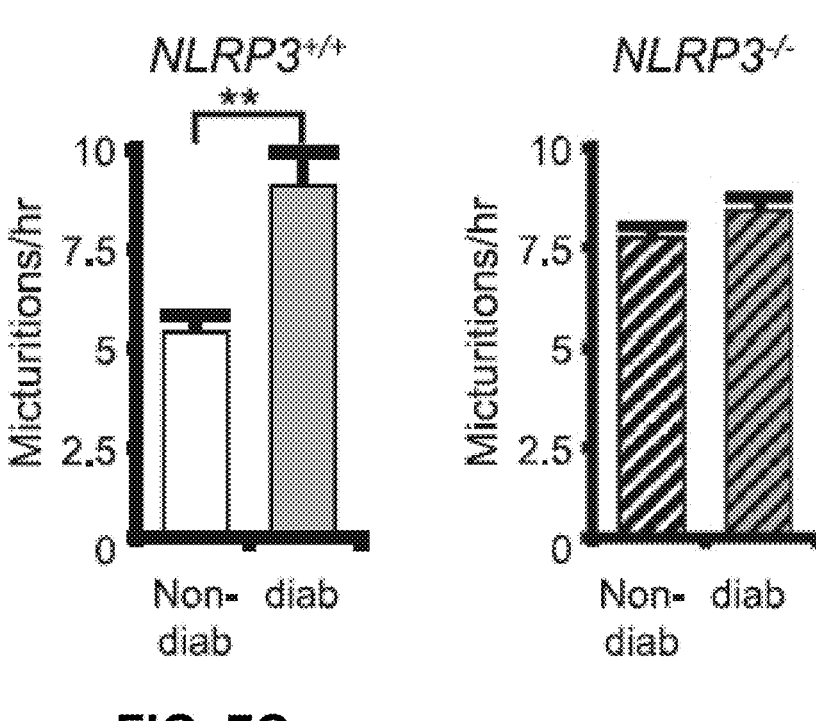
FIG. 7C
FIG. 7D

PVR
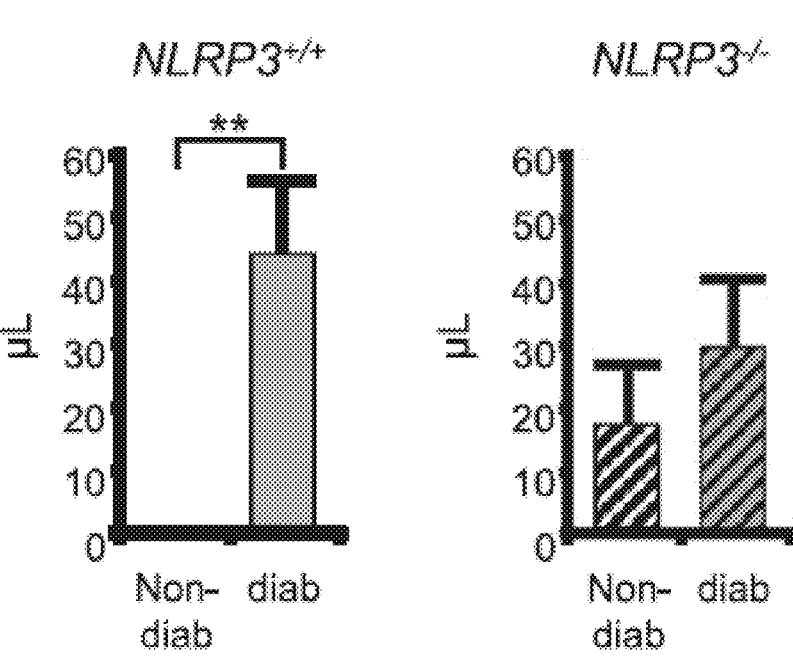
FIG. 7E
FIG. 7F
Voiding efficiency
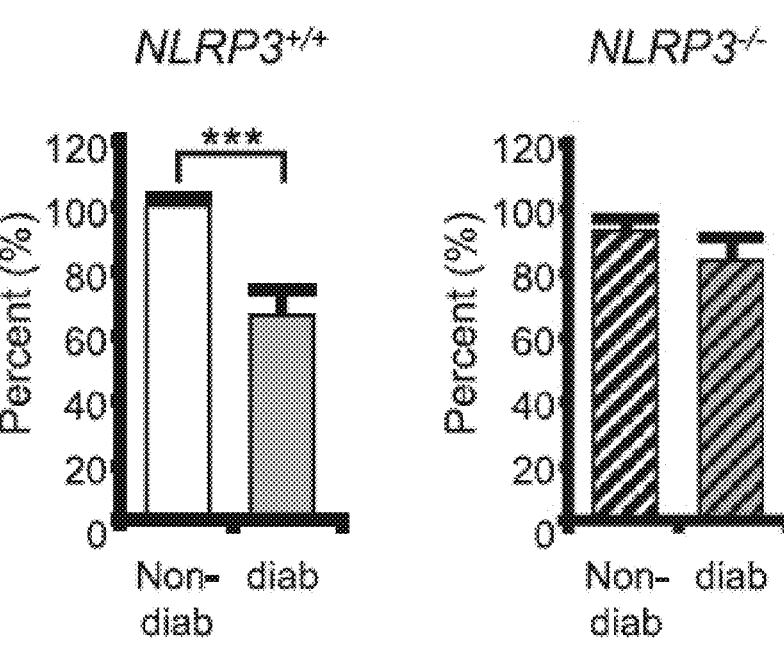
FIG. 7G
FIG. 7H

Nerve number in bladder wall

Bladder wall size

C-fiber number in urothelium

Urothelium size

* P<0.05

CPPD + NAC

MSU + NAC

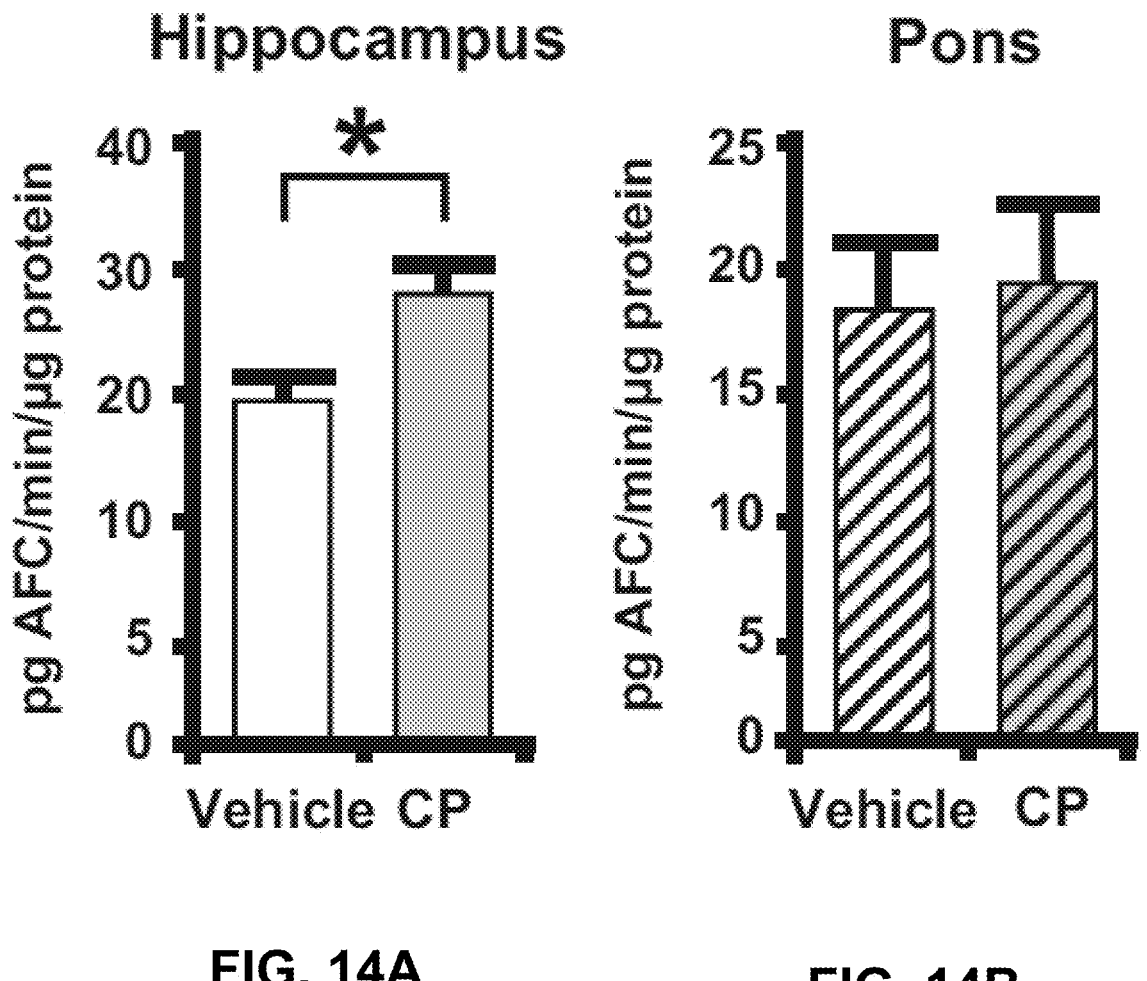
FIG. 14A          FIG. 14B

IL-1β expression

IL-18 expression

NLRP3 expression

ASC expression

Bladder Weight

Inflammation in Hippo

SEQUENCE LISTING

```
Sequence total quantity: 10
SEQ ID NO: 1             moltype = DNA  length = 23
FEATURE                  Location/Qualifiers
misc_feature             1..23
                         note = Synthetic oligonucleotide
source                   1..23
                         mol_type = other DNA
                         organism = synthetic construct
SEQUENCE: 1
caccttcttt tccttcatct ttg                                         23

SEQ ID NO: 2             moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 2
tcgttgcttg tctctccttg                                             20

SEQ ID NO: 3             moltype = DNA  length = 22
FEATURE                  Location/Qualifiers
misc_feature             1..22
                         note = Synthetic oligonucleotide
source                   1..22
                         mol_type = other DNA
                         organism = synthetic construct
SEQUENCE: 3
aggctcttgt gtcaacttca aa                                          22

SEQ ID NO: 4             moltype = DNA  length = 20
FEATURE                  Location/Qualifiers
misc_feature             1..20
                         note = Synthetic oligonucleotide
source                   1..20
                         mol_type = other DNA
                         organism = synthetic construct
SEQUENCE: 4
agtctggtct gggattcgtt                                             20

SEQ ID NO: 5             moltype = DNA  length = 21
```

```
FEATURE              Location/Qualifiers
misc_feature         1..21
                     note = Synthetic oligonucleotide
source               1..21
                     mol_type = other DNA
                     organism = synthetic construct
SEQUENCE: 5
gaagattacc cacccgagaa a                                          21

SEQ ID NO: 6         moltype = DNA  length = 20
FEATURE              Location/Qualifiers
misc_feature         1..20
                     note = Synthetic oligonucleotide
source               1..20
                     mol_type = other DNA
                     organism = synthetic construct
SEQUENCE: 6
ccagcaaacc tatccactcc                                            20

SEQ ID NO: 7         moltype = DNA  length = 20
FEATURE              Location/Qualifiers
misc_feature         1..20
                     note = Synthetic oligonucleotide
source               1..20
                     mol_type = other DNA
                     organism = synthetic construct
SEQUENCE: 7
atctggaggg gtatggcttg                                            20

SEQ ID NO: 8         moltype = DNA  length = 20
FEATURE              Location/Qualifiers
misc_feature         1..20
                     note = Synthetic oligonucleotide
source               1..20
                     mol_type = other DNA
                     organism = synthetic construct
SEQUENCE: 8
cttgttttgg ttgggggtct                                            20

SEQ ID NO: 9         moltype = DNA  length = 18
FEATURE              Location/Qualifiers
misc_feature         1..18
                     note = Synthetic oligonucleotide
source               1..18
                     mol_type = other DNA
                     organism = synthetic construct
SEQUENCE: 9
cccattgaac acggcatt                                              18

SEQ ID NO: 10        moltype = DNA  length = 20
FEATURE              Location/Qualifiers
misc_feature         1..20
                     note = Synthetic oligonucleotide
source               1..20
                     mol_type = other DNA
                     organism = synthetic construct
SEQUENCE: 10
accagaggca tacagggaca                                            20
```

COMPOSITIONS AND METHODS FOR THE TREATMENT OF INFLAMMATION IN UROLOGICAL PATHOLOGY

CROSS-REFERENCE TO RELATED APPLICATIONS

This application is a divisional application that claims priority to U.S. patent application Ser. No. 16/879,693 filed May 20, 2020, which claims the benefit of priority to U.S. Provisional Patent Application No. 62/850,015 filed May 20, 2019, which the disclosure of each is hereby incorporated by reference in its entirety.

FEDERAL FUNDING LEGEND

This invention was made with Government support under Federal Grant Nos. R01DK103534 and R01DK117890 awarded by the National Institutes of Health. The Federal Government has certain rights to this invention.

INCORPORATION BY REFERENCE OF SEQUENCE LISTING PROVIDED ELECTRONICALLY

This application contains a Sequence Listing submitted as an electronic XML file named "109726-670438_CONT," having a size in bytes of 17 kb and created on Dec. 7, 2022. The information contained in this electronic file is hereby incorporated by reference in its entirety.

BACKGROUND

Description of Related Art

Inflammasomes are supramolecular complexes that were discovered in 2002 and found to be of central importance in initiating inflammation in response to sterile as well as infectious stimuli. Nod-like receptor NLRP3 inflammasome, a subset type of inflammasome, is the best studied of the NOD-like receptor (NLR) family of pattern receptors. The NLRP3 inflammasome is comprised, in part, of the nod-like receptor NLRP3, a structural co-factor protein called thioredoxin-interacting protein (TXNIP), and the adaptor protein Apoptosis-Associated Speck-like Protein C (ASC).

In general, pattern receptors recognize molecules released from damaged or dying cells (or those with deranged metabolism), known as damage (or danger) associated molecular patterns (DAMPS) or components of pathogens known as pathogen associated molecular patterns (PAMPS). NLRP3 is the best understood NLR to recognize DAMPS and has been implicated in many diseases with a sterile inflammatory component, including diabetic complications. Upon recognition of DAMPS, NLRP3 oligomerizes and triggers enucleation of ASC. ASC in turn interacts with procaspase-1 which is cleaved and activated through an auto-proteolytic process. Caspase-1, in turn, catalyzes the enzymatic maturation IL-1β, IL-18 and gasdermin D. Gasdermin D forms a pore in the plasma membrane, triggering a programmed necrosis called pyroptosis which releases IL-1β and IL-18 that act as proinflammatory cytokines to initiate the inflammatory response.

NLRP3 has been shown to play an important role in the urinary tract of the rodent. (Inouye et al. (2018) *Curr. Urol.* 11:57-72; Purves et al. (2016) *Am. J. Physiol. Renal Physiol.* 311:F653-F662). In the rat bladder, NLRP3 is localized to the urothelium (Hughes et al. (2015) *Int. Urol. Nephrol.*

47:1953-1964; Hughes et al. (2014) *Am. J. Physiol. Renal Physiol.* 306:F299-308) where it mediates sterile inflammation in several important bladder pathologies including bladder outlet obstruction and cyclophosphamide-induced hemorrhagic cystitis. (Id.; Hughes et al. (2016) *J. Urol.* 195:1598-1605). Experimental models have also implicated NLRP3 in the response to urinary tract infections. (Hughes et al. (2016) *J. Clin. Cell Immunol.* 7(1):396; Hamilton et al. (2017) *Nature Rev. Urology* 14:284-295).

NLRP3 is also implicated in inflammatory processes in diabetic patients. Indeed, it is now appreciated that diabetes is not just a disease of high blood sugar but also a disease of deranged metabolism resulting in hyperglycemia and the production of numerous metabolites such as uric acid and free fatty acids, where these metabolites trigger inflammation that damages susceptible tissues with a resulting loss of function. (Shin et al. (2015) *Ageing Res. Rev.* 24:66-76; Hameed et al. (2015) *World J. Diabetes* 6:598-612). Recent breakthroughs in certain diabetic complications (nephropathy, retinopathy, and cardiomyopathy) have demonstrated that this inflammation results from activation of NLRP3. (Sepehri et al. (2017) *Immunol. Lett.* 192:97-103). However, the role of NLRP3 in urological disorders associated with diabetes, such as diabetic bladder dysfunction (DBD), has not previously been established. DBD affects up to 87% of diabetic patients, and there are currently no targeted therapies for DBD. (Daneshgari et al. (2006) *Semin. Nephrol.* 26:182-185; Panigrahy et al. (2017) *Diabetes Metab. Syndr.* 11:81-82).

Other diseases and disorders of urinary and bladder dysfunction involve, at least in part, inflammation in urological pathology. Urine contains many noxious chemical moieties, such as organic acids and salts, which can irritate or inflame the lumen of the urinary tract. In patients who are particularly sensitive to these, including those who have defects in the protective glycosaminoglycan (GAG) layer, they can cause urinary symptoms of urgency and frequency or even pain. The most potent forms of these irritants are the components that can crystallize into urinary stones. Once they have crystallized to a sufficiently large size, they are capable of mechanically breaching the protective GAG layer to expose the vulnerable urothelium below. Perhaps the most extreme form of this irritation is seen when stone material becomes impacted in the ureter and can cause intense pain from renal colic and local inflammation. Moreover, impacted ureteral stones produce local fibrosis and are the most common known cause of ureteral strictures that can cause long-term morbidity and need for surgical intervention. (Dong et al. (2018) *Asian J Urol.* 5(2):94-100; Roberts et al. (1998) *J. Urol.* 159(3):723-726). Exactly how these chemical urinary components interface with the urothelium to provoke functional disturbances, fibrosis, and pain is not completely understood.

The consequences of urothelial exposure to noxious chemical stimuli are thought to potentially result from inflammation. Recent studies of inflammation in innate immune cells and epithelial tissues have identified the inflammasome as being critically important in mediating this inflammatory response. (Savage et al. (2012) *Frontiers Immunol.* 3:288; Rheinheimer et al. (2017) *Metabolism.* 74:1-9; Liu et al. (2018) *Basic Res. Cardiol.* 113(1):5). In studies of gout and pseudogout (Martinon et al. (2006) *Nature.* 440(7081):237-241), calcium pyrophosphate (CPPD) and monosodium urate (MSU), two major components of urinary stones, have been shown to act as DAMPs to stimulate NLRP3 inflammasome activity in macrophages. In similar studies of osteoarthritis, both CPPD and MSU promote inflammation mediated by this inflammasome. (Campillo-Gimenez et al. (2018) *Frontiers in Immunol.* 9:2248). In their role as DAMPs, these two components are thought to potentiate NLRP3 inflammasome activation by stimulating intracellular reactive oxygen species (ROS) production. Under normal conditions, TXNIP is bound to the cellular antioxidant thioredoxin. When ROS are produced, they oxidize thioredoxin, resulting in the dissociation of TXNIP. Free TXNIP is then able to bind to NLRP3 to promote formation of the active inflammasome. While ROS-mediated NLRP3 activation, and the importance of TXNIP, have been explored in other cell types (Joshi et al. (2015) *J. Urol.* 193(5):1684-1691; Minutoli et al. (2016) *Oxid. Med. Cell Longev.* 2016:2183026), its role in stone-mediated urothelial inflammation has not previously been defined.

Moreover, in certain instances, symptoms associated with urological diseases and disorders are not limited to the urinary tract. For example, there are numerous accounts in the literature of the association between Lower Urinary Tract Symptoms (LUTS) and depression. (Coyne et al. (2009) *BJU Intl.* 103 Suppl 3: 4-11). Particularly persuasive are the conclusions of the EpiLUTS study (Epidemiology of LUTS study) study (Id.; Milsom et al. (2012) *Urology* 80: 90-96), although mood disorders have been anecdotally associated with many of the underlying diseases for years including recurrent urinary tract infections (Renard et al. (2014) *Infect. Dis. Ther.* 4(1):125-135), overactive bladder (Golabek et al. (2016) *Psychiatr. Pol.* 50: 417-430; Lai et al. (2015) *BMC Urol.* 15: 14; Tzeng et al. (2019) *J. Investig. Med.* 67(2):312-318; Wu et al. (2017) *Front Cell Infect. Microbiol.* 7:488), bladder outlet obstruction (Dunphy et al. (2015) *Rev. Urol.* 17:51-57) and incontinence (Giannantoni et al. (2018) *J. Urol.* 199:e350-e351). Probably best known for this association is interstitial cystitis (IC)/bladder pain syndrome, a prevalent condition affecting up to 8 million women in the United States (Berry et al. (2011) *J. Urol.* 186: 540-544) that is strongly associated with depression (Hepner et al. (2012) *Urology* 80: 280-285; McKernan et al. (2018) *Neurourology and Urodynamics* 37: 926-941; Meijlink J M. (2017) *Urologia* 84: 5-7; Muere et al. (2018) *Pain Manag. Nurs.* 19(5):497-505) and suicidal ideation (Hepner et al. (2012) *Urology* 80: 280-285). Despite considerable effort to understand the origin of these symptoms, the etiology has remained enigmatic.

Recently, breakthroughs have shown that several acute and chronic diseases of peripheral tissues trigger inflammation in the central nervous system (CNS). (Hamasaki et al. (2018) *J Neurosci. Res.* 96: 371-378). Much of this groundbreaking knowledge is derived from studies of the gastrointestinal system. For example, Hsieh et al. demonstrated that as little as 30 minutes of ischemia in the intestines results in an increase in expression of inflammatory mediators and activation of microglia within the CNS. (Hsieh et al. (2011) *Shock* 36: 424-430). In addition, irritable bowel syndrome, which might be considered a colonic parallel to interstitial cystitis due to its unknown origin, inflammatory nature, and similar psychosocial comorbidities, also triggers neuroinflammation. (Daulatzai M A. (2014) *Neurochem. Res.* 39: 624-644). Importantly, the conditions peripheral to central pathways in question are not limited to the gastrointestinal system, for other peripheral insults such as burns, cardiac arrest, and acute pancreatitis can all result in CNS inflammation. (Hamasaki et al. (2018) *J Neurosci Res* 96: 371-378). Neuroinflammation is well-known to cause mood disorders (Miller et al. (2009) *Biol. Psychiatry* 65:732-741; Miller and Raison (2016) *Nature Rev. Immunol.* 16:22-34; Noto et al. (2014) *Neuroimmunomodulation* 21:131-139;

Sayana et al. (2017) *J. Psychiatr. Res.* 92:160-182; Teixeira and Muller (2014) *Neuroimmunomodulation* 21:71) and plays a major role in debilitating diseases such as major depressive disorder and bipolar disorder (Colpo et al. (2018) *Expert Rev. Neurother.* 18: 139-152; Haroon et al. (2017) *Neuropsychopharmacology* 42: 193-215).

Clearly, the evidence suggests peripheral insults can trigger neuroinflammation and neuroinflammation can cause pain, but it has been further hypothesized that neuroinflammation may continue to alter normal physiology following the resolution of local inflammation, such as persistent discomfort in the bladder following an acute or recurrent infection and it may do so by changing nociceptive thresholds. Thus, neuroinflammation may explain residual symptoms. Equally important, neuroinflammation has been implicated in the development of mood disorders, including major depressive disorder and generalized anxiety disorder, which are prevalent co-morbid conditions in patients with chronic pain syndromes such as IC. However, whether insults to the bladder may result in neuroinflammation in the CNS that leads to the psychosocial symptoms, or the underlying mechanism under which this might occur, have not previously been established or understood.

BRIEF SUMMARY OF THE DISCLOSURE

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One aspect of the present disclosure provides a method of treating inflammation in the bladder in a subject in need thereof, comprising administering to the subject a therapeutically effective amount of an inflammasome inhibitor.

In some embodiments of the disclosure, the inflammation in the bladder is an acute inflammation or a chronic inflammation.

In some embodiments of the disclosure, the inflammation in the bladder is induced by a danger associated molecular pattern (DAMP) or a pathogen associated molecular pattern (PAMP). In some embodiments of the disclosure, the DAMP is ATP, calcium pyrophosphate (CPPD), monosodium urate (MSU), high mobility group box-1 (HMG-B1), albumin, uromodulin, uric acid crystals, hypoxia, acrolein, calcium oxalate, cholesterol, reactive oxidative species (ROS) serum amyloid A (SAA), amyloid R fibril, hyaluronan, aluminum, asbestos, silica, UV radiation, drusen, or skin irritants.

In some embodiments of the disclosure, the PAMP is a fungus (e.g., *Candida albicans, Saccharomyces cerevisiae,* or *Aspergillus fumigatus*), bacteria (e.g., *Listeria monocytogenes, Staphylococcus aureus, Escherichia coli, Chlamydia pneumonia, Mycobacterium tuberculosis, Clostridium difficile, Bordetella pertussis, Vibrio cholera, Neisseria gonorrhoeae,* or *Streptococcus pyogenes*), or virus (e.g., Influenza A, adenovirus, Sendai virus, Varicella-zoster, or herpes).

In some embodiments of the disclosure, the inflammation in the bladder comprises urothelial cell damage.

In some embodiments of the disclosure, the subject is a human.

In some embodiments of the disclosure, the inflammasome inhibitor is an NLRP1 inflammasome inhibitor, an NLRP3 inflammasome inhibitor, an NLRP6 inflammasome inhibitor, an NLRP7 inflammasome inhibitor, an NLPR9 inflammasome inhibitor, an NLRP12 inflammasome inhibitor, an NLRC4 inflammasome inhibitor, or an AIM2 inflammasome inhibitor.

In other embodiments of the disclosure, the inflammasome inhibitor is an NLRP3 inflammasome inhibitor. In some embodiments of the disclosure, the NLRP3 inflammasome inhibitor (e.g., glyburide). In other embodiments of the present disclosure, the NLRP3 inflammasome inhibitor is a TXNIP inhibitor (e.g., verapamil), ASC inhibitor, NEK7 inhibitor, Gasdermin D inhibitor, capspase-11 inhibitor, capsase-1 inhibitor (e.g., verapamil), IL-1β inhibitor, IL-18 inhibitor or combinations thereof. In other embodiments of the present disclosure, the NLRP3 inflammasome inhibitor is a ROS scavenger (e.g., N-acetylcysteine (NAC)).

In some embodiments of the disclosure, the subject is diagnosed with diabetes, a urinary tract infection, urinary frequency, fibrosis, bladder outlet obstruction (BOO), interstitial cystitis, CP-induced cystitis, depression, anxiety, neuroinflammation, a gynecologic cancer, kidney stones, a pelvic inflammatory disorder, endometriosis, Chron's disease, diverticulitis, lupus, tuberculosis, and combinations thereof.

In some embodiments of the present disclosure, the subject had been exposed to chemotherapy, radiation, a catheter, or a urinary stent.

Another aspect of the present disclosure provides a method of treating diabetic bladder dysfunction (DBD) in a subject in need thereof, the method comprising administering to the subject a therapeutically effective amount of an inflammasome inhibitor.

Yet another aspect of the present disclosure provides a method of treating or preventing a condition associated with neuroinflammation, the method comprising administering a therapeutically effective amount of an inflammasome inhibitor.

In some embodiments of the present disclosure, the subject that has been diagnosed with inflammation of the bladder or an inflammatory bladder disorder. In some embodiments of the disclosure, the inflammatory bladder disorder is interstitial cystitis, BOO, or DBD.

In some embodiments of the present disclosure, the condition associated with neuroinflammation is a mood disorder in the subject (e.g., depression, dysthymic disorder, bipolar disorder, anxiety, or anhedonia, or combinations thereof).

In some embodiments of the disclosure, the method further comprises administering a therapeutically effective amount of an antidepressant agent. In some embodiments of the disclosure, the antidepressant agent is selected from the group consisting of a selective serotonin reuptake inhibitors (SSRIs), a norepinephrine-dopamine reuptake inhibitors (NDRIs), or a monoamine oxidase inhibitors (MAOIs). In some embodiments, the antidepressant agent is fluoxetine.

Yet another aspect of the present disclosure provides a new murine model of diabetic mice lacking the NLRP3 inflammasome (NLRP3$^{-/-}$, diab).

Yet another aspect of the present disclosure provides a composition comprising an inflammasome inhibitor and a pharmaceutically acceptable carrier or excipient.

Additional features and advantages are described herein, and will be apparent from the following Detailed Description, Drawings, and the claims.

BRIEF DESCRIPTION OF THE DRAWINGS

The foregoing aspects and other features of the disclosure are explained in the following description, taken in connection with the accompanying drawings, wherein:

FIGS. 1A-1G show analysis of various DAMPS on inflammasome activation in urothelial cells in vitro. Cells were isolated, plated and treated with the doses of the various compounds indicated. Following incubation periods described below, caspase-1 was measured. FIG. 1A is a graph showing ATP dose-response. Each point represents the mean±SEM. n=5 for each dose. Asterisks indicate significant differences from 0 mM ATP control. ***p<0.001 by ANOVA followed by Tukey's post-hoc test. FIG. 1B. is graph showing the effects of LPS on the ATP dose-response. Urothelial cells were plated for 24 h, then LPS (1 μg/mL) in 10 μL PBS (or PBS alone) added for an additional 24 h. Then the indicated doses of ATP were added for 1 h prior to caspase-1 analysis. The −LPS samples (closed triangles) are the exact same samples shown in FIG. 1A, but are included in FIG. 1B for ease of comparison. Each point represents the mean±SEM. n=5 for each dose. Student's two-tailed t-test was used to compare the −LPS and the +LPS sample at each dose of ATP. FIG. 1C is a graph showing the streptozotocin dose response. Streptozotocin was prepared as a 200 mM stock in 0.1 M citrate buffer (pH 4.4) and dilutions made in media before being added (10 μL) to the wells at the indicated final concentrations. Cells were incubated 24 h before the addition of 1.25 mM ATP for 1 h and subsequent analysis. Each point represents the mean±SEM. n=5 for each dose. *p<0.05 by ANOVA followed by Tukey's post-hoc test. FIG. 1D is a graph showing the monosodium urate dose response. Monosodiun urate crystals (InvivoGen, San Diego, CA) were received at 5 mg/mL and dilutions prepared in complete media just prior to addition to the well (in 10 μL). Cells were incubated 24 h before the addition of 1.25 mM ATP for 1 h and analysis. Each point represents the mean±SEM. N=6 for each dose. *p<0.05 p<0.01 by ANOVA followed by Tukey's post-hoc test. FIG. 1E is a graph showing the high mobility group box 1 protein (HMGB-1; ProSci, Poway, CA) dose response. HMGB-1 was resuspended and diluted in complete media just prior to addition (10 μL) to the wells at the indicated final concentrations. Cells were incubated 24 h before the addition of 1.25 mM ATP for 1 h and subsequent analysis. Each point represents the mean±SEM. n=6 for each dose. p<0.01 by ANOVA followed by Tukey's post-hoc test. FIG. 1F is a graph showing the N-hexanoyl-D-erythro-sphingosine dose response. N-hexanoyl-D-erythro-sphingosine (C6-Ceramide; Alfa Aesar, Haverhill, M A) was dissolved in DMSO and diluted in complete media prior to addition to the wells (10 μL). Cells were incubated 24 h before the addition of 1.25 mM ATP for 1 h and analysis. Each point represents the mean±SEM. n=6 for each dose. *p<0.05 p<0.01 by ANOVA followed by Tukey's post-hoc test. FIG. 1G is a graph showing the advanced Glycation Endproduct-BSA dose response. Glycation Endproduct-BSA (AGE; Calbiochem, Millipore Sigma, Burlington, MA) was prepared and diluted in complete media prior to addition to the wells. Cells were incubated 24 hour before the addition of 1.25 mM ATP for 1 h and analysis. Each point represents the mean±SEM. n 6 for each dose. p<0.01 ***p<0.001 by ANOVA followed by Tukey's post-hoc test.

FIGS. 4A-4B shows that blood glucose is not affected by knocking out NLRP3. FIG. 4A is a graph showing that blood glucose is very significantly increased in the diabetic mouse with a NLRP3+/+ genotype. Bars are mean±SEM. n=27 (nondiabetic), 12 (diabetic). *p<0.0001 by paired Student's t-test. FIG. 4B is a graph showing that blood glucose is significantly elevated in the diabetic mouse with a NLRP3−/− genotype. Bars are mean±SEM. n=18 (nondiabetic), 21 (diabetic). *p<0.0001 by Student's two tailed t-test. ANOVA followed by Tukey's post-hoc test was also used to compare all groups. No additional significant differences were found.

FIG. 5A is a graph showing that the amount of Evans Blue dye in the bladder was increased in diabetic mice compared to nondiabetic (both NLRP3+/+). Bars are mean±SEM. n=FIG showing that diabetes did not affect the movement of Evans Blue into the bladder in the absence of NLRP3. Bars are mean±SEM. n=6 (nondiabetic), 16 (diabetic). ANOVA followed by Tukey's post-hoc test was also used to compare all groups. No additional significant differences were found.

FIG. 6A is a representative tracing from the NLRP3+/+ strains. FIG. 6B is a representative tracings from the NLRP3−/− strains.

FIGS. 7A-7H shows that NLRP3 is responsible for bladder dysfunction associated with DBD. FIG. 7A is a graph showing the voiding volume in nondiabetic and diabetic mice (both NLRP3+/+). FIG. 7B is a graph showing the voiding volume in nondiabetic and diabetic mice with NLRP3 deleted (NLRP3−/−). FIG. 7C is a graph showing the frequency of voiding in nondiabetic and diabetic mice (both NLRP3+/+). FIG. 7D is a graph showing the frequency of voiding in nondiabetic and diabetic mice with NLRP3 deleted (NLRP3−/−). FIG. 7E is a graph showing the post-void residual (PVR) volume, or volume of urine remaining in the bladder immediately after the last void in nondiabetic and diabetic mice (both NLRP3+/+). FIG. 7F is a graph showing the post-void residual (PVR) volume, or volume of urine remaining in the bladder immediately after the last void, in nondiabetic and diabetic mice with NLRP3 deleted (NLRP3−/−). No PVR was ever detected in any of the nine nondiabetic/NLRP3+/+ mice examined. FIG. 7G is a graph showing the voiding efficiency in nondiabetic and diabetic mice (both NLRP3+/+) as calculated as 100(voided volume)/(voided volume+PVR). FIG. 7H is a graph showing the voiding efficiency in nondiabetic and diabetic mice with NLRP3 deleted (NLRP3−/−) as calculated as 100(voided volume)/(voided volume+PVR). For all graphs, bars are mean±SEM. n=9 and 7 for nondiabetic and diabetic mice, respectively, that are NLRP3+/+. N=10 and 9 for nondiabetic and diabetic mice, respectively, that are NLRP3−/−. p<0.01, *p<0.001 by a Student's two-tailed t-test. ANOVA followed by Tukey's post-hoc test was also used to compare all groups for each endpoint. The only additional significant differences found were in void volume comparing NLRP3+/+ diabetic to NLRP3−/− diabetic (p<0.05) and voiding efficiency comparing NLRP3+/+ diabetic to NLRP3−/− nondiabetic.

FIG. 8A is a representative micrograph of PGP9.5 staining (i.e. all neurons) in the bladder used to quantify nerves. The left micrograph depicts the entire transverse cross section stained and scanned into a TIFF file used for quantitation, as described in the methods section. The box indicates the area zoomed in on the right micrograph to allow better visualization. Block arrow points at urothelia that stain non-specifically for PGP9.5, or at least are of non-neuronal origin. Arrows indicate the brown staining in the bladder wall considered to stain positive for this antigen. FIG. 8U is a graph showing the density of PGP9.5$^+$ neurons in the same sections and groups quantitated in FIG. 8Q. For all graphs bars represent mean±SEM. For FIG. 8B, FIG. 8D and FIG. 8F, n=11. For FIG. 8C, FIG. 8E and FIG. 8G, n=10. For FIG. 8I, FIG. 8K and FIG. 8M, n=6. For FIG. 8J, FIG. 8L and FIG. 8N, n=7.

Figure 8A:
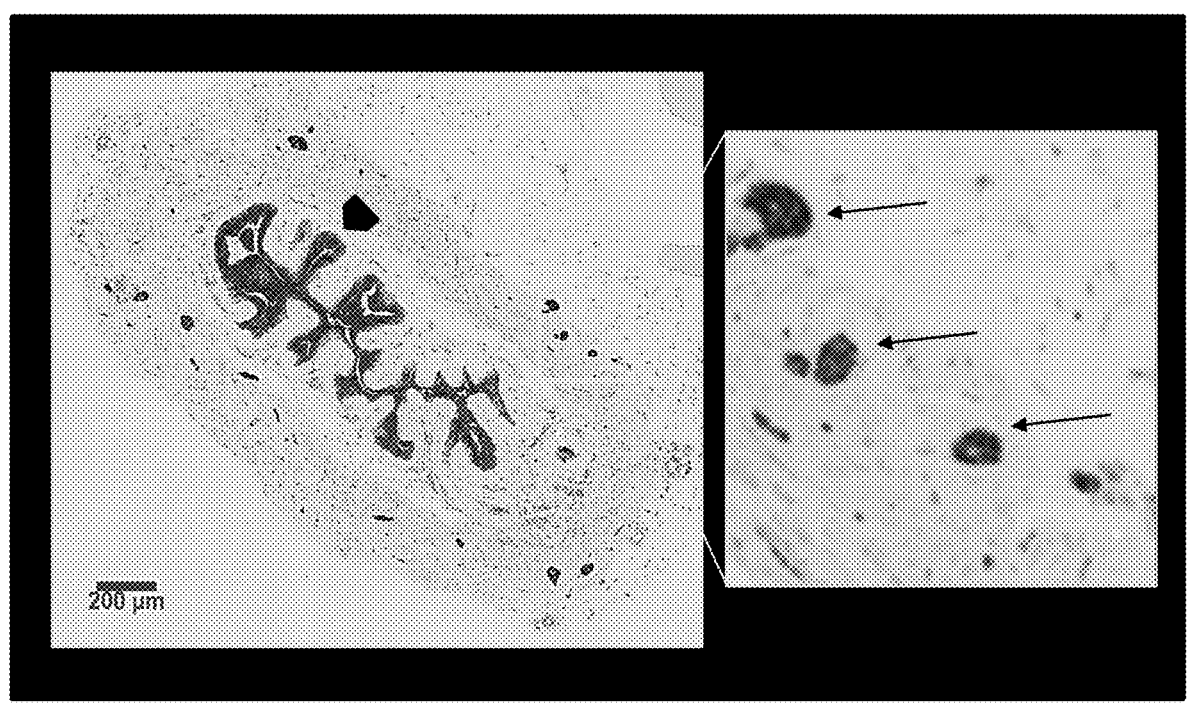
FIG. 8A-8U shows NLRP3 controls changes in the densities of nerves related to specific DBD symptoms.
Figures 8B, 8C:
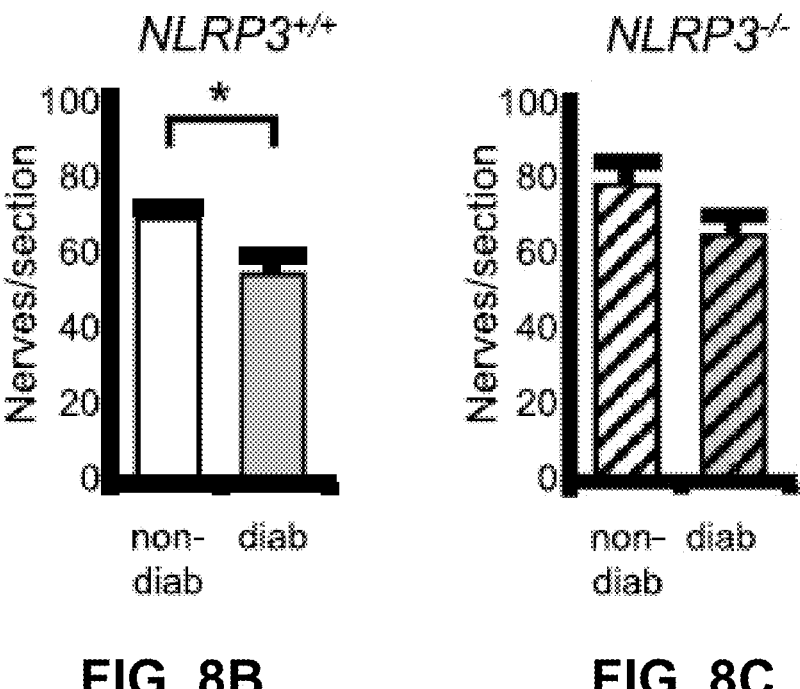
FIG. 8B is a graph showing the number of PGP9.5$^+$ nerves in bladder wall of 15 week mice from nondiabetic (non diab) and diabetic (diab) mice that express NLRP3 (NLRP3$^{+/+}$).
FIG. 8C is a graph showing the same analysis as FIG. 8B in mice that have the NLRP3 gene deleted (NLRP3$^{-/-}$).
Figures 8D, 8E:
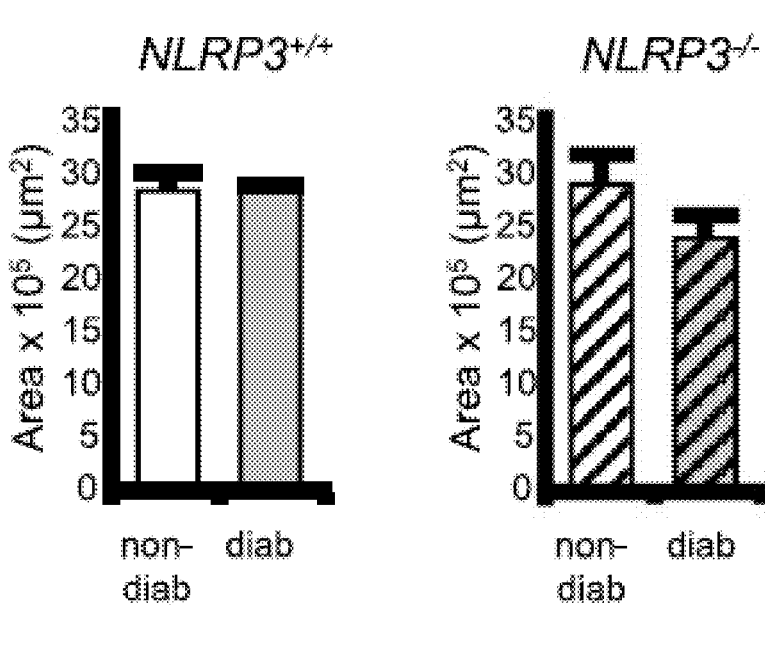
FIG. 8D is a graph showing the size of the bladder wall in the same sections and groups quantitated in FIG. 8B.
FIG. 8E is a graph showing the size of the bladder wall in the same sections and groups quantitated in FIG. 8C.
Figures 8F, 8G:
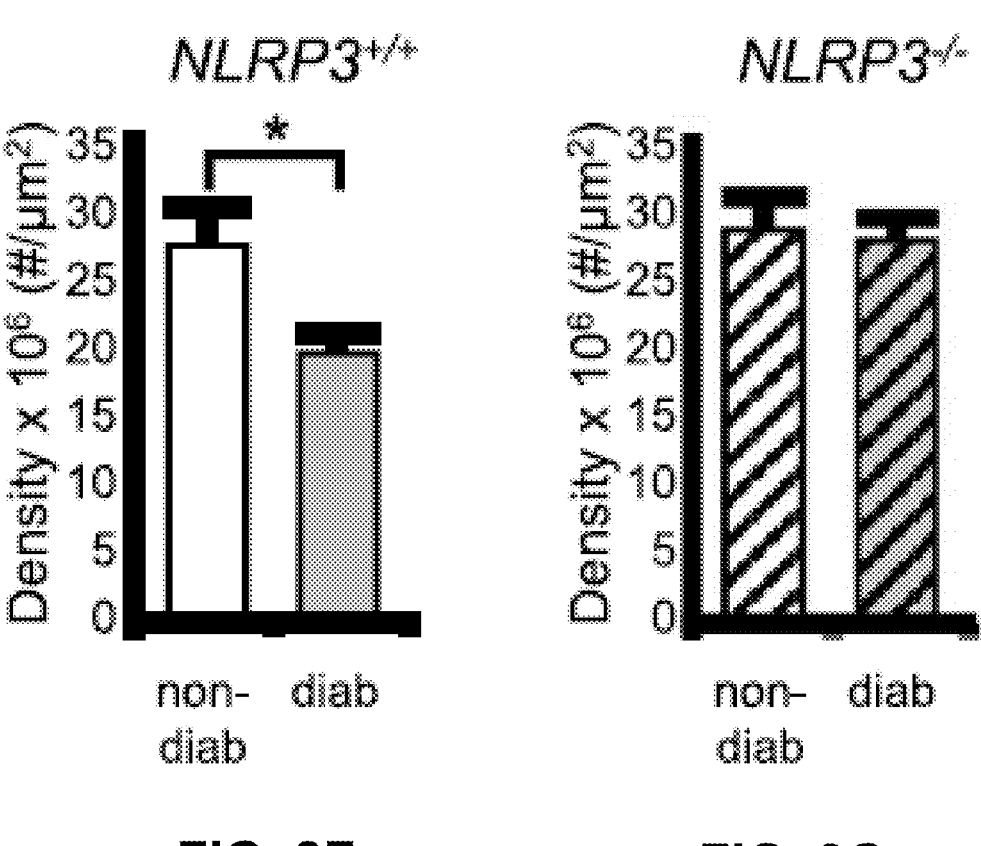
FIG. 8F is a graph showing the density of PGP9.5$^+$ neurons in the same sections and groups quantitated in FIG. 8B.
FIG. 8G is a graph showing density of PGP9.5$^+$ neurons in the same sections and groups quantitated in FIG. 8C.
Figure 8H:
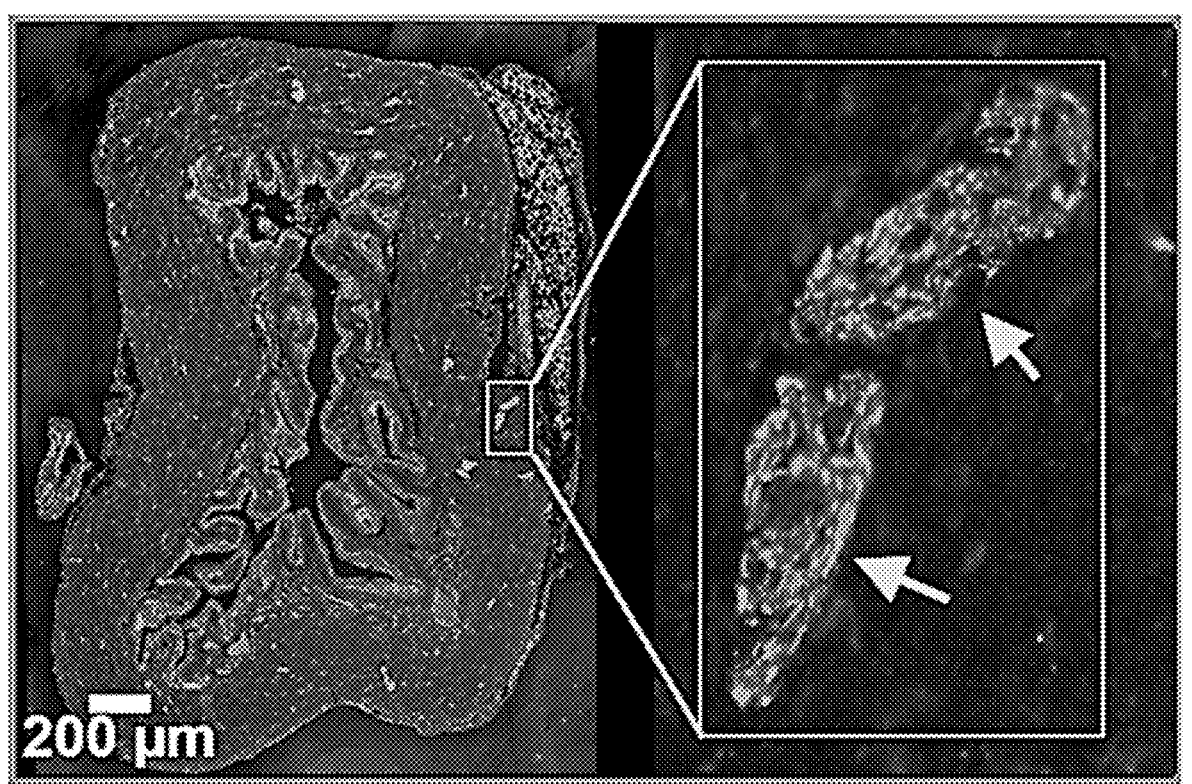
FIG. 8H are representative micrographs of NF-200 staining (Aδ-fibers) in the bladder used to quantify nerves. The left micrograph depicts the entire transverse cross section while the yellow box indicates the area zoomed in on the right and arrows point at staining in the bladder wall considered to be positive for this antigen.
Figures 8I, 8J:
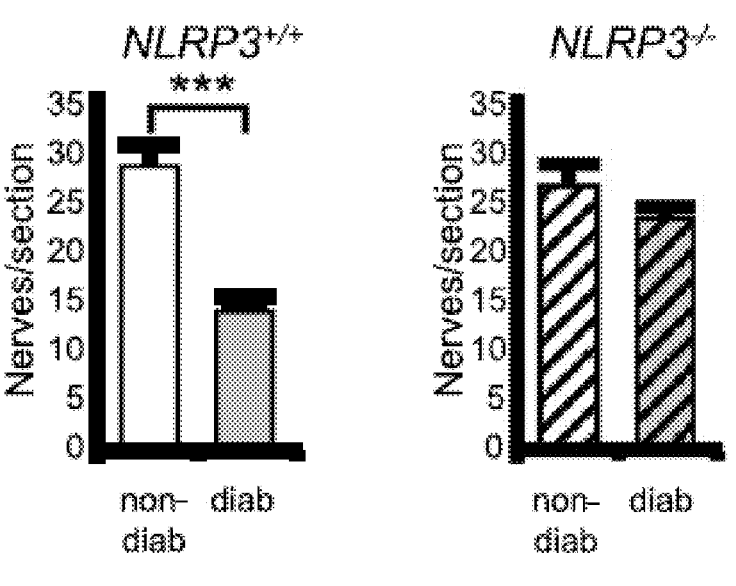
FIG. 8I is a graph showing the number of Aδ-fibers in bladder wall of 15 week mice from nondiabetic (non diab) and diabetic (diab) mice that express NLRP3 (NLRP3$^{+/+}$).
FIG. 8J is a graph showing the same analysis as FIG. 8I in mice that have the NLRP3 gene deleted (NLRP3$^{-/-}$).
Figures 8K, 8L:
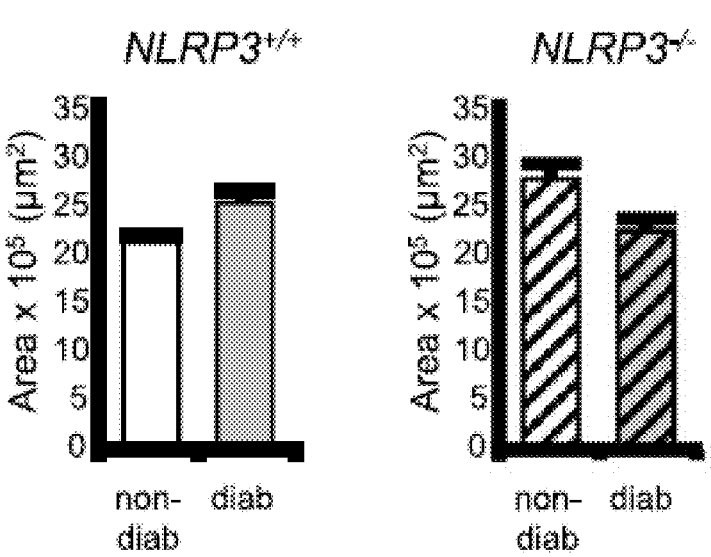
FIG. 8K is a graph showing the size of the bladder wall in the same sections and groups quantitated in FIG. 8I.
FIG. 8L is a graph showing the size of the bladder wall in the same sections and groups quantitated in FIG. 8J.
Figures 8M, 8N:
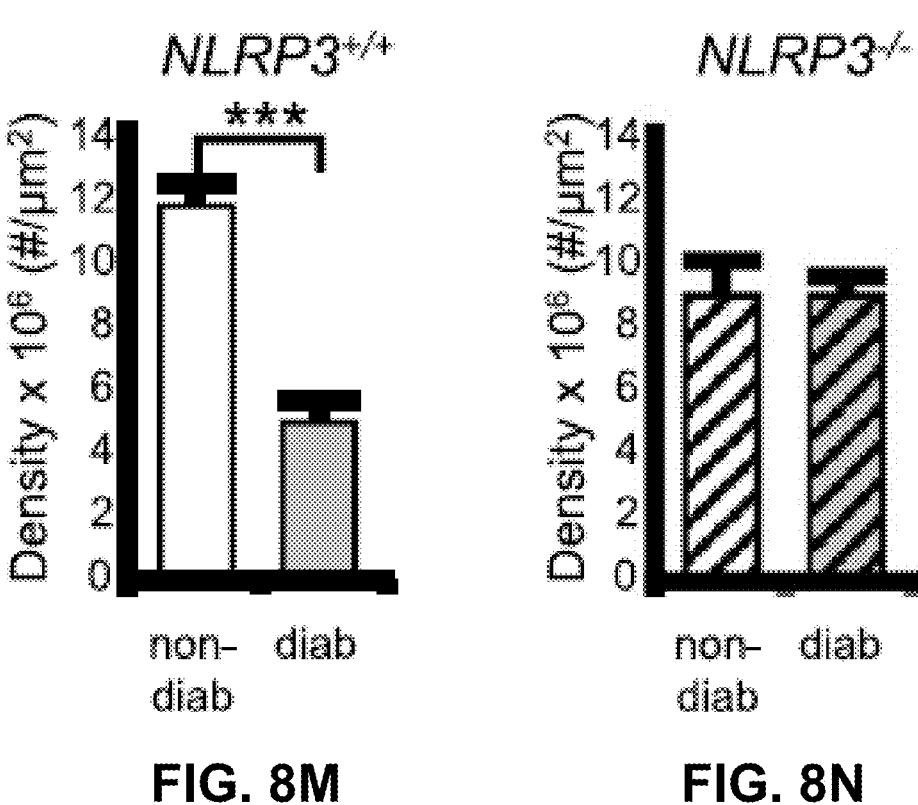
FIG. 8M is a graph showing the density of PGP9.5$^+$ neurons in the same sections and groups quantitated in FIG. 8I.
FIG. 8N is a graph showing the density of PGP9.5$^+$ neurons in the same sections and groups quantitated in FIG. 8J.
Figure 8O:
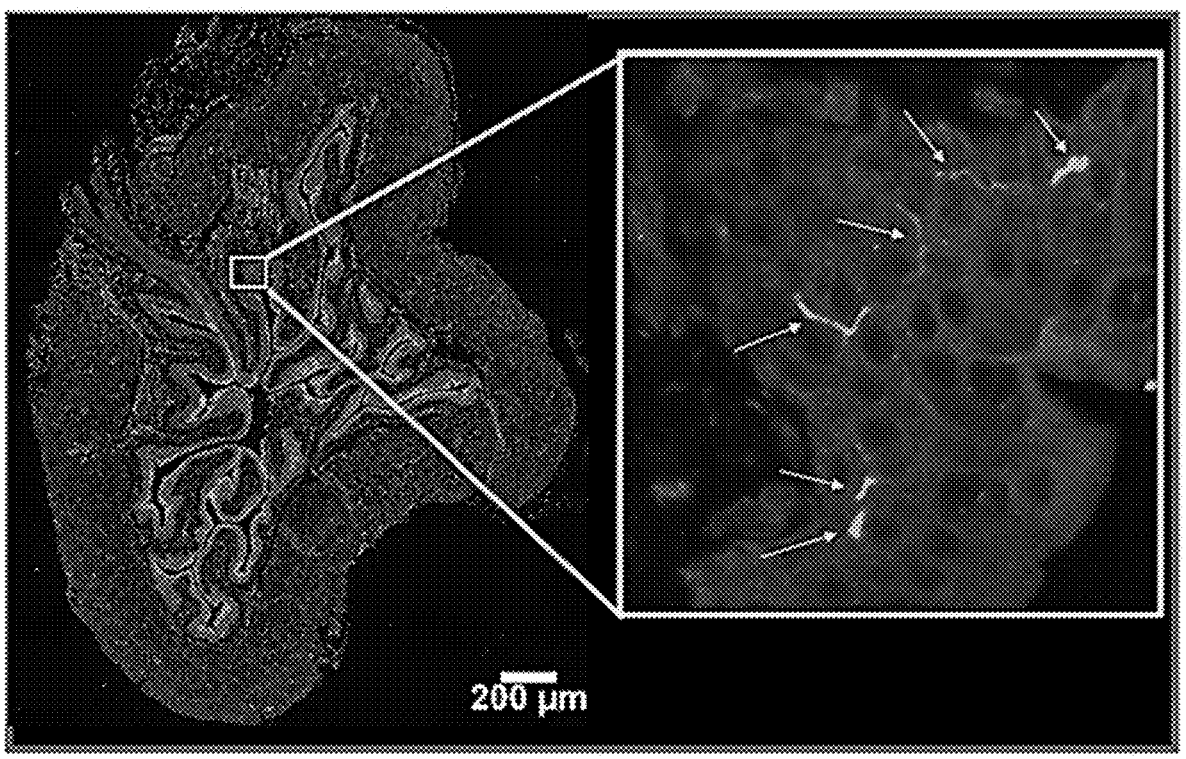
FIG. 8O are representative micrographs of CGRP staining (C-fibers) in the bladder used to quantify nerves. The left micrograph depicts the entire transverse cross section while the yellow box indicates the area zoomed in on the right and arrows point at staining in the bladder wall considered to be positive for this antigen. This section is also stained with the nuclear stain 4′,6-diamidino-2-phenylindole (DAPI) in the coverslipping material to allow easier visualization.
Figures 8P, 8Q:
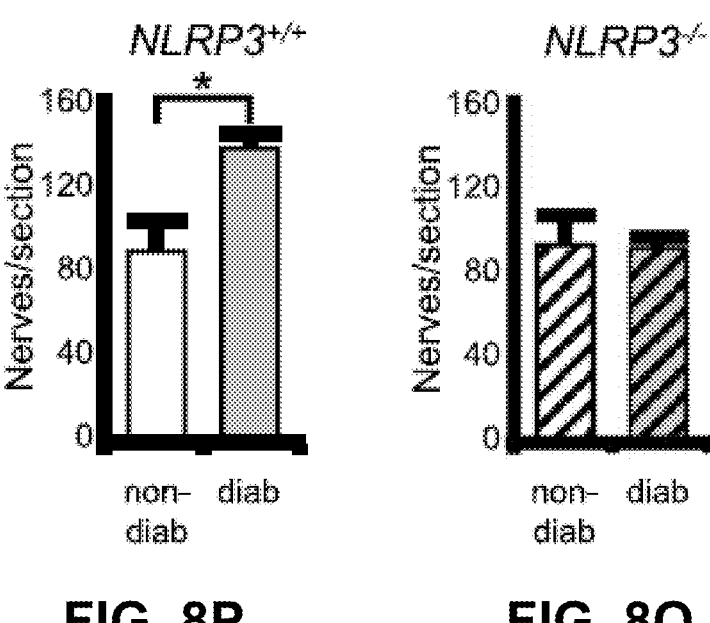
FIG. 8P is a graph showing the number of C-fibers in bladder wall of 15 week mice from nondiabetic (non diab) and diabetic (diab) mice that express NLRP3 (NLRP3$^{+/+}$).
FIG. 8Q is a graph showing the same analysis as FIG. 8P in mice that have the NLRP3 gene deleted (NLRP3$^{-/-}$).
Figures 8R, 8S:
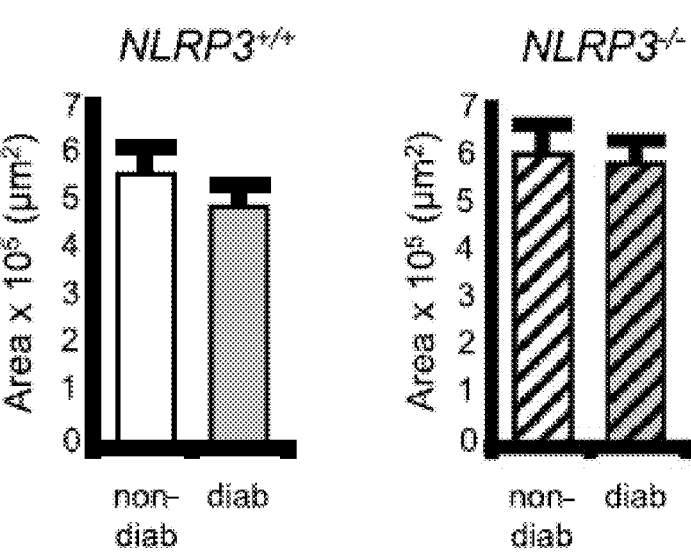
FIG. 8R is a graph showing the size of the bladder wall in the same sections and groups quantitated in FIG. 8P.
FIG. 8S is a graph showing the size of the bladder wall in the same sections and groups quantitated in FIG. 8Q.
Figures 8T, 8U:
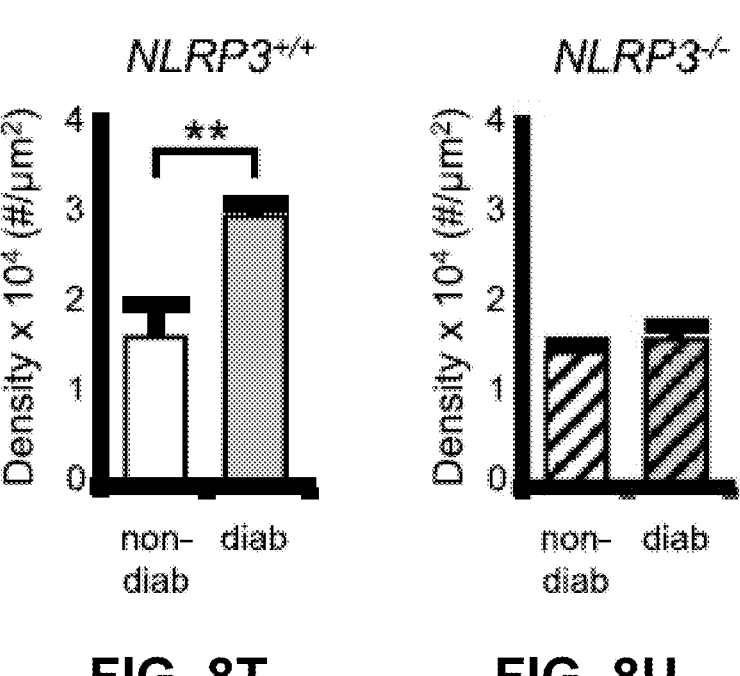
FIG. 8T is a graph showing the density of PGP9.5$^+$ neurons in the same sections and groups quantitated in FIG. 8P.

For FIG. 8P, FIG. 8R and FIG. 8T, n=4 (non diab) and 6 (diab). For FIG. 8Q, FIG. 8S and FIG. 8U, n=3 (non diab) and 4 (diab). *p<0.05, p<0.01, *p<0.001 by a Student's two-tailed t-test. ANOVA followed by Tukey's post-hoc test was also used to compare all groups for each endpoint. The only additional significant differences found were in Aδ-fiber nerve number comparing NLRP3+$^{+/+}$ diabetic to NLRP3$^{-/-}$ diabetic (p<0.05), bladder wall size in the Aδ-fiber study comparing NLRP3$^{+/+}$ nondiabetic to NLRP3$^{-/-}$ nondiabetic (p<0.05), Aδ-fiber nerve number comparing NLRP3$^{+/+}$ diabetic to NLRP3$^{-/-}$ diabetic (p<0.05). In the C-fiber studies the NLRP3$^{+/+}$ diabetic was significantly different from both NLRP3$^{-/-}$ strains in the nerve number and density graphs (p<0.05).

Figure 9A:
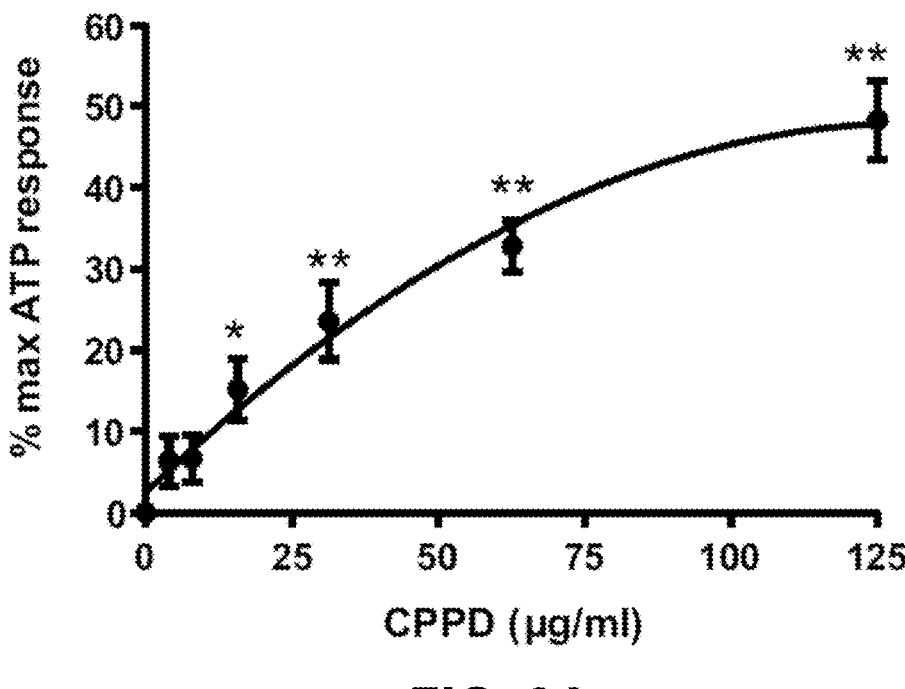
Figure 9B:
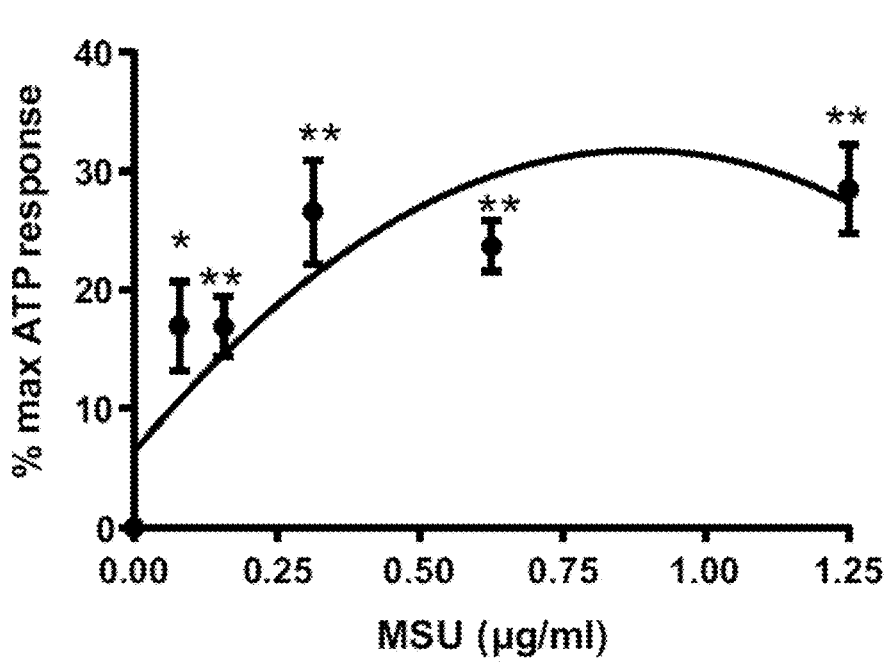
Figure 9C:
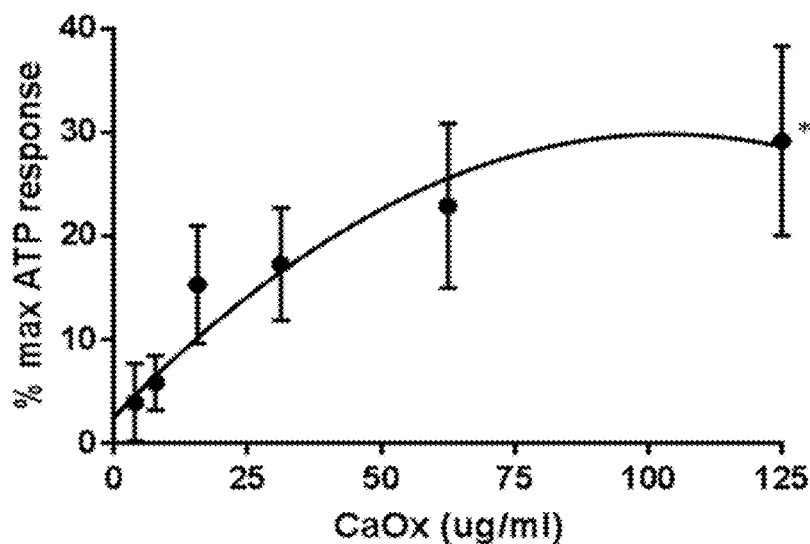

FIGS. 9A-9C are graphs showing that stone DAMPs activate caspase-1 in a dose-dependent manner. FIG. 9A is a graph showing that CPPD activates caspase-1 in urothelial cells in a dose-dependent manner. FIG. 9B is a graph showing that MSU activates caspase-1 in urothelial cells in a dose-dependent manner. FIG. 9C is a graph showing that calcium oxalate activates caspase-1 in urothelial cells in a dose-dependent manner. n=9 for all doses of CPPD and MSU, and n=8,5,8,7,7,8,8 for the doses of calcium oxalate, respectively. *p<0.05; p<0.01; *p<0.001 by one-way ANOVA and Dunnett's post-hoc test.

Figure 10A:
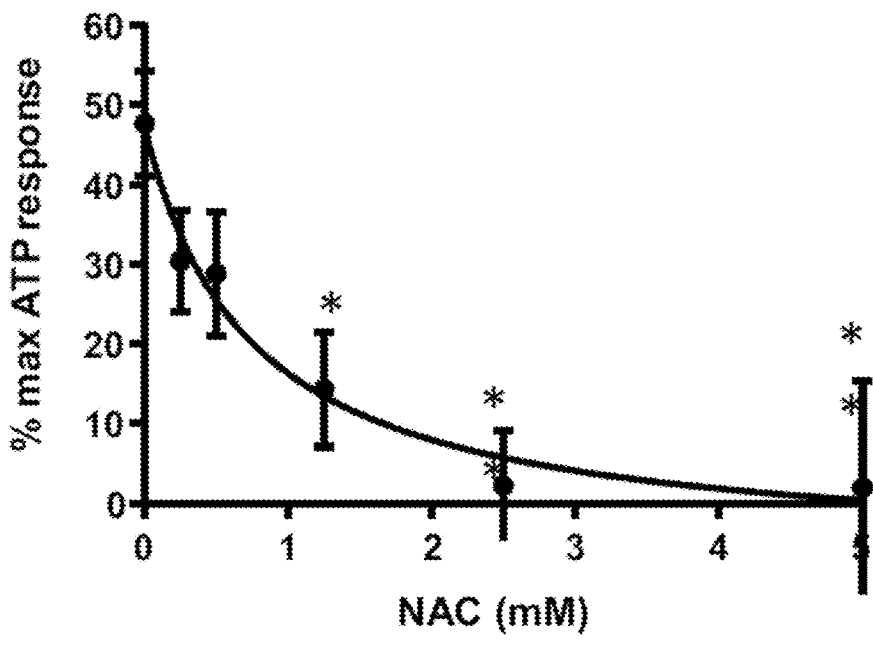
Figure 10B:
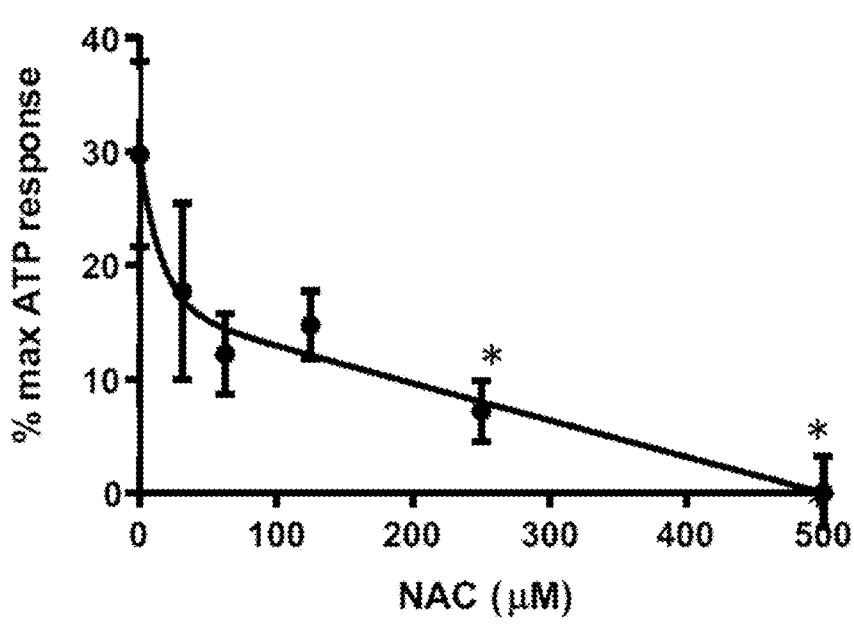

FIGS. 10A-10B are graphs showing that NAC inhibits caspase-1 activation in cells treated with CPPD or MSU. FIG. 10A is a graph showing that that NAC inhibits caspase-1 activation in urothelial cells treated with CPPD. FIG. 10B is a graph showing that that NAC inhibits caspase-1 activation in urothelial cells treated with MSU. n=9 for all NAC treatment doses for both CPPD and MSU. *p<0.05; p<0.01; *p<0.001 by one-way ANOVA and Dunnett's post-hoc test.

Figure 11A:
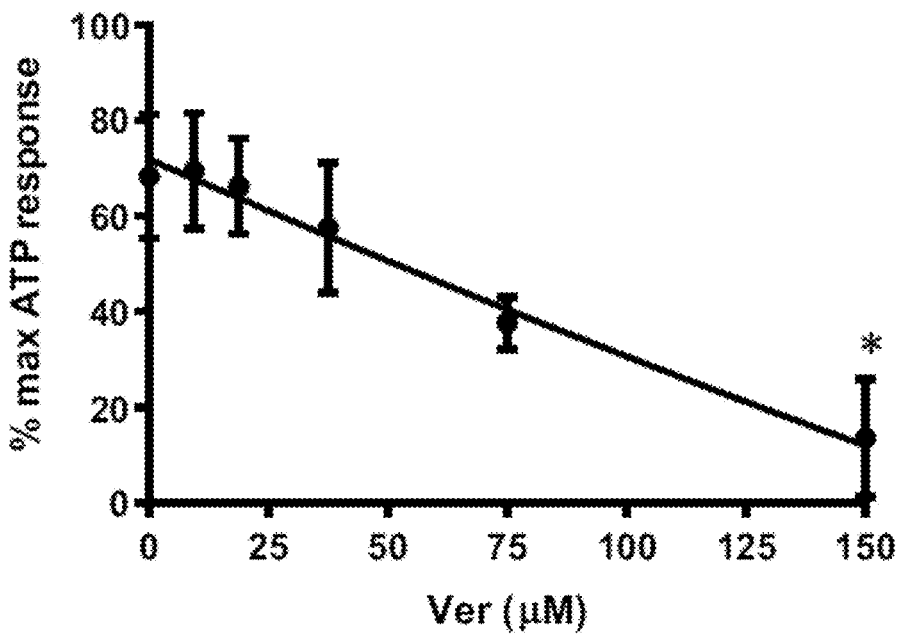
Figure 11B:
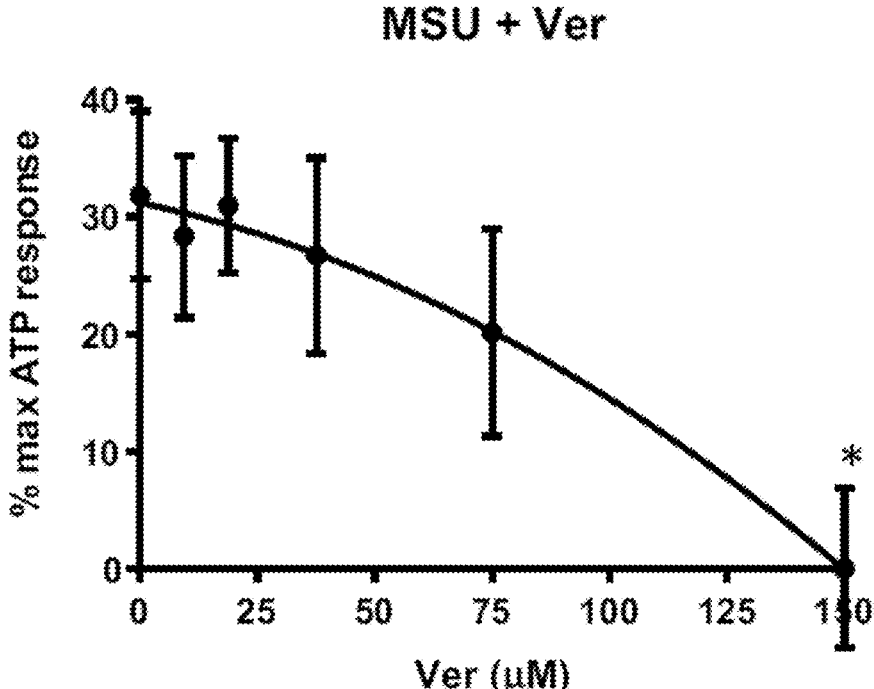

FIGS. 11A-11B are graphs showing that verapamil (ver) suppresses caspase-1 activation.

FIG. 11A is a graph showing that ver suppresses caspase-1 activation in urothelial cells treated with CPPD. FIG. 11B is a graph showing that ver suppresses caspase-1 activation in urothelial cells treated with MSU. n=10 for all doses of Verapamil and CPPD treated wells; n=5 for all doses of Verapamil and MSU treated wells. *p<0.05; p<0.01; *p<0.001 by one-way ANOVA and Dunnett's post-hoc test.

Figure 12:
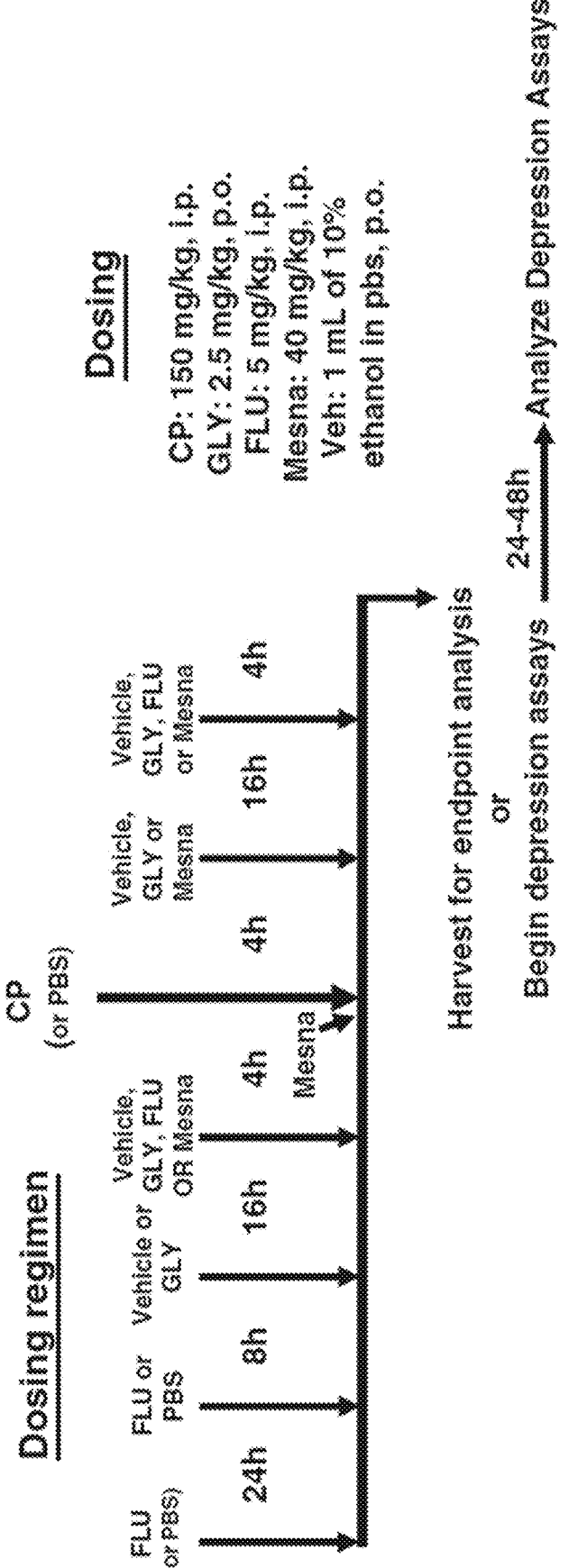

FIG. 12 is a schematic showing dosing regimen for the experiments. Rats were given the drugs at the indicated doses at the indicated times. CP, cyclophosphamide; GLY, glyburide; FLU, fluoxetine; Veh, vehicle; Mesna, 2-mercaptoethane sulfonate sodium.

Figure 13A:
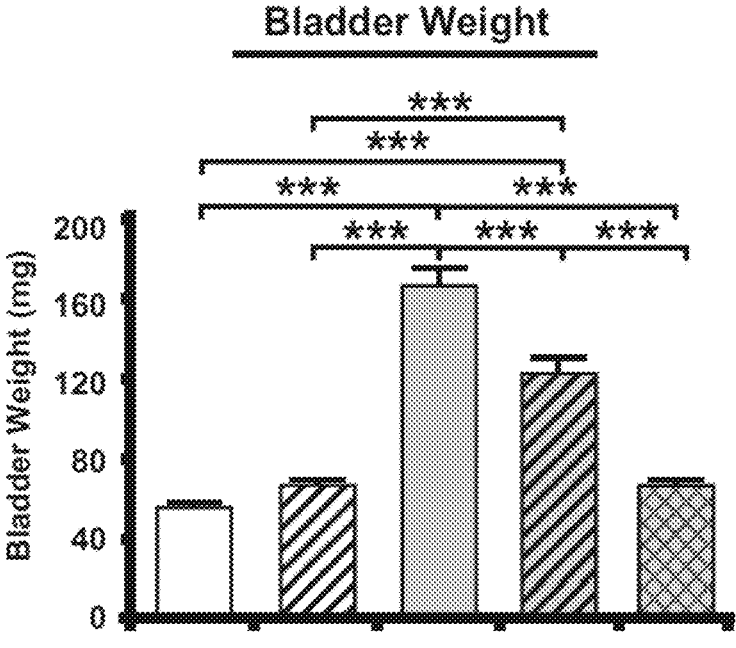
Figure 13B:
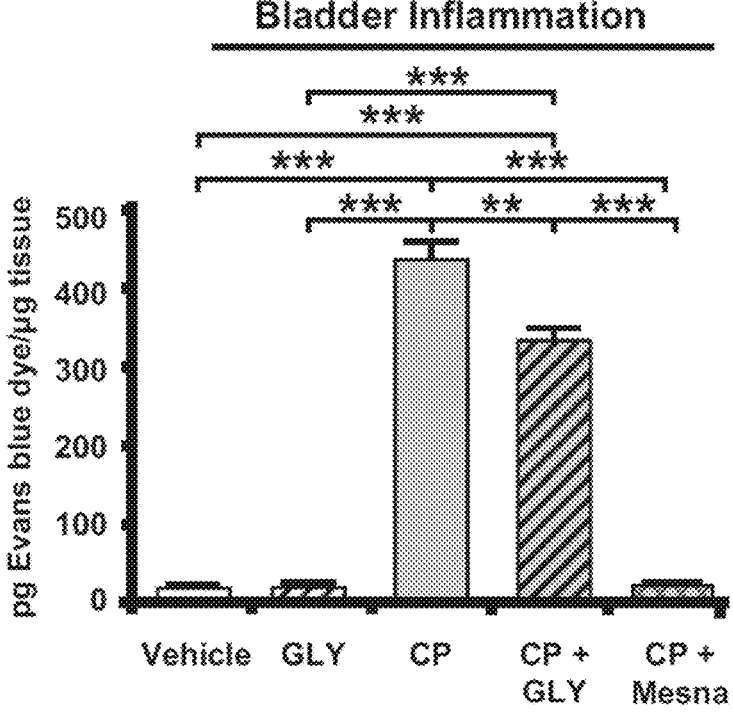

FIGS. 13A-13B are graphs showing bladder weights and inflammation are increased in response to CP and this is blocked by GLY or Mesna. FIG. 13A is a graph showing that bladder weights at sacrifice were higher after CP treatment and this was reduced by treatment with GLY or Mesna. Bars represent mean bladder weight±SEM. [Vehicle: n=32; CP: n=42; GLY: n=17; CP+GLY: n=20; CP+Mesna: n=34]. FIG. 13B is a graph showing that inflammation in the bladder, as measured by Evans blue dye extravasation, was increased after CP treatment and this was reduced by treatment with GLY or Mesna. Results are reported as pg Evans blue dye/μg tissue. Bars represent mean±SEM. [Vehicle: n=3; GLY: n=3; CP: n=4; CP+GLY: n=4; CP+Mesna: n=4]. *p<0.05; p<0.01; *p<0.001 by one-way ANOVA and Student-Newman-Keuls post-hoc analysis.

FIGS. 14A-14B are graphs showing that Caspase-1 activity is increased in the hippocampus, not the pons of CP-treated rats. FIG. 14A is a graph showing hippocampus caspase-1 activity in vehicle and CP-treated rats. Results are reported as pg AFC/min/μg protein. Bars represent mean activity ±SEM. FIG. 14B is a graph showing caspase-1 activity in the pons in vehicle and CP-treated rats. Results are reported as pg AFC/min/μg protein. Bars represent mean activity ±SEM. [For both A+B: Vehicle: n=4; CP: n=4]. *p<0.05 by two-tailed Students t-test.

Figures 15A, 15B:
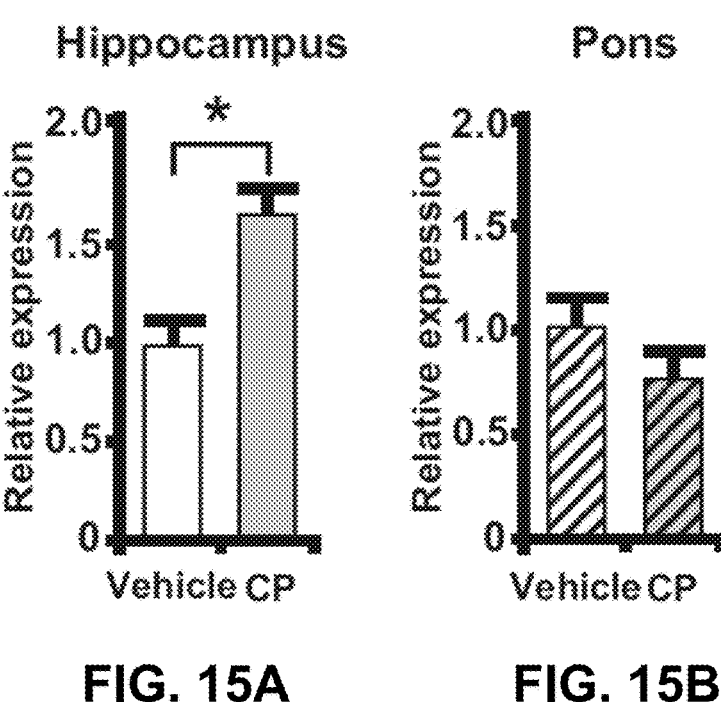
Figures 15C, 15D:
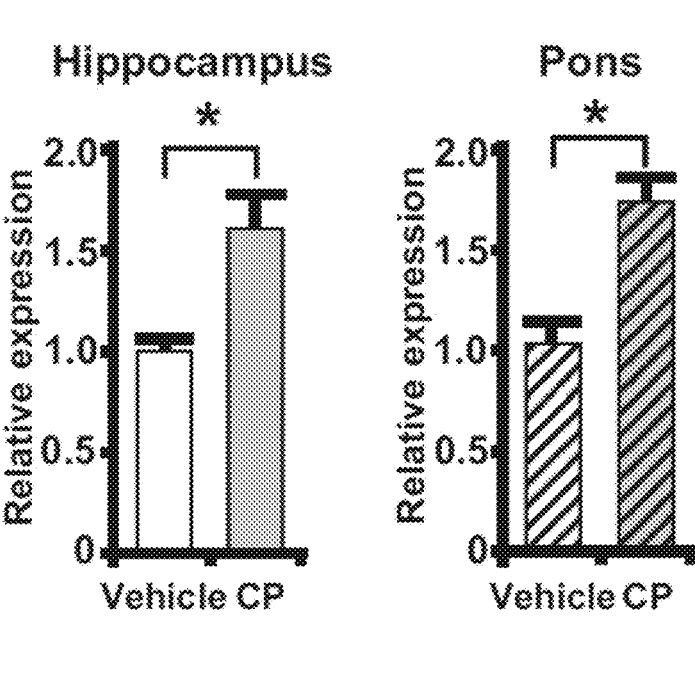
Figures 15E, 15F:
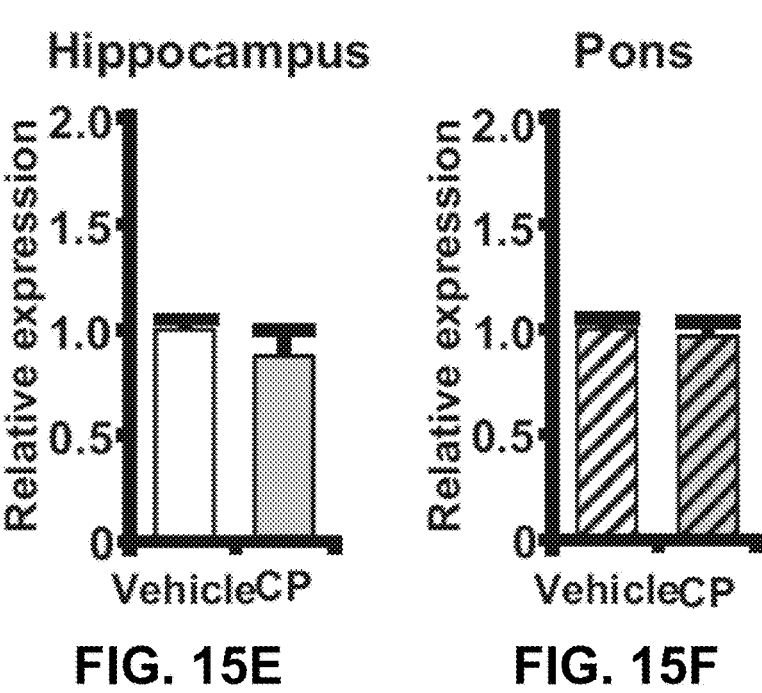
Figures 15G, 15H:
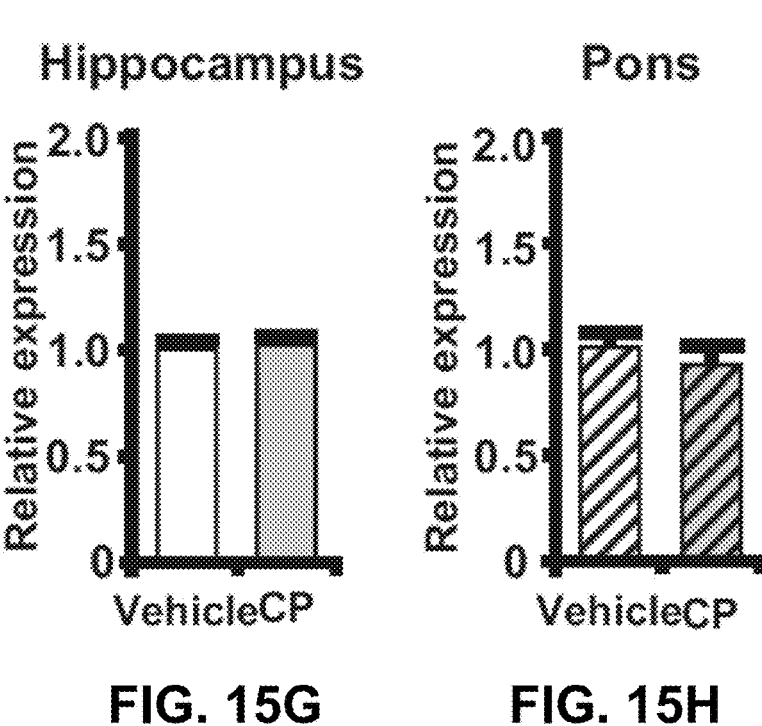

FIGS. 15A-15H are graphs showing that Pro-IL-1β and Pro-IL-18 mRNA expression levels are increased in the hippocampus during CP-induced cystitis. NLRP3 and ASC mRNA expression levels are unchanged in the hippocampus during CP-induced cystitis. Results are expressed as relative expression of the studied genes in treated rats compared to vehicle. Bars represent mean expression levels ±SEM. FIG. 15A is a graph showing Pro-IL-1β levels in the hippocampus [Vehicle: n=13; CP: n=12]. FIG. 15B is a graph showing Pro-IL-1β levels in the pons [Vehicle: n=6; CP: n=6]. FIG. 15C is a graph showing Pro-IL-18 expression levels in the hippocampus [Vehicle: n=8; CP: n=7]. FIG. 15D is a graph showing Pro-IL-18 expression levels in the Pons [Vehicle: n=4; CP n=4]. FIG. 15E is a graph showing NLRP3 levels in the hippocampus [Vehicle: n=9; CP: n=8]. FIG. 15F is a graph showing NLRP3 levels in the pons [Vehicle: n=6; CP: n=6]. FIG. 15G is a graph showing ASC expression levels in the hippocampus [Vehicle: n=9; CP: n=8]. FIG. 15H is a graph showing ASC expression levels in the pons [Vehicle: n=6; CP: n=6]. *p<0.05 by two-tailed Students t-test.

Figure 16A:
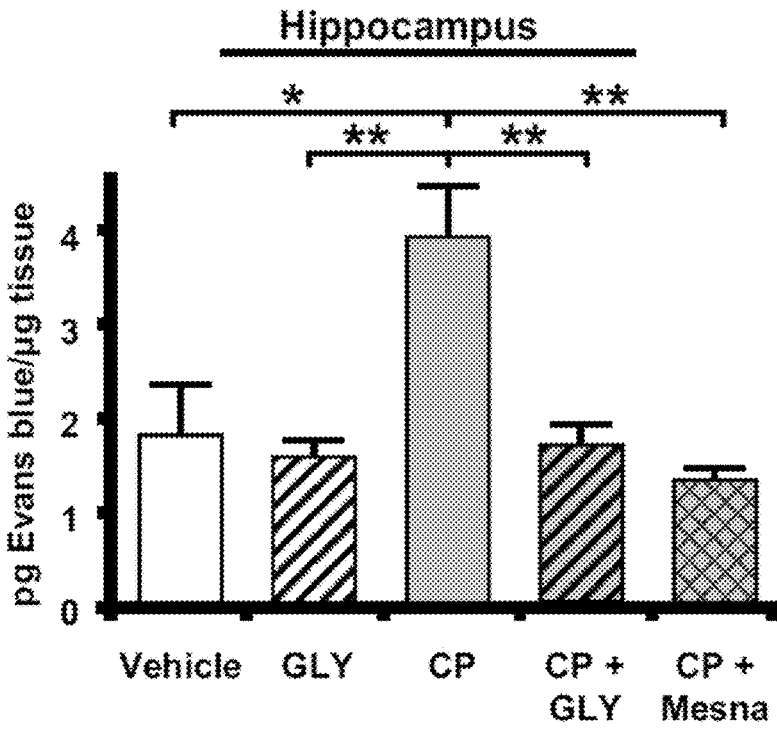
Figure 16B:
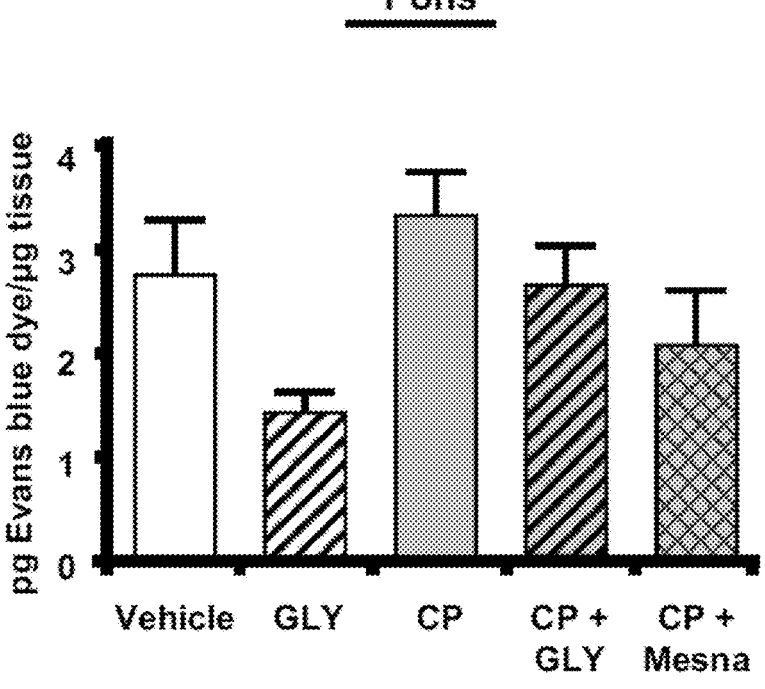
Figure 16C:
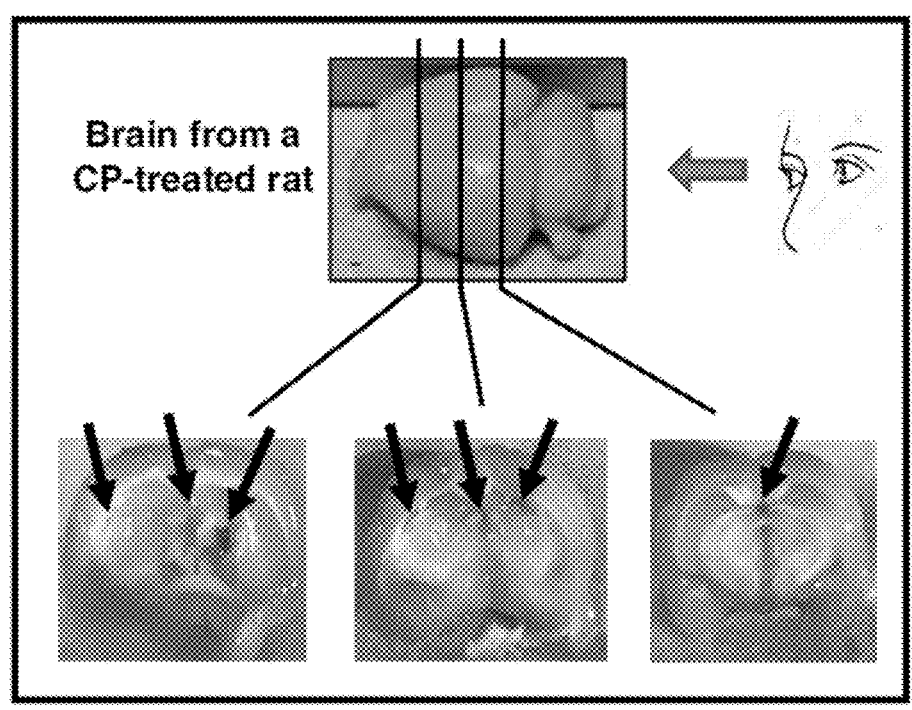
Figure 16D:
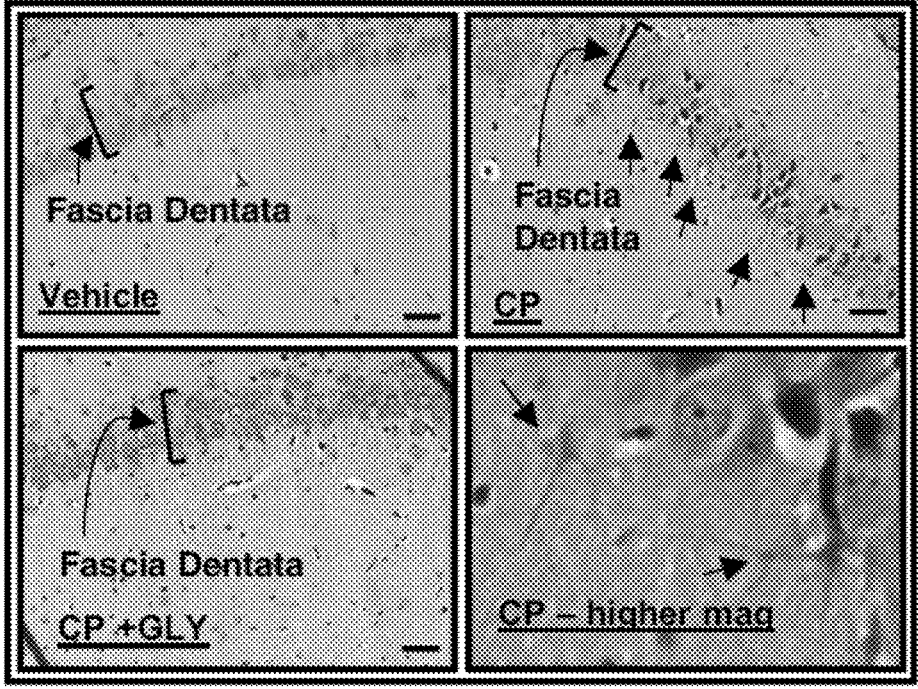
Figure 16E:
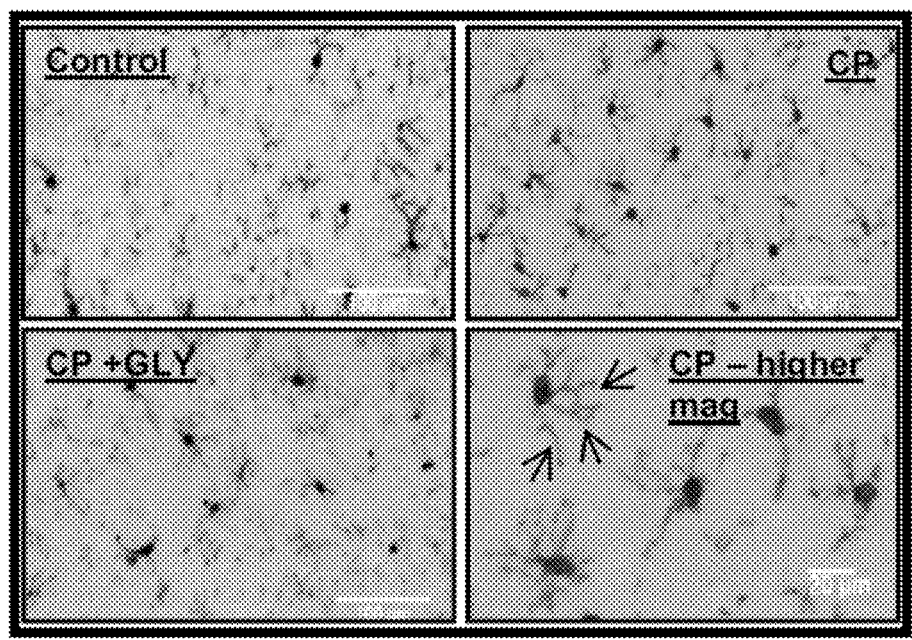
Figure 16F:
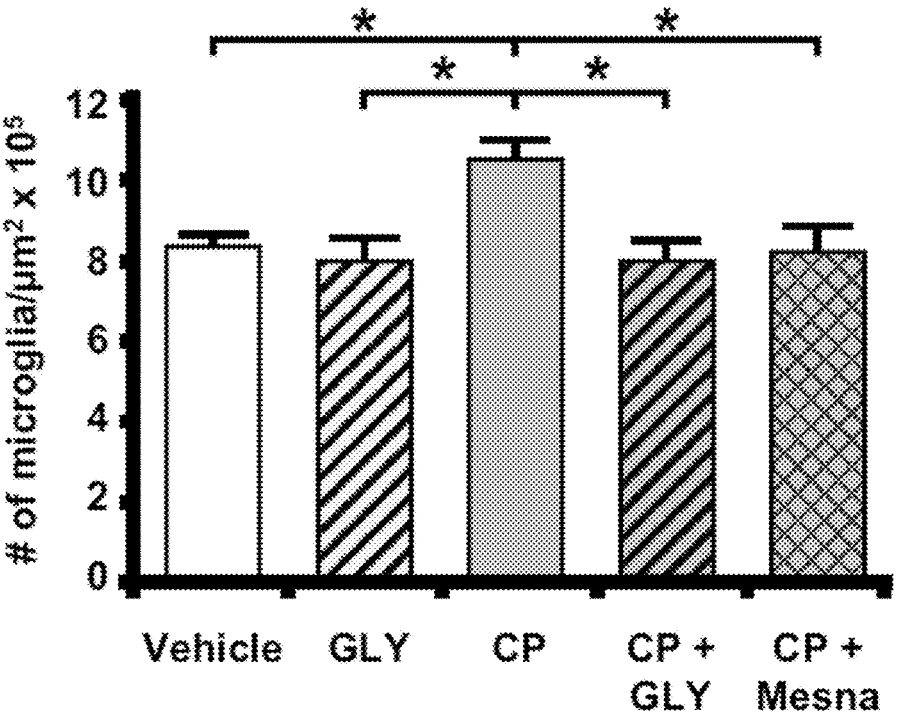

FIGS. 16A-16F show CP-induced cystitis results in inflammation and breakdown of the blood brain barrier in the hippocampus, not in the pons. Administration of GLY or Mesna blocks this effect. FIG. 16A is a graph showing Evans blue extravasation was increased in the Hippocampus by CP. This increase was prevented by treatment with Gly or Mesna. All results were calculated as pg of Evans blue per g of tissue. Bars represent mean±SEM. For A: Vehicle: n=3; GLY: n=3; CP: n=4; CP+GLY: n=4; CP+Mesna: n=4. For B: Vehicle: n=4; GLY: n=3; CP: n=4; CP+GLY: n=4; CP+Mesna: n=8. *p<0.05 by one-way ANOVA and Student-Newman-Keuls post-hoc analysis. FIG. 16B is a graph showing Evans blue extravasation was not significantly changed in the pons by any treatment. FIG. 16C are images showing CP-induced cystitis results in areas of gross blood brain barrier breakdown, with Evans blue dye apparent (arrows) in the periventricular region of the hippocampus. A CP-treated rat was injected with Evans blue as described in the Methods section. After 1 h the brain was removed, sectioned coronally with a scalpel at the approximate locations indicated and photographed. FIG. 16D are microscopy images showing that CP results in an NLRP3-dependent increase in number of microglia-like cells within the fascia dentata of the hippocampus. Coronal sections (10 μm) were cut through the hippocampus and an H&E stain was performed using routine methodical techniques. Slides were visualized at 60×. Activated glial cells are indicated by arrows. FIG. 16E are immunohistochemistry showing increased density of activated microglia within the fascia dentata. Coronal sections (10 μm) were cut and Immunohistochemistry was performed using an anti-IbA1/AIF1 antibody and routine histological methods. Slides were visualized at 20× and the number of microglia was quantitated. Arrows demonstrating increased glial processes (arrows) at higher magnification are shown. FIG. 16F is a graph showing the density of Microglia. Results are depicted as the number of microglia per μm². Bars represent mean±SEM. [Vehicle: n=5; GLY: n=6; CP: n=7; CP+GLY: n=4; CP+Mesna: n=8]. *p<0.05 by one-way ANOVA and Student-Newman-Keuls post-hoc analysis.

Figure 17A:
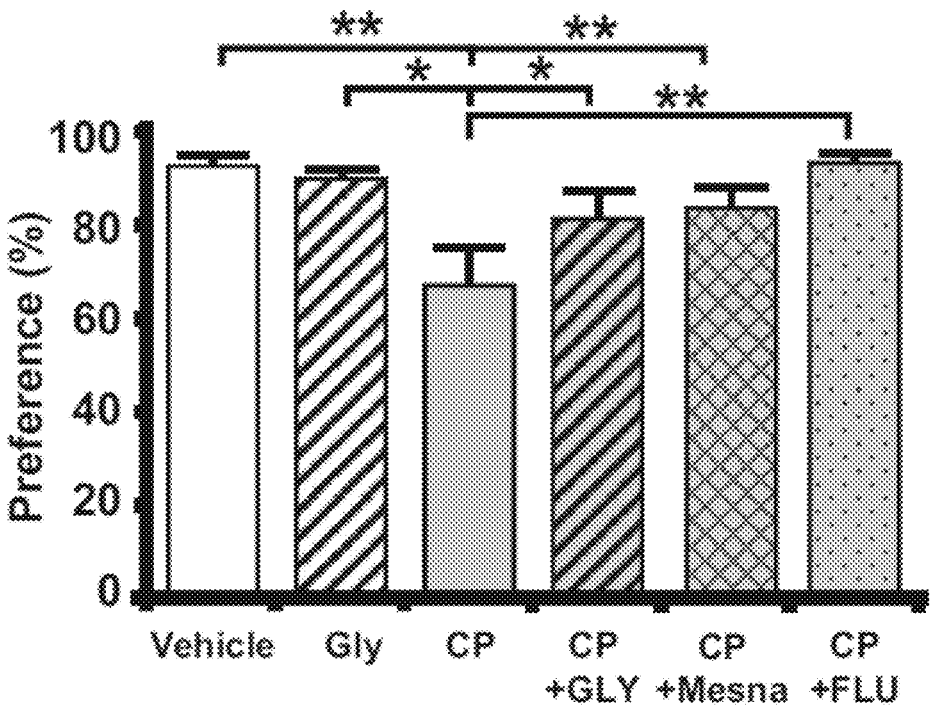
Figure 17B:
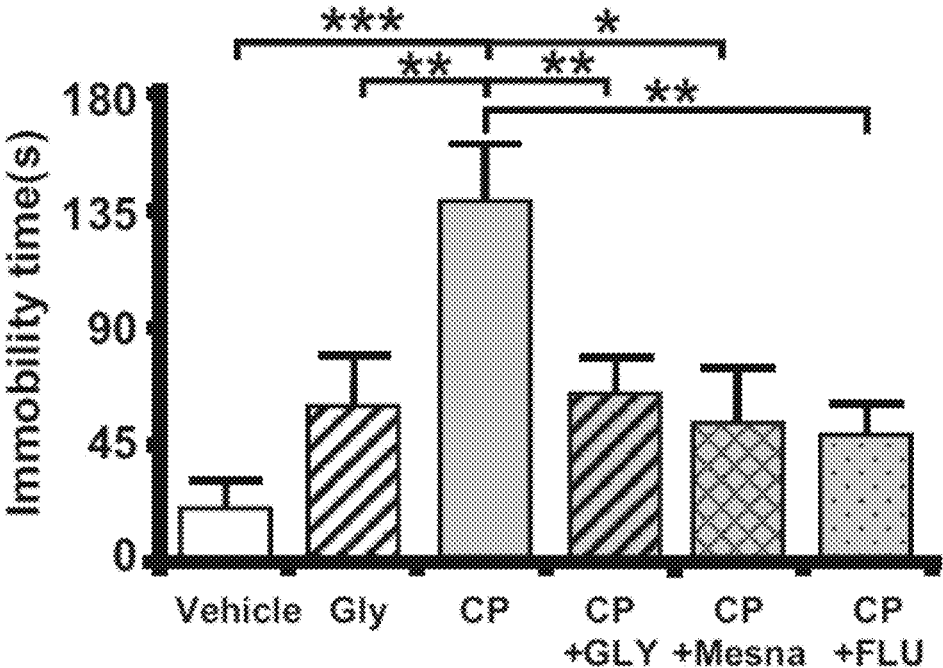

FIGS. 17A-17B are graphs showing CP induces behavioral signs of depression through NLRP3. FIG. 17A is a graph showing the results of the sucrose preference test. A reduction of preference indicates depression. Bars represent the mean±SEM. [Vehicle: n=10; GLY: n=4; CP: n=8; CP+GLY=6; CP+Mesna=12; GP+FLU=8]. *p<0.05 and p<0.01 by one-way ANOVA and Student-Newman-Keuls post-hoc analysis. FIG. 17B** is a graph showing the results of the forced Swim assay. An increase in time spent immobile indicates depression. Bars represent the mean SEM. [Vehicle: n=9; GLY: n=18; CP: n=8; CP+GLY=18; CP+Mesna=6; GP+FLU=11]. *p<0.05 and **p<0.01 by one-way ANOVA and Student-Newman-Keuls post-hoc analysis.

Figure 18:
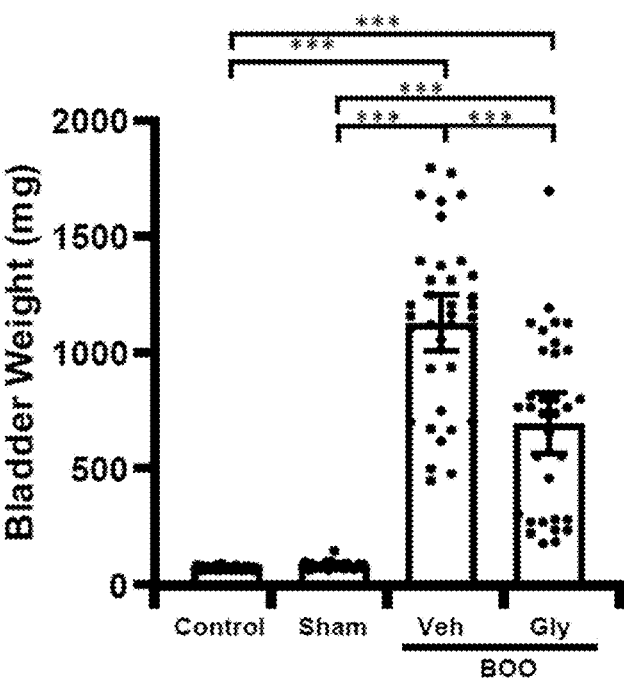

FIG. 18 is a graph showing that bladder weights are greatly increased 12 weeks after BOO and this is partially inhibited by the NLRP3 inhibitor glyburide. Veh=vehicle-treated, Gly=glyburide-treated. Results are the mean±SEM; ***p<0.005 by ANOVA and Student-Newman-Keuls test. (n=45,42,38,35).

Figure 19:
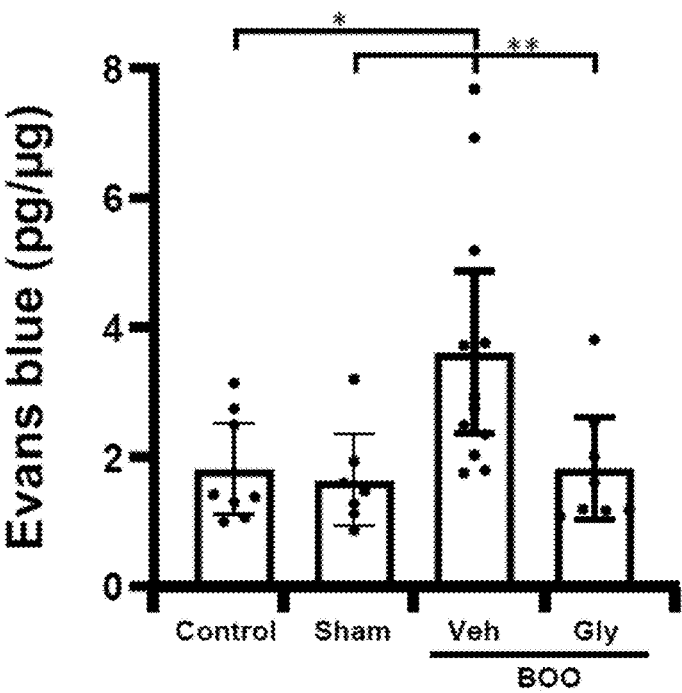

FIG. 19 is a graph showing that after 12 weeks of BOO, inflammation is present in the hippocampus of rats. This inflammation is blocked by concomitant treatment with glyburide. Veh=vehicle-treated, Gly=glyburide-treated. Results are the mean±SEM; *p<0.05, p<0.01, *p<0.005 by ANOVA and Student-Newman-Keuls test. (n=8,7,12,8)

Figure 20:
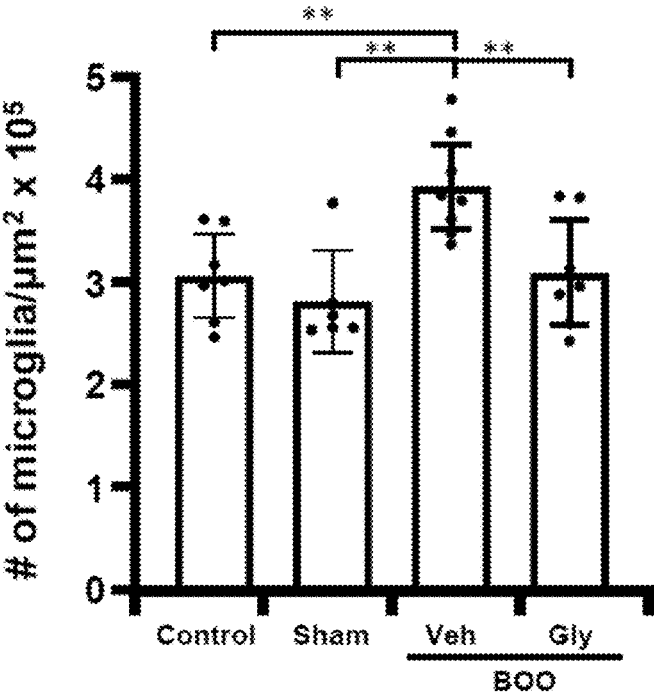

FIG. 20 is a graph showing that after 12 weeks of BOO the number of activated microglia in the hippocampus is increased and this increase was blocked by glyburide treatment. The results are presented as the density of activated microglia per $\mu m^2$. Veh=vehicle-treated, Gly=glyburide-treated. Results are the mean±SEM; **p<0.01 by ANOVA and Student-Newman-Keuls test. (n=7,6,8,7).

Figure 21:
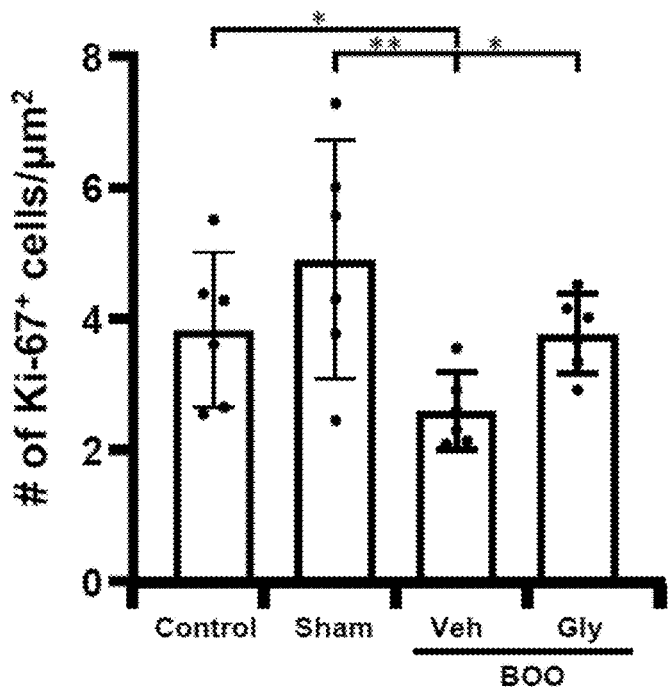

FIG. 21 is a graph showing that after 12 weeks of BOO, neurogenesis is statistically decreased in the hippocampus and this increase is blocked by glyburide treatment. The results are presented as the density of Ki-67$^+$ cells per $\mu m^2$. Veh=vehicle-treated, Gly=glyburide-treated. Results are the mean±SEM; **p<0.01 by ANOVA and Student-Newman-Keuls test. (n=6, 6, 6, 6)

Figure 22A:
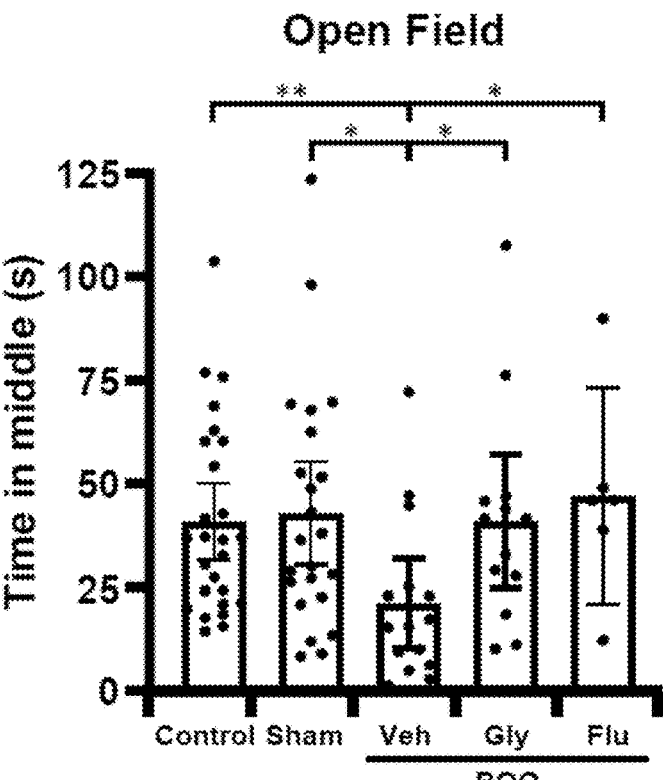
Figure 22B:
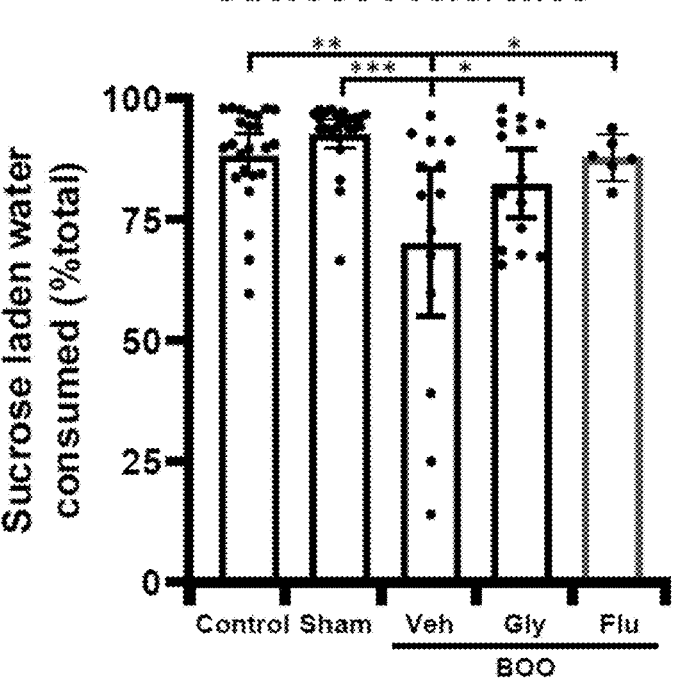

FIGS. 22A-22B are graphs showing that after 12 weeks of BOO, rats show signs of depression. These behavior differences were not present when rats were given glyburide or fluoxetine (Flu), an anti-depressant. FIG. 22A is a graph showing that the open field assay (a measure of anxiety). The results are presented as the time in which at least 2 paws were present in the middle section of the open field during the 10 min test session. Veh=vehicle-treated, Gly=glyburide-treated. Results are the mean±SEM; *p<0.05, p<0.01 by ANOVA and Student-Newman-Keuls test. (n=26, 23, 15, 13, 6). FIG. 22B** is a graph showing that the sucrose preference assay (a measure of anhedonia). The results are presented as the amount of sucrose laden water consumed as a percentage of the total volume imbibed. Veh=vehicle-treated, Gly=glyburide-treated. Results are the mean±SEM; *p<0.05, **p<0.01 by ANOVA and Student-Newman-Keuls test. (n=24, 24, 14, 14, 6).

Figure 23A:
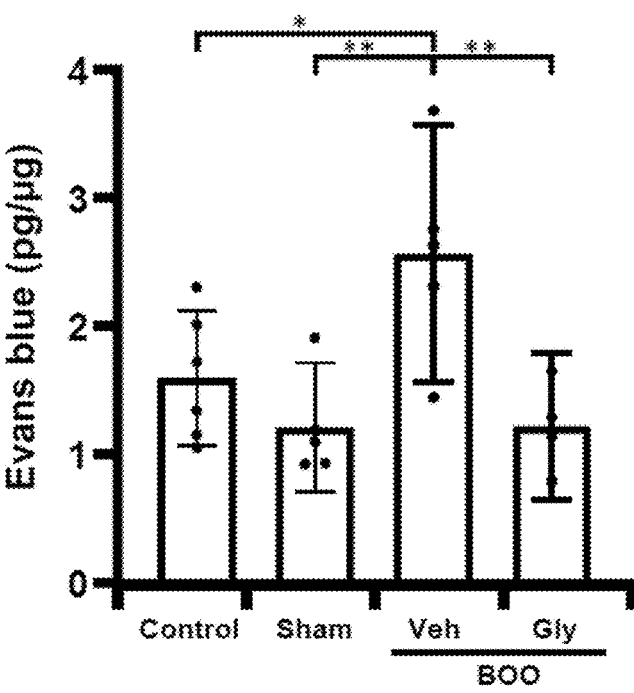
Figure 23B:
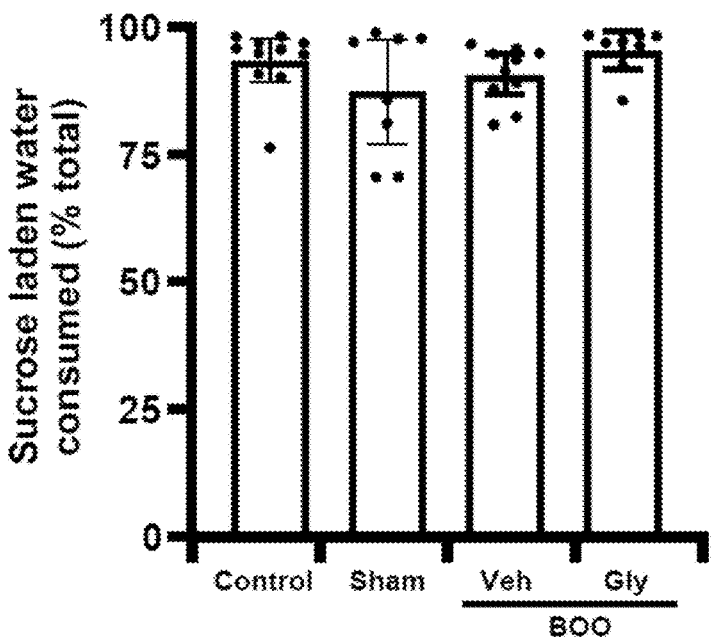

FIGS. 23A-23B are graphs showing that after 6 weeks of BOO, inflammation is present in the hippocampus but there is no change in sucrose preference. FIG. 23A is a graph showing Evan's blue dye extravasation is increased in the hippocampus after 6 weeks of BOO and this increase is blocked by glyburide treatment. Following the treatments indicated, and 6 weeks after BOO or sham surgery, inflammation was assessed by the Evans blue assay. Veh=vehicle-treated, Gly=glyburide-treated. Results are the mean±95% confidence levels; *p<0.05, p<0.01 by ANOVA and Student-Newman-Keuls test. (n=6, 5, 5, 4). FIG. 23B** is a graph showing that there is no change in sucrose preference after 6 weeks of BOO. Animals were treated as indicated and subjected to the sucrose preference assay. Veh=vehicle-treated, Gly=glyburide-treated. Results are the mean±95% confidence levels. (n=11, 8, 10, 8).

DETAILED DESCRIPTION OF THE DISCLOSURE

For the purposes of promoting an understanding of the principles of the present disclosure, reference will now be made to embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Definitions

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human. In certain embodiments, the subject comprises a human having a DAMP-induced or PAMP-induced inflammation of the bladder.

"Administration" as it applies to a human, primate, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

Unless otherwise defined, all technical terms used herein have the same meaning as commonly understood by one of ordinary skill in the art to which this disclosure belongs.

Inhibition of Inflammasomes for the Treatment and Prevention of Inflammation to the Bladder and Central Nervous System The inventors have surprisingly discovered that inflammasomes may serve as therapeutic targets in the treatment of inflammation in urological pathologies. The inventors have discovered inflammasomes are activated early in the development of diabetic bladder dysfunction and can contribute to the onset of voiding dysfunction. Furthermore, the inventors have demonstrated that NLRP3 inflammasome inhibitors can prevent or treat DBD and possibly other diabetic complications. The inventors have also created a new murine model of diabetic mice lacking the NLRP3 inflammasome (NLRP3$^{-/-}$, diab).

Furthermore, the inventors have discovered that the stone components calcium pyrophosphate (CPPD) and monosodium urate (MSU) activate NLRP3 in a reactive oxygen species (ROS) and thioredoxin-interacting protein (TXNIP)-dependent manner in bladder urothelium. These findings demonstrate the importance of ROS and TXNIP, and suggest that targeting either can decrease stone-dependent NLRP3 inflammation within the bladder.

Accordingly, one aspect the present disclosure provides a method of treating or preventing inflammation in the bladder (e.g., cystitis) in a subject in need thereof, comprising administering to the subject a therapeutically effective amount of an inflammasome inhibitor. In another aspect, the present disclosure provides a method of treating or preventing a condition that is associated with or causes inflammation in the bladder in a subject in need thereof, comprising administering to the subject a therapeutically effective amount of an inflammasome inhibitor.

In another aspect, the present disclosure provides a method of treating or preventing diabetic bladder dysfunction (DBD) in a subject in need thereof, comprising administering to the subject a therapeutically effective amount of an inflammasome inhibitor.

Inflammation in the bladder is also known and referred to herein as cystitis. Cystitis can be acute or chronic. Acute cystitis can involve calor, dolor, tumor, rubor (heat, pain, swelling, and redness). Chronic can involve low-level meta-inflammation, does not typically involve calor, dolor, tumor, or rubor, and can contribute to heart disease, cancer, diabetes, stroke, Alzheimer's disease, respiratory disease, among others. Symptoms of cystitis can include a strong, persistent urge to urinate, a burning sensation when urinating, passing frequent, small amounts of urine, passing cloudy urine, passing strong-smelling urine, hematuria (blood in the urine), pelvic discomfort, pressure in the lower abdomen, and/or a low-grade fever.

Inflammation in the bladder (both acute and chronic) can be caused by a variety of different factors and conditions. Inflammation in the bladder can be caused by, for example, bacteria (e.g., a urinary tract infection caused by E. coli), chemotherapy agents (e.g., cyclophosphamide and ifosfamide), exposure to radiation (e.g., radiation treatment to the pelvic area), foreign-bodies (e.g., use of a catheter or a urinary stent), or chemical agents (e.g., chemicals contained in feminine hygiene products, bubble bath, or other chemical that could cause an allergic reaction within the bladder).

Inflammation in the bladder can be caused by benign bladder disorders. The term benign bladder disorder refers to non-cancerous conditions that affect the bladder. Examples of benign bladder disorders include, but are not limited to, infectious cystitis, noninfectious cystitis, reactive proliferative processes, and benign processes that secondarily involve the bladder.

Inflammation in the bladder (both acute and chronic) can also be caused by an inflammatory bladder disorder. The term "inflammatory bladder disorder" refers to a condition that can result in inflammation in the bladder. Examples of "inflammatory bladder disorders" include, but are not limited to, diabetes, kidney stones, urinary stones, enlarged prostate, bladder outlet obstructions (BOO), interstitial cystitis (IC), benign prostatic hyperplasia (BPH), cyclophosphamide-induced hemorrhagic cystitis, diabetic uropathy (e.g., diabetic bladder dysfunction [DBD]), fibrosis, denervation, or pressure activation.

In some embodiments, inflammation in the bladder can be caused by other disorders and diseases including gout, benign prostatic hyperplasia (BPH), gynecological cancers (e.g., cervical cancer, ovarian cancer, uterine cancer, etc.), diabetic nephropathy, diabetic neuropathy, diabetic retinopathy, bladder cancer, pelvic inflammatory disease, endometriosis, Crohn's disease, diverticulitis, lupus, and/or tuberculosis.

Accordingly, the methods of the present disclosure provide for treating and/or preventing conditions associated with inflammation in the bladder, including benign bladder disorders and inflammatory bladder disorders, in a subject by administering to the subject one or more inflammasome inhibitors.

In some embodiments, the inflammation in the bladder is caused by diabetic uropathy. Diabetic uropathy refers to a number of debilitating urologic complications. Types of diabetic uropathy include, but are not limited to, DBD, urinary incontinence, urinary tract infection and sexual dysfunction.

DBD is the most common complication seen in diabetic patients. DBD is a progressive complication. DBD can be either acute of chronic. Symptoms of acute DBD (or early stage) can include irritative voiding symptoms, including urgency (e.g., overactive bladder), frequency, nocturia, precipitancy, and urge incontinence. Symptoms of chronic (or late stage) DBD can include decompensated bladder (e.g., insensate bladder, poor compliance, and overflow incontinence) and detrusor underactivity (DU) (also known as underactive bladder).

In some embodiments of the above aspects, the inflammation in the bladder comprises urothelial cell damage. In certain embodiments of the above aspects, the inflammation in the bladder comprises urothelial cell inflammation. In other embodiments, bladder damage from a condition associated with inflammation in the bladder (e.g., diabetes) can cause neuropathy, smooth muscle dysfunction, and urothelial (barrier) dysfunction.

Inflammation in the bladder can be caused by activation of an inflammasome. In some embodiments of the above aspects, the inflammasome can be activated by danger associated molecule patterns (DAMPs) or pathogen associated molecular patterns (PAMPs).

DAMPs are endogenous danger molecules that are released from damaged or dying cells and activate the innate immune system by interacting with pattern recognition receptors (PRRs). DAMPs can promote pathological inflammatory responses. DAMPs can promote the formation of a multimeric structure known as the inflammasome in macrophages and other cells, including urothelia and microglia. The molecule responsible for the DAMPs-induced inflammation in the bladder can be any molecule known to damage bladder or tissue and/or cells, including urothelial cells, or any combination thereof. Examples of DAMPs include, but are not limited to, extracellular ATP, components of urinary stones, such as calcium pyrophosphate (CPPD), monosodium urate (MSU), and calcium oxalate, high mobility group box-1 (HMG-B1), albumin, uromodulin, uric acid crystals, hypoxia, acrolein, calcium oxalate, cholesterol, reactive oxidative species (ROS) serum amyloid A (SAA), amyloid β fibril, hyaluronan, aluminum, asbestos, silica, UV radiation, drusen, or skin irritants. DAMPs can also include diabetic metabolites (e.g., uric acid, glucose, MSU, HMGB1, AGE, or lipids), ROS from mitochondrial dysfunction, or K+ cellular efflux.

PAMPs, on the other hand, can initiate and perpetuate the infectious pathogen-induced inflammatory response. The pathogen responsible for the PAMPs-induced inflammation in the bladder can be any pathogen known to damage bladder tissue and/or cells, including urothelial cells, smooth muscle cells, or any combination thereof. PAMPs can be a fungus (e.g., *Candida albicans, Saccharomyces cerevisiae,* or *Aspergillus fumigatus*), bacteria (e.g., *Listeria monocytogenes, Staphylococcus aureus, Escherichia coli, Chlamydia pneumonia, Mycobacterium tuberculosis, Clostridium difficile, Bordetella pertussis, Vibrio cholera, Neisseria gonorrhoeae,* or *Streptococcus pyogenes*), or a virus (e.g., Influenza A, adenovirus, Sendai virus, Varicella-zoster, or herpes). In some embodiments, PAMPs can include lipopolysaccharide (LPS) from the outer membrane of the Gram-negative cell wall, bacterial flagellin, muramyl dipeptide, which can be a constituent of both Gram-positive and Gram-negative bacteria, alpha-hemolysin, lipoteichoic acid, or viral DNA/RNA.

As the inventors have demonstrated, inflammation in the bladder can cause secondary inflammation in the central nervous system (e.g., in the hippocampus), which can cause psychosocial maladies. In particular, the inventors have discovered a link between benign bladder disorders and mood disorders. In particular, the inventors found that cyclophosphamide (CP)-induced hemorrhagic cystitis causes NLRP3-dependent hippocampal inflammation leading to depression symptoms in rats. The inventors found that CP triggered an increase in inflammasome activity (caspase-1 activity) in the hippocampus but not in the pons.

The inventors have also discovered that bladder outlet obstruction (BOO), a bladder-localized event, stimulates NLRP3-dependent inflammation in the rat hippocampus after 12 weeks and this inflammation can cause depressive behavior. This is the first mechanistic explanation of the link between BOO and depression and provides evidence for a distinct bladder-brain axis.

Thus, yet another aspect of the present disclosure provides a method of treating or preventing a condition associated with neuroinflammation, the method comprising administering a therapeutically effective amount of an inflammasome inhibitor. In some embodiments, the subject suffering from neuroinflammation (or at risk for suffering from neuroinflammation) has been diagnosed with inflammation in the bladder or an inflammatory bladder disorder.

In some embodiments, a condition associated with neuroinflammation can be a mood disorder in a subject. Mood disorders include, but are not limited to, depression, dysthymic disorder, bipolar disorder, anxiety, anhedonia, obsessive-compulsive disorder, panic disorder, bulimia, attention deficit hyperactivity disorder (ADHD), narcolepsy, social phobia, or post-traumatic stress disorder. In some embodiments, the mood disorder is depression, anxiety, or anhedonia.

In other embodiments, a patient's bladder inflammation and neuroinflammation can both be treated and/or prevented concurrently by administering an inflammasome inhibitor.

In some embodiments, the above methods further comprise administering a therapeutically effective amount of an antidepressant agent. In some embodiments, the antidepressant agent can be administered concurrently with, prior to, or subsequent to an inflammasome inhibitor.

The antidepressant agent can be a selective serotonin reuptake inhibitors (SSRIs), a norepinephrine-dopamine reuptake inhibitors (NDRIs), or a monoamine oxidase inhibitors (MAOIs).

SSRIs can include, but are not limited to, citalopram, escitalopram, fluoxetine, fluvoxamine, paroxetine, and sertraline. In some embodiments, the antidepressant agent is fluoxetine.

NDRIs can include, but are not limited to, Amineptine, Bupropion, Desoxypipradrol, Dexmethylphenidate, Difemetorex, Diphenylprolinol, Ethylphenidate, Fencamfamine, Fencamine, Lefetamine, Methylenedioxypyrovalerone, Methylphenidate, Nomifensine, 0-2172, Phenylpiracetam, Pipradrol, Prolintane, Pyrovalerone, Solriamfetol, Tametraline, or WY-46824.

MAOIs can include, but are not limited to, Isocarboxazid, Nialamide, Phenelzine, Hydracarbazine, Tranylcypromine, Bifemelane, Moclobemide, Pirlindole, Toloxatone, Rasagiline, Selegiline, or Safinamide.

In certain embodiments, the subject is a mammal. In some embodiments, the mammal is a human.

Inflammasome Inhibitors

Inflammasomes are cytosolic multiprotein oligomers of the innate immune system responsible for the activation of inflammatory responses. Inflammasomes can include the NLR-class of inflammasomes, such as NLRP1, NLRP3, NLRP6, NLRP7, NLRP12, and NLRC4 (IPAF), as well as interferon-inducible protein AIM2 (AIM2). The NLR-class of inflammasomes each have a nucleotide-binding oligomerization domain (NOD), which is bound by ribonucleotide-phosphates (rNTP) and can facilitate self-oligomerization as well as a C-terminal leucine-rich repeat (LRR), which serves as a ligand-recognition domain for other receptors (e.g. TLR) or microbial ligands. The result of any inflammasome activation is the activation of the protease caspase-1. Caspase-1 cleaves pro-IL-1β and pro-IL-18 into their active forms, which then precipitate a wider inflammatory reaction. Multiple inflammasomes are present in the bladder, including but not limited to, the NLRP1 inflammasome, the NLRP3 inflammasome, the NLRP6 inflammasome, the NLRP7 inflammasome, the NLRP12 inflammasome, the NLRC4 inflammasome, and the AIM2 inflammasome. Multiple inflammasomes are present in the brain and spinal cord, including but not limited to, the NLRP1 inflammasome, the NLRP3 inflammasome, and the NLRC4 inflammasome.

The term "NLRP1" refers to a gene that encodes NACHT, LRR, FUND, CARD domain and PYD domains-containing protein 1. NLRP1 can be activated by PAMPS.

The term "NLRP3" refers to NOD-like receptor family, pyrin domain containing 3 inflammasome or NACHT, LRR and PYD domains-containing protein 3 (NALP3), also known as cryopyrin, cold induced autoinflammatory syndrome 1 (CIAS1), caterpiller-like receptor 1.1 (CLR1.1) or Pyrin Domain-Containing Apaf1-Like Protein 1 (PYPAF1). NLRP3 is a component of a multiprotein oligomer consisting of the NLRP3 protein, a structural co-factor protein called thioredoxin-interacting protein (TXNIP), ASC (apoptosis-associated speck-like protein containing a CARD) and pro-caspase 1. NLRP3 is involved in inflammation and the immune response. In the presence of activating stimuli, this complex forms, recruits, and activates caspase-1, resulting in the cleavage and maturation of the pro-inflammatory cytokines IL-1β and IL-18. These cytokines are released from the cell via a form of necrotic cell death called pyroptosis, where they go on to promote inflammation.

NLRP3 can respond to both PAMPs and DAMPs.

It would be understood from context in some instances that the NLRP1 inflammasome, the NLRP3 inflammasome, the NLRP6 inflammasome, the NLRP7 inflammasome, the NLRP12 inflammasome, the NLRC4 inflammasome, and the AIM2 inflammasome. Multiple inflammasomes are present in the brain and spinal cord, including but not limited to, the NLRP1 inflammasome, the NLRP3 inflammasome, and the NLRC4 inflammasome are referred to herein as NLRP1, NLRP3, NLRP6, NLRP7, NLRP12, NLRC4, and AIM2.

The term "NLRP6" refers to NOD-like receptor family pyrin domain containing 6, is an intracellular protein that plays a role in the immune system. It is also known as NALP6, PYPAF5, PAN3, and CLR11.4, and is one of 14 pyrin domain containing members of the NOD-like receptor family of pattern recognition receptors. NLRP6 role in immunity is related to its ability to regulate caspase-1 and NF-κB activity.

The term "NLRP7" refers to NACHT, LRR and PYD domains-containing protein 7.

The term "NLRP12" refers to NACHT, LRR and PYD domains-containing protein 12.

The term "NLRC4" refers to NLR family CARD domain-containing protein 4. The NLRC4 protein is highly conserved across mammalian species.

The term "AIM2" refers to interferon-inducible protein AIM2.

As used herein, "inflammasome inhibitor" refers to any compound capable of inhibiting the expression and/or function of inflammasomes (e.g., the NLR3 inflammasome), in a cell, including inhibiting the expression and/or function of the proteins in the NLRP3/IL-1β pathway. The term "inflammasome inhibitor" is meant to include one or more compounds capable of inhibiting the expression and/or function, i.e. the term may include two or more inhibitors that may be used in combination, including sequential or concomitant administration. The inflammasome inhibitors as used with the present invention may be inflammasome specific inhibitors. The inflammasome inhibitors may be allosteric inhibitors.

Inflammasome inhibitors can include, but are not limited to, an NLRP1 inflammasome inhibitor, an NLRP3 inflammasome inhibitor, an NLRP6 inflammasome inhibitor, an NLRP7 inflammasome inhibitor, an NLRP12 inflammasome inhibitor, an NLRC4 inflammasome inhibitor, and/or an AIM2 inflammasome inhibitor.

Inflammasome inhibitors can also include compounds or a combination of compounds that inhibit the expression and/or function of the proteins in the NLRP3/IL-1β pathway. Inhibitors of proteins in the NLRP3/IL-1β pathway include, but are not limited to, NLRP3 inflammasome inhibitors, TXNIP inhibitors, ASC inhibitors, NEK7 inhibitors, Gasdermin D inhibitors, capspase-11 inhibitors, capsase-1 inhibitors, IL-1β inhibitors, IL-18 inhibitors and combinations thereof and pharmaceutical compositions thereof.

In some embodiments, the NLRP3 inflammasome inhibitor is a sufonylurea drug such as glyburide or functionally equivalent derivatives thereof, for example, glyburide precursors or derivatives that lack the cyclohexylurea moiety, or functionally equivalent precursors or derivatives that contain the sulfonyl and benamido groups. Examples include 5-chloro-2-methoxy-N-[2-(4-sulfamoylphenyl)-ethyl]-benzamide and 1-[(4-methylbenzene)sulfonyl]-1H-1,3-benzodiazol-2-amine. Functionally equivalent precursors or derivatives of glyburide include precursors or derivatives that retain the activity of glyburide, at least in part, to inhibit or reduce the activity of NLRP3 inflammasome, e.g. that retain at least about 25% of the activity of glyburide, about 50% of the activity of glyburide, or about 70%, 80%, or 90% of the activity of glyburide.

In some embodiments, the NLRP3 inflammasome inhibitor is glyburide, 2-mercaptoethane sulfonate sodium (Mesna), CY09, MCC950, 3,4-Methylenedioxy-β-nitrostyrene (MNS), Tranilast (N-[3',4'-dimethoxycinnamoyl]-anthranilic acid, TR), OLT1177, Oridonin, 16673-34-0, JC124, FC11A-2, parthenolide, Z-VAD-FMK, Bay 11-7082, aloe vera, curcumin, artesunate, dapansutrile, glybenclamide, Epigallocatechin-3-gallate (EGCG), Genipin, red ginseng extract (RGE), isoliquiritigenin (ILG), NBC 6, NBC 19 INF 39, OXSI 2, (R)-Shikonin, INF 4E, CRID3 sodium salt, Mangiferin, propolis, quercetin, resveratrol, or Sulforaphane (SFN), or combinations thereof.

In some embodiments, the inflammasome inhibitor is a caspase-1 inhibitor. The caspase-1 inhibitor can be a direct inhibitor of caspase-1 enzymatic activity. Alternatively, the caspase-1 inhibitor can be an indirect inhibitor that inhibits initiation of inflammasome assembly or inflammasome signal propagation. Examples of caspase-1 inhibitors can be antioxidants, including reactive oxygen species (ROS) inhibitors. Examples of caspase-1 inhibitors include, but are not limited to, flavonoids including flavones such as apigenin, luteolin, and diosmin; flavonols such as myricetin, fisetin and quercetin; flavanols and polymers thereof such as catechin, gallocatechin, epicatechin, epigallocatechin, epigallocatechin-3-gallate and theaflavin; isoflavone phytoestrogens; and stilbenoids such as resveratrol. Also included are phenolic acids and their esters such as gallic acid and salicyclic acid; terpenoids or isoprenoids such as andrographolide and parthenolide; vitamins such as vitamins A, C and E; vitamin cofactors such as co-enzyme Q10, manganese and iodide, other organic antioxidants such as citric acid, oxalic acid, phytic acid and alpha-lipoic acid, and *Rhus verniciflua* stokes extract. The caspase-1 inhibitor may be a combination of these compounds, for example, a combination of a-lipoic acid, co-enzyme Q10 and vitamin E, or a combination of a caspase 1 inhibitor(s) with another inflammasome inhibitor such as glyburide or a functionally equivalent precursor or derivative thereof.

The caspase-1 inhibitor can be a small molecule inhibitor, including cyanopropanate-containing molecules, such as (S)-3-((S)-1-((S)-2-(4-amino-3-chlorobenzamido)-3,3-dimethylbutanoyl)pyrrolidine-2-carboxamido)-3-cyano-propanoic acid, as well as other small molecule caspase-1 inhibitors such as (S)-1-((S)-2-{[1-(4-amino-3-chloro-phenyl)-methanoyl]-amino}-3,3-dimethyl-butanoyl)-pyrrolidine-2-carboxylic acid ((2R,3 S)-2-ethoxy-5-oxo-tetrahydro-furan-3-yl)-amide. Such inhibitors can be chemically synthesized.

In some embodiments, the caspase-1 inhibitor can be Ac-YVAD-cmk, parthenolide, INF 4E, or VX-765.

In some embodiments, the inflammasome inhibitor can be a reactive oxygen species (ROS) scavenger, such as N-acetylcysteine (NAC) or mannitol.

In some embodiments, the inflammasome inhibitor can be a TXNIP inhibitor, such as a calcium channel blocker (e.g., amlodipine, diltiazem, felodipine, isradipine, nicardipine, nifedipine, nisoldipine, or verapamil).

In some embodiments, the inflammasome inhibitor can be an IL-1β inhibitor, such as Anakinra (Kineret), rilonacept, or canakinumab.

In some embodiments, the inflammasome inhibitor can be an ASC inhibitor, such as IC 100.

In some embodiments, the inflammasome inhibitor can be a NEK7 inhibitor, such as Oridonin (Ori).

In some embodiments, the inflammasome inhibitor can be a Gasdermin D inhibitor, such as N-acetyl-Phe-Leu-Thr-Asp-chloromethylketone (Ac-FLTD-CMK).

In some embodiments, the inflammasome inhibitor can be a capspase-11 inhibitor. Examples of a caspase-11 inhibitor include, but are not limited to, wedelolactone, NleF, VX-765.

Inflammasome inhibitors can be small molecules, naturally occurring molecules (flavones, flavonoids, etc.), an interfering oligonucleotides, or an immunological inhibitor (e.g., a monoclonal antibody).

As used herein, "an interfering oligonucleotide" refers to any oligonucleotide that interferes with, i.e. reduces, inhibits, or eliminates, the expression of an inflammasome (e.g., the NLR3 inflammasome). Interfering oligonucleotides include aptamers and other oligonucleotide molecules as described herein.

Also contemplated by the present disclosure are other types of inhibitors of inflammasomes, including inhibitors of the NLRP3/IL-1β pathway, including but not limited to, the following:

i. Aptamers

Aptamers, also called nucleic acid ligands, are nucleic acid molecules characterized by the ability to bind to a target molecule with high specificity and high affinity. Almost every aptamer identified to date is a non-naturally occurring molecule.

Aptamers to a given target (e.g. an inflammasome may be identified and/or produced by the method of Systematic Evolution of Ligands by EXponential enrichment (SELEX™). Aptamers and SELEX are described in Tuerk and Gold (Systematic evolution of ligands by exponential enrichment: RNA ligands to bacteriophage T4 DNA polymerase. Science. 1990 Aug. 3; 249(4968):505-10) and in WO91/19813.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesized by methods which are well known to the skilled person. For example, aptamers may be chemically synthesized, e.g. on a solid support.

Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer.

Aptamers can be thought of as the nucleic acid equivalent of monoclonal antibodies and often have $K_d$'s in the nM or pM range, e.g. less than one of 500 nM, 100 nM, 50 nM, 10 nM, 1 nM, 500 pM, 100 pM. As with monoclonal antibodies, they can be useful in virtually any situation in which target binding is required, including use in therapeutic and diagnostic applications, in vitro or in vivo. In vitro diagnostic applications can include use in detecting the presence or absence of a target molecule.

Aptamers according to the present disclosure can be provided in purified or isolated form. Aptamers according to the present disclosure may be formulated as a pharmaceutical composition or medicament.

Suitable aptamers can optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

Suitable aptamers can optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Suitable aptamers can optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

ii. Oligonucleotide Repression of Inflammasome Expression

Oligonucleotide molecules, particularly RNA, can be employed to regulate gene expression (e.g, expression of the NLRP1 gene, the NLRP3 gene, the NLRP6 gene, the NLRP7 gene, the NLRP12 gene, the NLRC4 gene, the AIM2 gene, the ASC gene, the caspas-1 gene, and/or the TXNIP gene). These include antisense oligonucleotides, targeted degradation of mRNAs by small interfering RNAs (siRNAs), small molecules, post transcriptional gene silencing (PTGs), developmentally regulated sequence-specific translational repression of mRNA by micro-RNAs (miR-NAs) and targeted transcriptional gene silencing.

An antisense oligonucleotide is an oligonucleotide, preferably single stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for inflammasomes, oligonucleotides can be designed to repress or silence the expression of inflammasome s (e.g., those regulated by the NLR-class genes). Such oligonucleotides can have any length, but can be short, e.g. less than 100 nucleotides, e.g. 10-40 nucleotides, or 20-50 nucleotides, and can comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the inflammasome mRNA (e.g., the NLRP3 inflammasome mRNA). The complementary region of the nucleotide sequence can have any length, but is preferably at least 5, and optionally no more than 50, nucleotides long, e.g. one of 6, 7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of inflammasome expression (e.g., NLRP3 inflammasome expression) will preferably result in a decrease in the quantity of inflammasome expressed by a cell. For example, in a given cell the repression of an inflammasome by administration of a suitable nucleic acid will result in a decrease in the quantity of inflammasome expressed by that cell relative to an untreated cell. Repression can be partial. Preferred degrees of repression are at least 50%, more preferably one of at least 60%, 70%, 80%, 85% or 90%. A level of repression between 90% and 100% is considered a "silencing" of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (Nature 2009 Jan. 22; 457(7228):426-433).

In the art, these RNA sequences are termed "short or small interfering RNAs" (siRNAs) or "microRNAs" (miRNAs) depending on their origin. Both types of sequence may be used to downregulate gene expression by binding to complementary RNAs and either triggering mRNA elimination (RNAi) or arresting mRNA translation into protein. siRNAs are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

Accordingly, the present disclosure provides the use of oligonucleotide sequences for down-regulating the expression of inflammasomes.

siRNA ligands are typically double stranded and, in order to optimize the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, PLoS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs can be processed in the cell to produce siRNAs. The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP.

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. The shRNA can be produced endogenously (within a cell) by transcription from a vector. shRNAs can be produced within a cell by transfecting the cell with a vector encoding the shRNA sequence under control of a RNA polymerase III promoter such as the human H1 or 7SK promoter or a RNA polymerase II promoter. Alternatively, the shRNA can be synthesized exogenously (in vitro) by transcription from a vector. The shRNA can then be introduced directly into the cell. The shRNA molecule can comprise a partial sequence of the inflammasome. The shRNA sequence can be between 40 and 100 bases in length. The stem of the hairpin can be between 19 and 30 base pairs in length. The stem can contain G-U pairings to stabilize the hairpin structure.

siRNA molecules, longer dsRNA molecules or miRNA molecules can be made recombinantly by transcription of a nucleic acid sequence, preferably contained within a vector. The siRNA molecule, longer dsRNA molecule or miRNA molecule can comprise a partial sequence of the inflammasome.

In one embodiment, the siRNA, longer dsRNA or miRNA is produced endogenously (within a cell) by transcription from a vector. The vector can be introduced into the cell in any of the ways known in the art. Optionally, expression of the RNA sequence can be regulated using a tissue specific (e.g. heart, liver, kidney, brain, bladder, or eye specific) promoter. In a further embodiment, the siRNA, longer dsRNA or miRNA is produced exogenously (in vitro) by transcription from a vector.

Suitable vectors can be oligonucleotide vectors configured to express the oligonucleotide agent capable of inflammasome repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" can include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long-term expression of the therapeutic oligonucleotide. Examples include lentiviral, adenovirus, and retroviruses.

In other embodiments a vector can be configured to assist delivery of the therapeutic oligonucleotide to the site at which repression of inflammasome expression is required. Such vectors typically involve complexing the oligonucleotide with a positively charged vector (e.g., cationic cell penetrating peptides, cationic polymers and dendrimers, and cationic lipids); conjugating the oligonucleotide with small molecules (e.g., cholesterol, bile acids, and lipids), polymers, antibodies, and RNAs; or encapsulating the oligonucleotide in nanoparticulate formulations.

In one embodiment, a vector can comprise a nucleic acid sequence in both the sense and antisense orientation, such that when expressed as RNA the sense and antisense sections will associate to form a double stranded RNA.

Alternatively, siRNA molecules can be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Modified nucleotide bases can be used in addition to the naturally occurring bases, and may confer advantageous properties on siRNA molecules containing them.

For example, modified bases can increase the stability of the siRNA molecule, thereby reducing the amount required for silencing. The provision of modified bases can also provide siRNA molecules which are more, or less, stable than unmodified siRNA.

The term "modified nucleotide base" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methyl-thio-N6-isopentenyladenine, uracil-5-oxyacetic acid methyl ester, psueouracil, 2-thiocytosine, 5-methyl-2 thiouracil, 2-thiouracil, 4-thiouracil, 5methyluracil, N-uracil-5-oxy-acetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6,diaminopurine, methylpsuedouracil, 1-methylguanine, 1-methylcytosine.

Methods relating to the use of RNAi to silence genes in *C. elegans, Drosophila*, plants, and mammals are known in the art.

Accordingly, the present disclosure provides a nucleic acid that is capable, when suitably introduced into or expressed within a mammalian, e.g. human, cell that otherwise expresses inflammasome(s) or NLRP3/IL-β pathway proteins, of suppressing inflammasome expression or expression of NLRP3/IL-β pathway proteins by RNAi.

The nucleic acid may have substantial sequence identity to a portion of the inflammasome mRNA, or the complementary sequence to said mRNA.

The nucleic acid may be a double-stranded siRNA. As the skilled person will appreciate, and as explained further below, a siRNA molecule may include a short 3' DNA sequence also.

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridize with each other. In a mammalian cell, the hairpin structure may be cleaved from the molecule by the enzyme DICER, to yield two distinct, but hybridized, RNA molecules.

Only single-stranded (i.e. non self-hybridized) regions of an mRNA transcript are expected to be suitable targets for RNAi. It is therefore proposed that other sequences very close in the inflammasome mRNA transcript can also be suitable targets for RNAi.

Accordingly, the present disclosure provides nucleic acids that are capable, when suitably introduced into or expressed within a mammalian cell that otherwise expresses inflammasome(s), of suppressing inflammasome expression by RNAi, wherein the nucleic acid is generally targeted to the sequence of, or portion thereof, of the inflammasome.

By "generally targeted" the nucleic acid can target a sequence that overlaps with the inflammasome or is in the pathway activated by the inflammasome that causes inflammation. In particular, the nucleic acid can target a sequence in the mRNA of a human inflammasome that is slightly longer or shorter than one of an inflammasome, but is otherwise identical to the native form.

It is expected that perfect identity/complementarity between the nucleic acid of the invention and the target sequence, although preferred, is not essential. Accordingly, the nucleic acid of the invention can include a single mismatch compared to the mRNA of the inflammasome. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences for the inflammasome.

However, it is also expected that slightly shorter or longer sequences directed to the same region of the inflammasome mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands. For this reason, DNA dinucleotides may be preferred.

When present, the dinucleotide overhangs can be symmetrical to each other, though this is not essential. Indeed, the 3' overhang of the sense (upper) strand is irrelevant for RNAi activity, as it does not participate in mRNA recognition and degradation.

Any dinucleotide overhang can therefore be used in the antisense strand of the siRNA. Nevertheless, the dinucleotide is preferably —UU or -UG (or -TT or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). The dinucleotides AA, CC and GG can also be used, but are less effective and consequently less preferred.

Moreover, the 3' overhangs can be omitted entirely from the siRNA.

The present disclosure also provides single-stranded nucleic acids (herein referred to as single-stranded siRNAs) respectively consisting of a component strand of one of the aforementioned double-stranded nucleic acids, preferably with the 3'-overhangs, but optionally without. The present disclosure also provides kits containing pairs of such single-stranded nucleic acids, which are capable of hybridizing with each other in vitro to form the aforementioned double-stranded siRNAs, which may then be introduced into cells.

The present disclosure also provides DNA that, when transcribed in a mammalian cell, yields an RNA (herein also referred to as an shRNA) having two complementary portions which are capable of self-hybridizing to produce a double-stranded motif or a sequence that differs from any one of the aforementioned sequences by a single base pair substitution.

The complementary portions will generally be joined by a spacer, which has suitable length and sequence to allow the two complementary portions to hybridize with each other. The two complementary (i.e. sense and antisense) portions may be joined 5'-3' in either order. The spacer will typically be a short sequence, of approximately 4-12 nucleotides, preferably 4-9 nucleotides, more preferably 6-9 nucleotides.

The 5' end of the spacer (immediately 3' of the upstream complementary portion) can consist of the nucleotides -UU- or -UG-, (though the use of these particular dinucleotides is not essential). A suitable spacer, recommended for use in the pSuper system of OligoEngine (Seattle, Wash., USA) is UUCAAGAGA. In this and other cases, the ends of the spacer may hybridize with each other.

Similarly, the transcribed RNA preferably includes a 3' overhang from the downstream complementary portion. Again, this can be —UU or -UG.

Such shRNA molecules may then be cleaved in the mammalian cell by the enzyme DICER to yield a double-stranded siRNA as described above, in which one or each strand of the hybridized dsRNA includes a 3' overhang.

Techniques for the synthesis of the nucleic acids of the invention are of course well known in the art.

The skilled person is well able to construct suitable transcription vectors for the DNA of the present disclosure using well-known techniques and commercially available materials. In particular, the DNA will be associated with control sequences, including a promoter and a transcription termination sequence.

Of particular suitability are the commercially available pSuper and pSuperior systems of OligoEngine (Seattle, Wash., USA). These use a polymerase-III promoter (H1) and a $T_5$ transcription terminator sequence that contributes two U residues at the 3' end of the transcript (which, after DICER processing, provide a 3' UU overhang of one strand of the siRNA).

The double-stranded siRNAs of the present disclosure may be introduced into mammalian cells in vitro or in vivo using known techniques, as described below, to suppress expression of the inflammasome.

Similarly, transcription vectors containing the DNAs of the present disclosure can be introduced into cells (e.g., bladder cells) in vitro or in vivo using known techniques, as described below, for transient or stable expression of RNA, again to suppress expression of the inflammasome.

Accordingly, the present disclosure also provides a method of suppressing inflammasome expression in a mammalian, e.g. human, cell, the method comprising administering to the cell a double-stranded siRNA of the present disclosure or a transcription vector of the present disclosure.

Similarly, the present disclosure further provides a method of treating a pathogenically-induced and/or chemically-induced bladder inflammation or neuroinflammation in a subject in the subject, the method comprising administering to a subject a double-stranded siRNA of the invention or a transcription vector of the present disclosure.

The present disclosure further provides the double-stranded siRNAs of the present disclosure and the transcription vectors of the present disclosure, for use in a method of treatment, preferably a method of treating a pathogen-induced and/or chemical-induced bladder inflammation or neuroinflammation in a subject.

The present disclosure further provides the use of the double-stranded siRNAs of the present disclosure and the transcription vectors of the present disclosure in the preparation of a medicament for the treatment of a pathogenically-induced and/or chemically-induced bladder inflammation or neuroinflammation in a subject in a subject.

The present disclosure further provides a composition comprising a double-stranded siRNA of the present disclosure or a transcription vector of the present disclosure in admixture with one or more pharmaceutically acceptable carriers. Suitable carriers include lipophilic carriers or vesicles, which may assist in penetration of the cell membrane.

Materials and methods suitable for the administration of siRNA duplexes and DNA vectors of the present disclosure are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE dextran and calcium phosphate precipitation. In vivo gene transfer techniques include transfection with viral (typically retroviral) vectors and viral coat protein-liposome mediated transfection.

In particular, suitable techniques for cellular administration of the nucleic acids of the present disclosure both in vitro and in vivo are known in the art, and include: RNA interference; Gene silencing in mammals by small interfering RNAs; Gene silencing mediated by small interfering RNAs in mammalian cells; RNAi: gene-silencing in therapeutic intervention; Systemic delivery using liposomes: Efficient delivery of siRNA for inhibition of gene expression in postnatal mice; Effective expression of small interfering RNA in human cells; Gene silencing by systemic delivery of synthetic siRNAs in adult mice; Virus mediated transfer; Lentiviral-mediated RNA interference; Retroviral delivery of small interfering RNA into primary cells; Retrovirus-delivered siRNA; Gene silencing by adenovirus-delivered siRNA; Peptide delivery. Other technologies that may be suitable for delivery of siRNA to the target cells are based on nanoparticles or nanocapsules.

Another aspect of the present disclosure is a composition comprising an inflammasome inhibitor and a pharmaceutically acceptable carrier or excipient.

In some embodiments, the inflammasome inhibitor is a NLRP3 inflammasome inhibitor. In some embodiments, the inflammasome inhibitor is glyburide, 2-mercaptoethane sulfonate sodium (Mesna), CY09, MCC950, 3,4-Methylene-dioxy-β-nitrostyrene (MNS), Tranilast (N-[3',4'-dimethoxy-cinnamoyl]-anthranilic acid, TR), OLT1177, Oridonin, 16673-34-0, JC124, FC11A-2, parthenolide, Z-VAD-FMK, Bay 11-7082, aloe vera, curcumin, artesunate, dapansutrile, glybenclamide, Epigallocatechin-3-gallate (EGCG), Genipin, red ginseng extract (RGE), isoliquiritigenin (TLG), NBC 6, NBC 19 INF 39, OXSI 2, (R)-Shikonin, INF 4E, CRID3 sodium salt, Mangiferin, propolis, quercetin, resveratrol, or Sulforaphane (SFN), or combinations thereof.

In some embodiments, the composition comprises an inflammasome inhibitor and an antidepressant agent. In some embodiments, the antidepressant agent is fluoxetine.
Administration of Inflammasome Inhibitors The inflammasome inhibitors may be administered to a subject, either alone or as a composition comprising the inflammasome inhibitor and a pharmaceutically acceptable carrier/excipient (i.e., a pharmaceutical composition), in an amount sufficient to induce an appropriate response in the subject.

The present disclosure further provides for the administration to a subject an effective amount of an inflammasome inhibitor for use with the methods disclosed herein. An "effective amount" as used herein means an amount which provides a therapeutic or prophylactic benefit. Effective amounts of the compositions/pharmaceutical compositions provided herein can be determined by a physician with consideration of individual differences in age, weight, tumor size, extent of infection or metastasis, and condition of the patient (subject). The optimal dosage and treatment regime for a particular patient can readily be determined by one skilled in the art of medicine by monitoring the patient for signs of disease and adjusting the treatment accordingly.

An effective amount of the composition(s) described herein can be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

A "pharmaceutically acceptable excipient and/or carrier" or "diagnostically acceptable excipient and/or carrier" includes but is not limited to, sterile distilled water, saline, phosphate buffered solutions, amino acid-based buffers, or bicarbonate buffered solutions. An excipient selected and the amount of excipient used will depend upon the mode of administration. Administration comprises an injection, infusion, or a combination thereof.

An effective amount for a particular subject/patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The composition(s) according to the present disclosure may also be administered with one or more additional therapeutic agents. Methods for co-administration with an additional therapeutic agent are well known in the art.

Co-administration can refer to administration at the same time in a subject, but can also include administrations that are spaced by hours or even days, weeks, or longer, as long as the administration of the one or more therapeutic agents is the result of a single treatment plan. The co-administration can comprise administering the composition(s) of the present disclosure before, after, or at the same time as the additional therapeutic agent. By way of example, the composition(s) of the present disclosure can be given as an initial dose in a multi-day protocol, with additional therapeutic agent(s) given on later administration days; or the additional therapeutic agent(s) given as an initial dose in a multi-day protocol, with the composition(s) of the present disclosure given on later administration days. On another hand, one or more additional therapeutic agent(s) and the composition(s) of the present disclosure can be administered on alternate days in a multi-day protocol. In still another example, a mixture of one or more additional therapeutic agent(s) and the compositions of the present disclosure can be administered concurrently. This is not meant to be a limiting list of possible administration protocols.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

Formulations of the one or more therapeutic agents can be prepared for storage by mixing with physiologically acceptable carriers, excipients, or stabilizers in the form of, e.g., lyophilized powders, slurries, aqueous solutions or suspensions.

The following Examples are provided by way of illustration and not by way of limitation.

EXAMPLES

Materials and Methods for Examples 1-7

Experimental Approach

The approach in this study is three-pronged: 1) in vitro analysis of the activation of the inflammasome in normal mouse urothelia by diabetic-associated DAMPS; 2) in vivo urinary function (cystometry) in diabetic mice with a genetic deletion of NLRP3 and 3) quantitation of nerve densities in the bladders of these mice to assess potential changes in specific nerves thought mediate specific DBD symptoms.

Animals

All protocols adhere to the NIH Guide for the Care and Use of Laboratory Animals and were approved by the Institutional Animal Care and Use Committee at Duke University Medical Center. Founder mice from The Jackson Laboratory (Bar Harbor, MA) consisted of Akita (C57BL/6J-Ins2Akita/J mice; stock number: 003548) (Wang et al. (1999) *The Journal of clinical investigation* 103:27-37) and NLRP3$^{-/-}$ (B6.129S6-Nlrp3$^{tm1Bhk}$/J (stock number: 021302) mice (Kovarova et al. (2012) *Journal of immunology* 189: 2006-2016). While the strain of origin for the NLRP3−/− mice (129S6/SvEvTac) is different from the Akita background (C57BL/6J) these mice have been backcrossed to C57BL/6J for >11 generations (www.jax.org). Mice were bred by the Breeding Core Facility at Duke University through an independently approved protocol and only female mice were used. All animals were genotyped by Transnetyx, Inc. (Cordova, TN) and provided to the laboratory around 4 weeks of age.

The results of genotyping were used to assign them to one of the 4 experimental groups. Nondiabetics are "nondiab" and diabetics are "diab". The groups are 1. NLRP3$^{+/+}$, nondiab, —homozygote wt NLRP3 genes, homozygote wt Ins2 genes—i.e. control mice
2. NLRP3$^{+/+}$, diab-homozygote wt NLRP3 genes; heterozygote for Akita mutation at the Ins2 gene—i.e. Akita diabetic control.
3. NLRP3$^{-/-}$, nondiab—both NLRP3 genes knocked out, homozygote wt Ins2 genes—i.e. NLRP3 knockout control.
4. NLRP3$^{-/-}$, diab, —both NLRP3 genes knocked out, heterozygote for Akita mutation at the Ins2 gene. This is the experimental mouse generated for this study.

Animals were received at 5 weeks of age. Blood glucose becomes high in Akita mice (200-300 mg/dL) around 4 weeks of age and remains high thereafter (Yoshioka et al. (1997) Diabetes 1997; 46:887-894; Dolber et al. (2013) *Neurourology and urodynamics* 34:72-8). Mice were grown to 15 weeks when DBD becomes apparent (Inouye et al. (2018) *Res Rep Urol* 10:219-225). No changes in urinary dysfunction were found at previous time points (Inouye et al. (2018) *Res Rep Urol* 10:219-225).

In Vitro Experiments

NLRP3$^{+/+}$, nondiab mice (i.e. control littermates) were used at 7-8 weeks of age. Urothelial cells were isolated (Kloskowski et al. (2014) *Hum Cell* 27:85-93) and plated (black-walled 96 well plates) at 50,000 cells/well in 90 μL complete media [F-12K media, 10% low-endotoxin dialyzed fetal bovine serum, 10 μM non-essential amino acids (all HyClone Laboratories, Logan, UT), 1.0 μg/mL hydrocortisone (Sigma-Aldrich, St. Louis, MO), 10 μg/mL insulin, 5 μg/mL transferrin and 6.7 ng/mL selenium (ITS, Gibco, Gaithersburg, Maryland). Following a 24 hr incubation (37° C., 95% air/5% $CO_2$), DAMPs (10 μL) were added and incubated as indicated. 1 h prior to harvest 1.25 mM ATP was added to untreated wells. In studies that examined ATP doses, cells were plated for 24 h, then treated with 1 μg/mL LPS (*E Coli* 055:B5; Sigma) in PBS or PBS alone for 24 h before treatment with the indicated doses of ATP for 1 h. Caspase-1 activity was then measured as previously described (Hughes et al. (2015) *Int Urol Nephrol* 47:1953-1964). Control florescence (0 mM DAMP) was subtracted from all wells and results normalized to the ATP response (except for the ATP dose response studies).

Histological Preparation

Bladders were formalin-fixed and paraffin-embedded in a transverse orientation. Sections (5 μm) from the lower third of the bladder were stained with anti-NLRP3 (1:100; cat #LS-C334192; Life Span BioSciences, Inc., Seattle, WA), anti-PGP9.5 (1:200; cat #381000; ThermoFisher, Waltham, MA), anti-Neurofilament 200 (NF-200; Aδ-fibers; 1:200, cat #N4142, Sigma-Aldrich, St. Louis, MO) or anti-Calcitonin Gene Related Peptide (CGRP; C-fibers; 1:80, cat #PC205L, Calbiochem, Burlington, MA) antibodies using standard methods and citrate antigen retrieval. Staining was visualized with secondary antibodies conjugated to either Alexa Fluor 488 (NLRP3, NF-200 and CGRP) or HRP (PGP9.5; developed with Vectastain ABC Staining Kit; Vector Laboratories, Burlingame, CA). All sections were imaged on a Zeiss Axio Imager 2 microscope (Zeiss, Oberkochen, Germany) running Zen software (Zeiss). Tiling micrographs encompassing the entire cross section were captured by the software and stitched into a continuous image. Calibration bars were inserted and images exported as TIFF files.

FAM-FLICA Caspase-1 Assay

Caspase-1 activity was assessed using the FAM-FLICA Caspase-1 Assay Kit (ImmunoChemistry Technologies, Bloomington, MN, USA) and the manufacturer's recommended protocol. Cells were analyzed on a FACSCalibur flow cytometer (BD-Bioscience; San Jose, CA) (excitation 488 nm, emission 533 nm) and dot plots of forward versus side scatter were used to gate on single cells. Histograms were created and gates were drawn to allow quantitation of the mean florescent intensity (MFI). The geometric mean of the MFI (the Geo Mean) of each sample was used for comparisons.

Blood Glucose

Blood from the submandibular vein was assessed with the AimStrip Plus blood glucose testing system (Germaine Laboratories, San Antonio, TX).

Evans Blue Dye Extravasation

Extravasation of Evans blue dye is a direct measurement of vascular permeability which is increased during inflammation. Thus, movement of this dye into a tissue is used as an indirect measurement in inflammation (Hughes et al. (2014) *American journal of physiology Renal physiology* 306:F299-308; Hughes et al. (2016) *The Journal of urology* 195:1598-1605; Hughes et al. (2016) *J Clin Cell Immunol* 7:396; Inouye et al. (2018) *Res Rep Urol* 10:219-225). In this study mice were injected (i.v.) with 10 mg/kg dye in saline and 1 h later sacrificed. Bladders were weighed and incubated overnight (56° C.) in 1 ml formamide and the absorbance (620 nM) of the formamide measured. Dye amounts were calculated from a standard curve and normalized to bladder weight.

Cystometry

Awake restrained cystometry was performed (Hughes et al. (2014) *American journal of physiology Renal physiology* 306:F299-308; Hughes et al. (2016) *The Journal of urology* 195:1598-1605; Hughes et al. (2016) *J Clin Cell Immunol* 7:396; Inouye et al. (2018) *Res Rep Urol* 10:219-225). One week prior, suprapubic tubes (PE-10 tubing with a flared end) were implanted in the bladder and secured with a purse string suture (6-0 silk). The tube was externalized at the back of the neck. One week later animals were placed in a Ballman-type restrainer (Natsume Seisakusho Co., Tokyo, Japan) inside of a Small Animal Cystometry Lab Station (Med Associates, St. Albans, VT) and positioned above an analytical balance to measure voided volume. The catheter was connected to a syringe pump via an in-line pressure transducer and sterile saline infused at 15 μL/min for 60-120 min. Scale and pressure readings were continuously recorded with Med-CMG software (Med Associates, St. Albans, VT). After voiding cycles stabilized (typically 3-4 cycles) an additional 3-8 cycles were recorded for quantitation. Immediately after the last void, infusion was stopped, the catheter attached to a 3 ml syringe and the plunger was withdrawn for 10-15 sec to recover any PVR. CMG Analysis software (version 1.06; Med Associates, St. Albans, VT) was used to analyze voiding cycles, defined as the time intravesicular pressure returned to baseline after a previous void until it returned to baseline following the next void. Voiding pressure is defined as the peak intravesical pressure, void volume as the amount of change on the scale and frequency as the number of voids per hour. Voiding efficiency was calculated as 100× the voiding volume divided by the bladder capacity (void volume+PVR).

Analysis of Nerve Densities

Quantitation of PGP9.5 and Aδ-nerve density in the bladder wall was carried out exactly as previously described (Lutolf et al. (2018) *Neurourology and urodynamics* 37:952-959) while quantitation of C-fibers in the urothelium required only minor modifications. Briefly, TIFF files were imported into NIS-Elements software (Nikon Co., Tokyo, Japan), calibrated and the bladder wall or urothelia layer demarcated (the ROI) and area calculated. PGP9.5$^+$ neurons were defined as black/brown spots >50 um$^2$. Aδ-fibers were defined as fluorescent areas >50 um$^2$ that stained positive with a nuclear co-stain (DAPI). C-fibers were defined as continuous fluorescent fibers >1 μm. Neuronal density in a given section was calculated by dividing the number of nerves by the μm$^2$ of the ROI.

Statistical Analysis

All parameters were assessed by either a two-tailed Students T-test or a one-way analysis of variance (ANOVA) followed by a Tukey's post-hoc analysis. Both analyses used GraphPad InStat software (La Jolla, CA) and statistical significance was defined as p<0.05.

Example 1: Diabetic DAMPS Activate the Inflammasome In Vitro

Figure 1A:
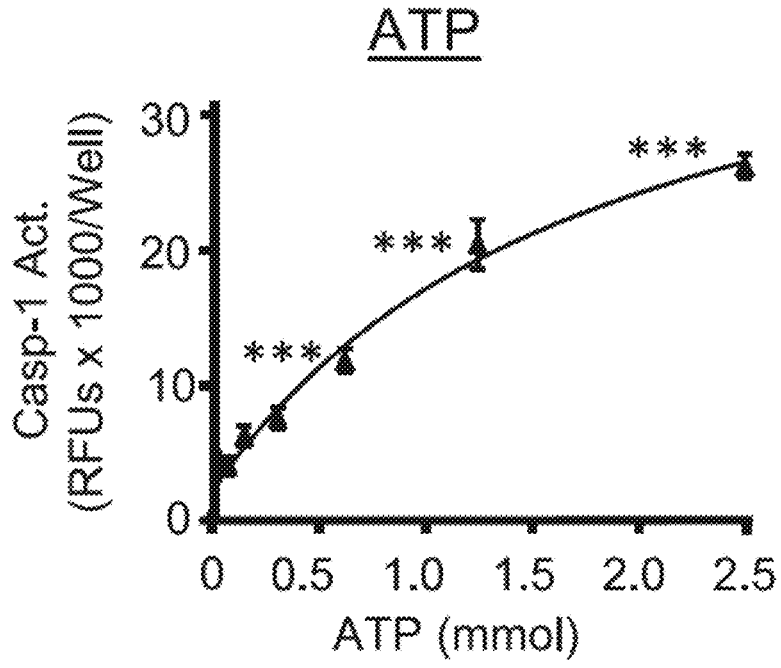
Figure 1B:
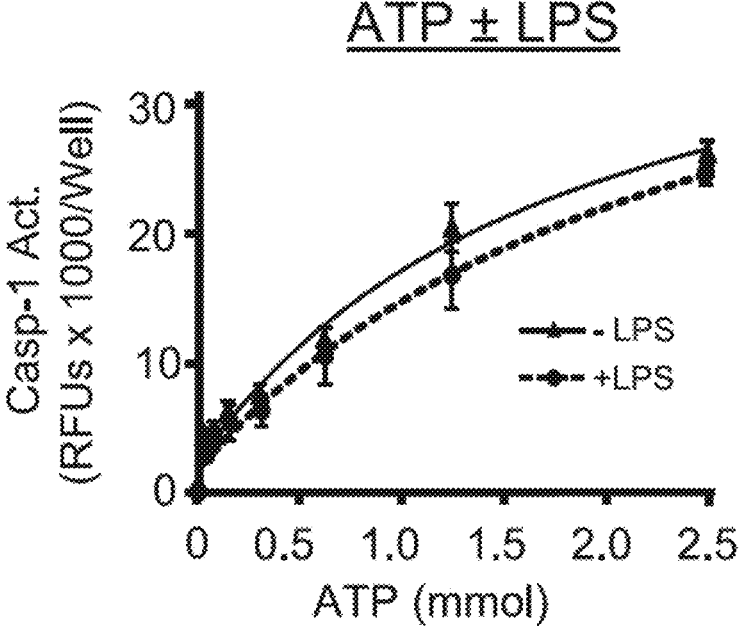
Figure 1E:
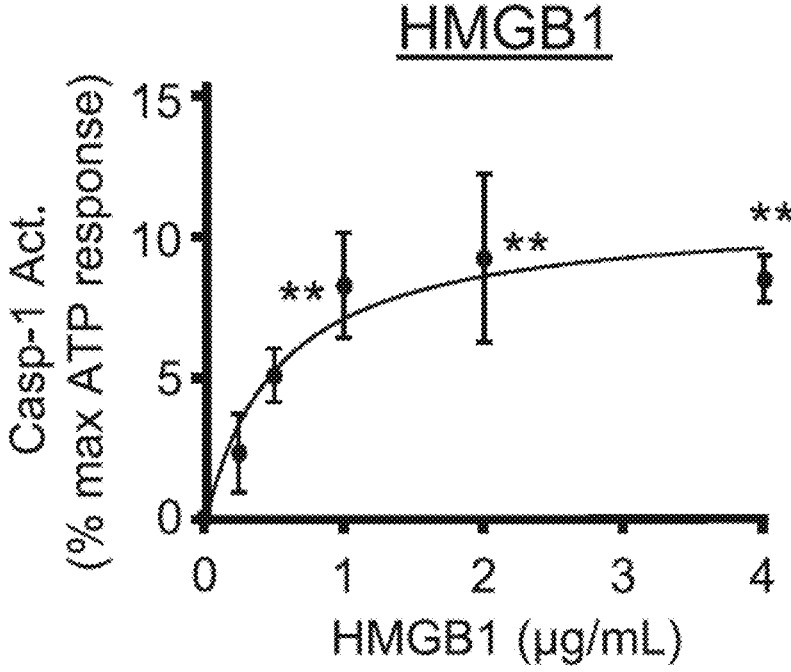
Figure 1F:
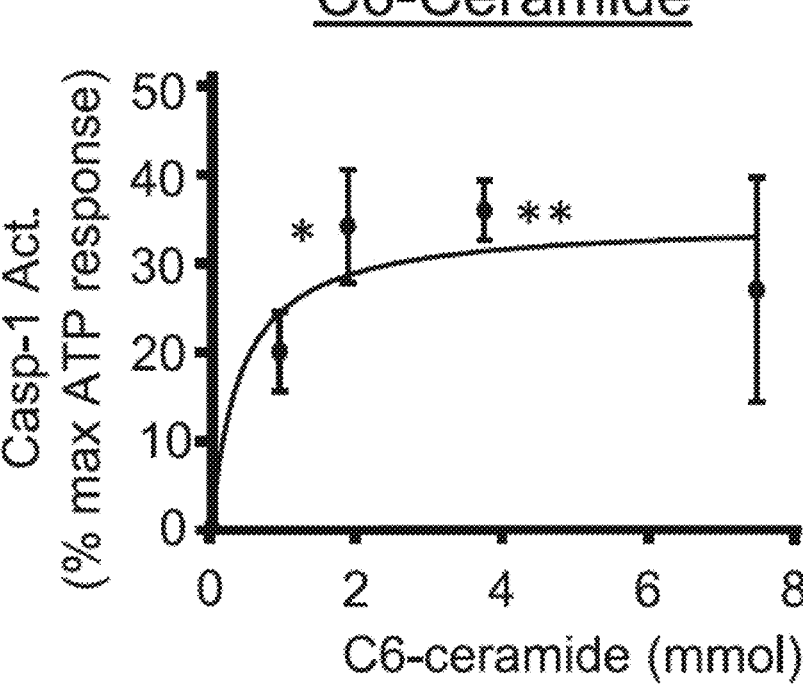
Figure 1G:
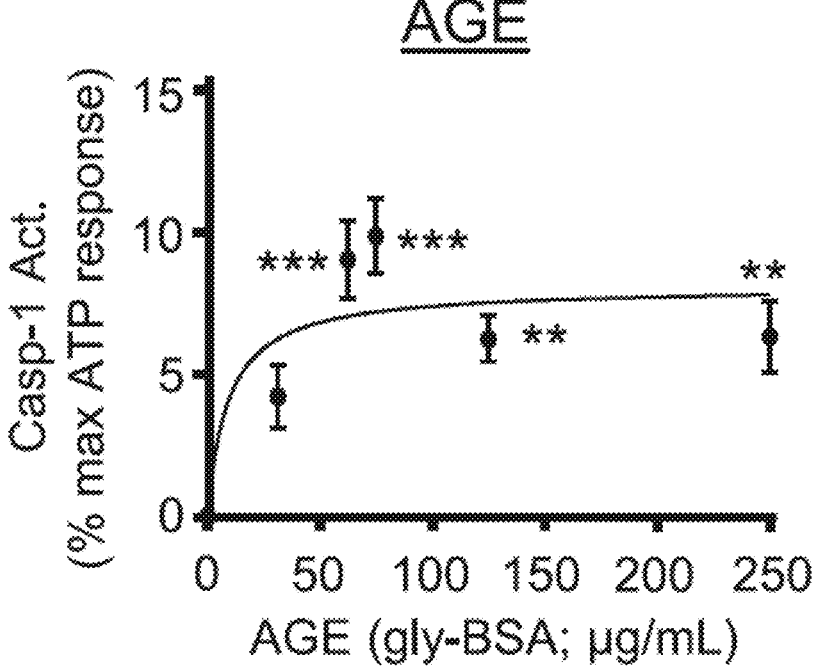

To assess the ability of diabetic DAMPS to trigger inflammasome activation, urothelial cells were treated in vitro and caspase-1 activity measured (Hughes et al. (2015) *Int Urol Nephrol* 47:1953-1964). ATP was prepared as a 25 mM stock in complete media (pH adjusted with 0.5 N NaOH) and dilutions made with complete media. The indicated final doses of ATP (in 10 μL) were then added to cells for 1 h prior to caspase-1 analysis. ATP, the quintessential NLRP3-activating DAMP, elicited a classic dose response (FIG. 1A) and is subsequently used to compare other DAMPs. In most cells, NLRP3 activation requires priming with an agent such as LPS (see, e.g., Bauernfeind et al. (2013) *EMBO molecular medicine* 5:814-826), However, LPS priming had no effect on these cells (FIG. 1B). Streptozotocin poisoning of beta cells is a widely used to create a type 1 model of diabetes. However, as shown in FIG. 1C, streptozotocin directly activates the inflammasome in urothelial cells, clearly contraindicating that model for these DBD studies. Finally, FIGS. 1D-1G demonstrates activation of caspase-1 by four separate diabetic DAMPS (Shin et al. (2015) *Ageing Res Rev* 24:66-76); monosodium urate (MSU), high mobility group box 1 protein (HMGB-1), C6-ceramide and advanced glycation end products (AGEs).

Discussion

The diabetic bladder is unique in that tissue damage can be caused by two independent mechanisms; 1) polyuria and 2) hyperglycemia. Here, the data demonstrate that it is the NLRP3 inflammasome, located within the urothelium, senses and responds to metabolic dysregulation by initiating an inflammatory response. Most importantly, diabetic mice lacking the NLRP3 gene do not develop diabetic bladder dysfunction.

Numerous diabetic DAMPS activated the NLRP3 inflammasome in vitro, demonstrating their pro-inflammatory potential. Interestingly, activation of NLRP3 did not require priming as in most cell types (Hughes et al. (2014) *American journal of physiology Renal physiology* 306:F299-308). While atypical, this has been reported and suggests urothelia either do not require priming or are already primed when isolated, possibly through exposure to the commensal microbiome (Patel et al. (2017) *Trends Mol Med* 23:165-180). As shown herein, streptozotocin is an activator of NLRP3. Streptozotocin is not a diabetic metabolite but rather a pancreatic toxin commonly used to induce diabetes in experimental models. These results discouraged the use of that model in DBD studies.

Example 2: NLRP3 is Activated During Diabetes

Figure 2:
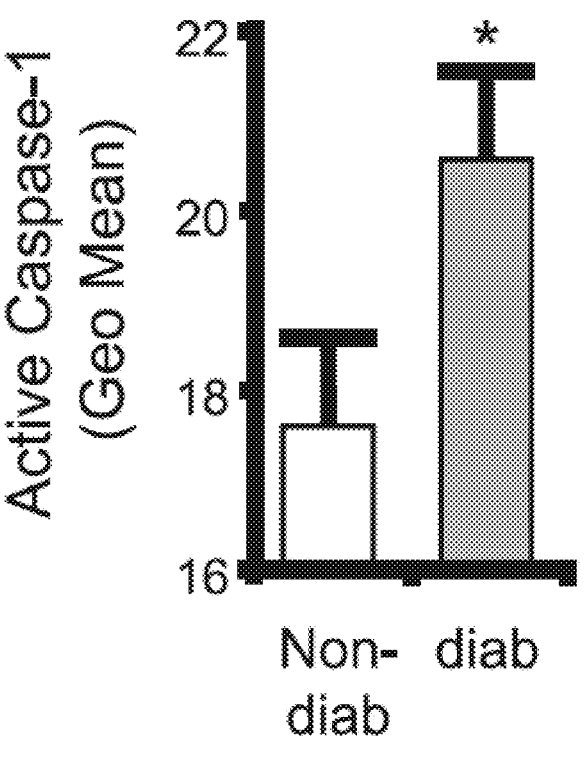
FIG. 2 is a graph showing NLRP3 is activated in the urothelium during diabetes. Inflammasome activity (caspase-1) is increased in urothelia from diabetic mice as compared to non-diabetic mice. Bars are mean±SEM. n=18 (nondiabetic), 17 (diabetic). *p<0.05 by Student's two tailed t-test.

To explore a role for the inflammasome in DBD it is essential to demonstrate that it is activated in the bladder by diabetes. Urothelia were isolated and stained with a FAM-FLICA Caspase-1 Assay Kit (Immunochemistry Tech., Bloomington, MN) as described. All mice were examined at 15 weeks of age. FIG. 2 demonstrates a significant increase in active caspase-1, the enzymatic readout for active inflammasomes, in urothelia from the 15 week diabetic animals compared to nondiabetic controls.

Figure 3:
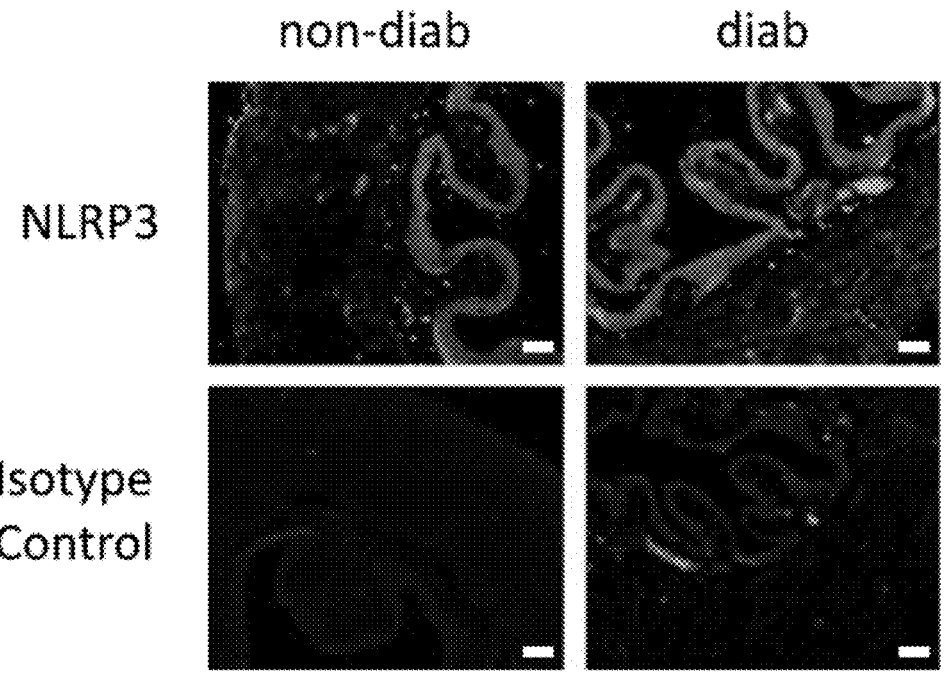
FIG. 3 are microscopy images showing that NLRP3 is present in mouse urothelia and its distribution is not effected by diabetes. All mice were examined at 15 weeks of age and all scale bars=50 μm.

Example 3: NLRP3 is Expressed in the Mouse Urothelia and its Distribution does not Change with Diabetes Although documented in rat (Hughes et al. (2015) *Int Urol Nephrol* 47:1953-1964; Hughes et al. (2014) *American journal of physiology Renal physiology* 306:F299-308), NLRP3 has never been examined in the mouse bladder. Sections of bladder (5 µm) from the indicated mice were stained for NLRP3 using standard immunocytochemistry and antigen retrieval protocols along with an Alexa Flour 488 conjugated secondary antibody. Isotype controls used normal rabbit serum instead of primary antibodies. n=3 (nondiabetic), 4 (diabetic). As shown in FIG. 3 (top left), expression of NLRP3 in the nondiabetic bladder was localized to the urothelial layer, identical to the rat. An indistinguishable distribution was noted in the diabetic strain (FIG. 3, top right). Isotype controls showed little background staining.

Example 4: The NLRP3−/− Genotype does not Affect Blood Glucose in the Diabetic To assess a role for NLRP3 in DBD numerous endpoints were explored both in nondiabetic and diabetic animals with intact NLRP3 (NLRP3$^{+/+}$) and nondiabetic and diabetic mice with NLRP3 genetically deleted (NLRP3$^{-/-}$). Blood glucose levels were assessed at week 15 using the AimStrip Plus blood glucose testing system. Blood glucose levels in these groups is shown in FIGS. 4A-4B. As expected, blood glucose levels were considerably greater in the diabetic compared to the nondiabetic mouse with NLRP3 present (NLRP3$^{+/+}$) (FIG. 4A). A similar increase with diabetes is seen with the NLRP3$^{-/-}$ strains (FIG. 4B). No significant differences were detected between the nondiabetic or diabetic based on NLRP3 expression (i.e., comparing the NLRP3$^{+/+}$, nondiabetic to the NLRP3$^{-/-}$, nondiabetic, and likewise with the diabetics). Thus, deletion of NLRP3 has no effect on blood glucose levels in either the nondiabetics or the diabetics.

Example 5: Inflammation is Present in the Diabetic Bladder and is Mediated Through NLRP3

Figures 5A, 5B:
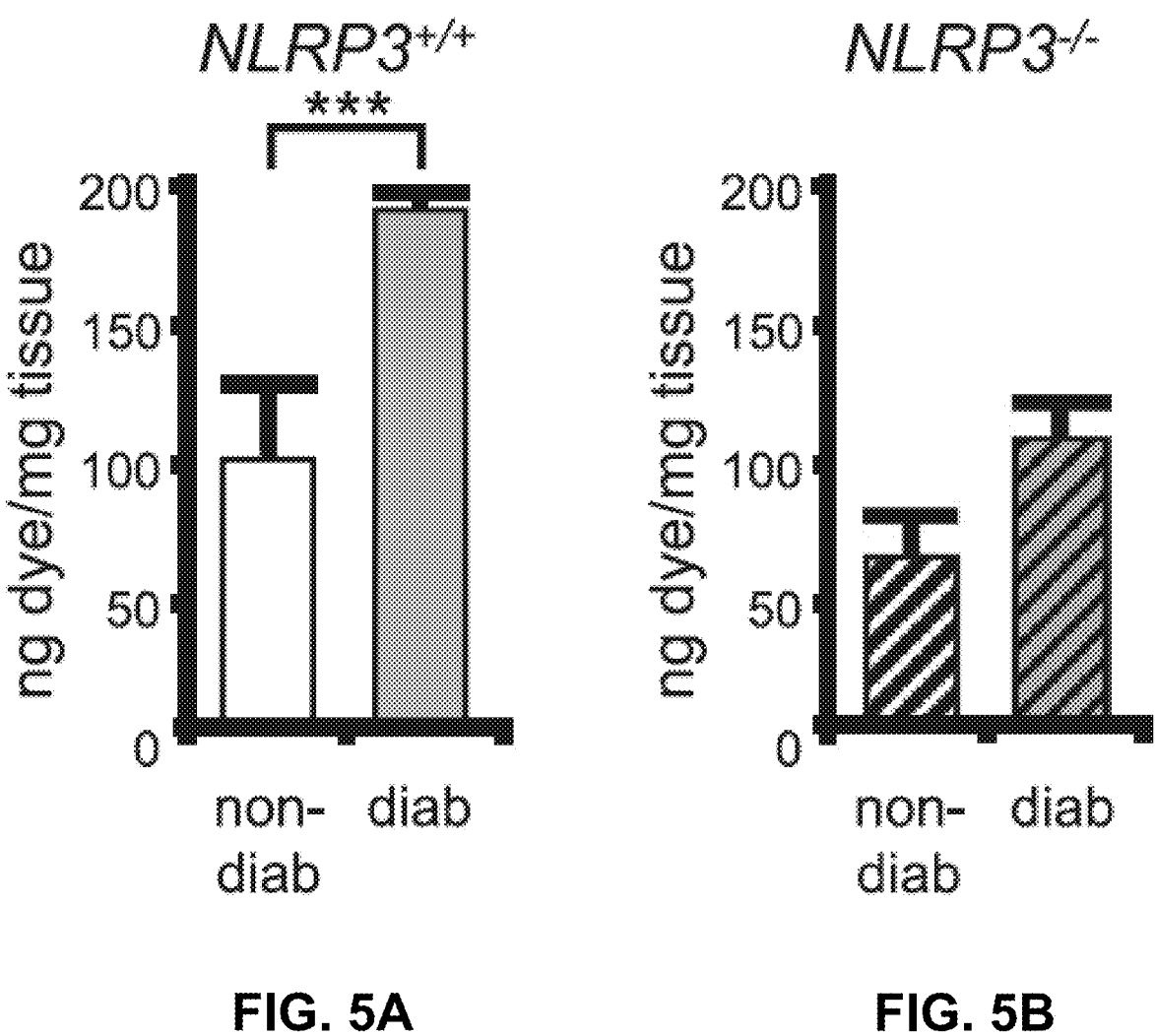
FIGS. 5A-5B shows inflammation is present in the diabetic bladder and is mediated through NLRP3.

While there is general evidence that inflammation is present in many tissues during diabetes, there is little or no evidence in the bladder. Therefore, the Evans blue dye extravasation assay, which is a direct measure of vascular permeability and an indirect measure of inflammation, was used to gain insight into inflammation in the diabetic bladder. The effect of diabetes on the induction of inflammation in the bladder was assessed in the presence and absence of NLRP3 using the Evans Blue dye extravasation assay described in the Methods section. As shown in FIG. 5A, there was a significant increase of dye extravasation in the 15-week diabetic mouse compared to the nondiabetic (both NLRP3$^{+/+}$), indicating substantial inflammation at this time point. This increase in extravasation associated with diabetes was completely blocked in the NLRP3$^{-/-}$ mouse (FIG. 5B).

Discussion

It has been shown that bladder inflammation and DBD develop in the Akita diabetic mouse by 15 weeks Inouye et al. (2018) *Res Rep Urol* 10:219-225). In that study (and this), extravasation of Evans blue was pronounced. This study also demonstrated a concurrently activation of the inflammasome. To investigate the role of NLRP3, the Akita mouse was crossed with an NLRP3$^{-/-}$ strain to create a unique substrain of diabetic mice lacking this inflammasome. Deletion of NLRP3 did not affect serum glucose levels but it did abolish the inflammatory response in the diabetic. Therefore, it appears urothelial NLRP3 is indeed capable of sensing the metabolic dysregulation of diabetes and promoting an inflammatory response.

Example 6: NLRP3 is Responsible for Bladder Dysfunction Associated with DBD

Figure 6A:
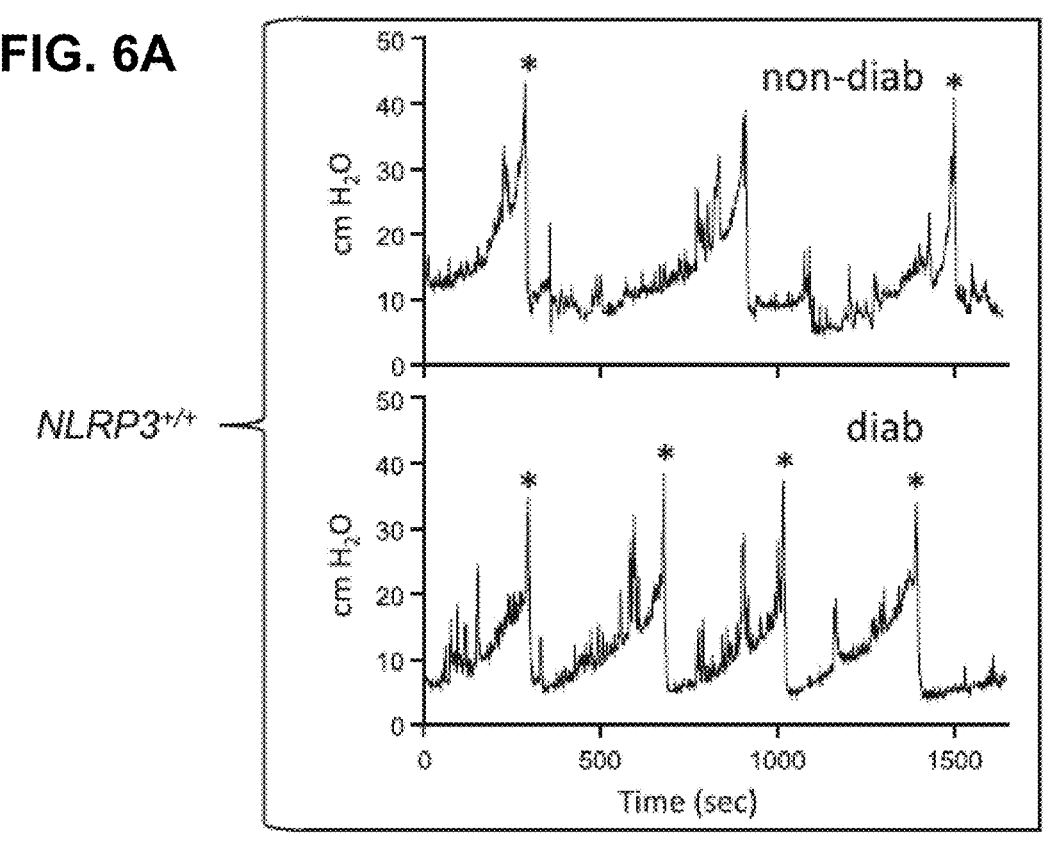
FIGS. 6A-6B show representative tracings of changes in intravesicpar pressures over time from the cystometry study used to demonstrate that NLRP3 is responsible for bladder dysfunction associated with DBD.
Figure 6B:
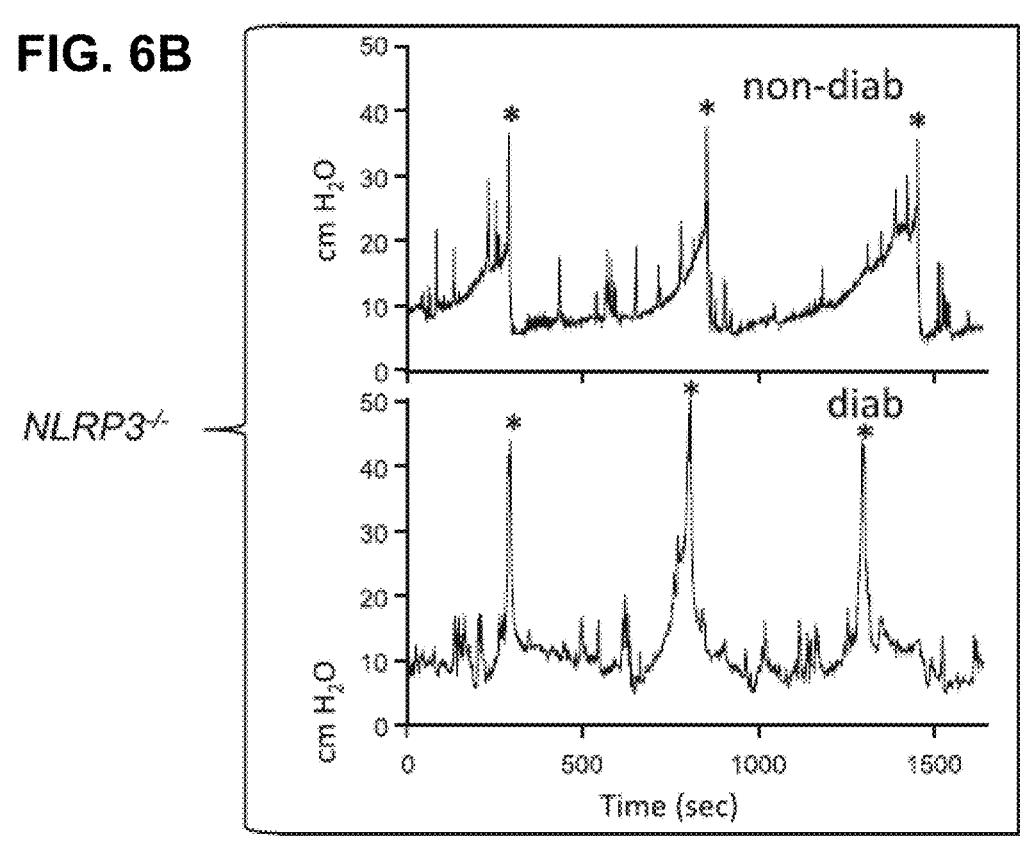

To investigate the effects of NLRP3 on bladder dysfunction, cystometry was performed at 15 weeks of age on the four experimental groups (Schneider et al. (2015) *BJU international* 115:8-15). FIGS. 6A-6B show representative tracings, for each of the four groups, of the changes in pressure (cm H$_2$O) in the bladder lumen during several micturition cycles, obtained during cystometry. These tracing were recorded using an in-line pressure transducer that made measurements every 0.25 s during the course of the experiment. The tracings were chosen to represent only several micturition cycles and do not display the entirety of the recording which was typically much longer. Voidings correspond with the large peaks in pressure and are indicated with asterisks (*). The tracings from the 4 groups were arranged vertically to align the first voiding volume of each while continuing the recording for the same length of time. This was to allow easy comparison and judgment of voiding frequency (number of voids, indicated by peaks in pressure, over time). Tracing align the first micturition to illustrate differences in the time between voids (the intercontraction interval) which is used to calculate voiding frequency. Typically 3-8 micturition cycles were quantitated per animal. Not shown are tracings of the scale aligned under the rat that measure voided volume.

Quantitative summaries are shown in FIGS. 7A-7H. The results of various parameters measured through cystometry are shown for nondiabetic and diabetic mice that either express NLRP3 (NLRP3+/+) or have that gene deleted (NLRP3−/−). All studies were performed at 15 weeks of age and animals were implanted with a suprapubic catheter one week prior to analysis. FIG. 7A demonstrates a decrease in void volume in the diabetic mice compared to the nondiabetic when NLRP3 is present (NLRP3$^{+/+}$). FIG. 7B shows an increase in voiding frequency in these same mice. In animal models, decreased void volume coupled with increased frequency can be considered synonymous with OAB (overactive bladder), which in humans requires subjective measures (such as urgency) that cannot be measured in animals. Importantly, neither of these diabetic changes were apparent in the absence of NLRP3 (NLRP3$^{−/−}$) (FIG. 7B and FIG. 7D).

The development of DBD, while complex, is thought to progress from an early, OAB phenotype to a later stage underactive bladder (UAB) characterized by increased post-void residual (PVR) volumes and decreased voiding efficiency (Gomez et al. (2011) *Current urology reports* 12:419-426). This UAB phenotype is indicative of a decompensated bladder. In the diabetic mouse at 15 weeks (FIG. 7E and FIG. 7G) a significant increase in PVR and decrease in voiding efficiency was detected, indicating the transition to UAB and decompensation had begun (FIG. 7E and FIG. 7G). However, these alterations are reduced in the NLRP3$^{−/−}$ animals (FIG. 7F and FIG. 7H).

Discussion

Cystometrically, the diabetic animal model demonstrate clear signs of early DBD at 15 weeks with decreased voiding volume, increased frequency and increased PVR. In the absence of NLRP3, diabetes did not change the frequency or void volume, unequivocally demonstrating that NLRP3 is responsible for the urinary changes of DBD. Interestingly, the diabetic bladder retained a significant PVR typically associated with later stage DBD and underactive bladder, thus suggesting that the transition towards a decompensated state has begun. Importantly, in the absence of NLRP3, the bladder maintained normal voiding volumes and efficient emptying, showing the importance of NLRP3 in the transition to decompensation where there is a much greater risk of complications such as infection and stone formation.

Example 7: NLRP3 Controls Changes in the Densities of Nerves Related to Specific DBD Symptoms DBD is associated with peripheral neuropathy and one gauge of neuropathy in a tissue is the alteration in nerve number and/or density which would be expected to decrease in diabetes and may be dependent on the NLRP3 inflammasome. To examine neuropathy in the bladder total nerves were quantitated using PGP9.5 as a pan neuronal marker in the bladder wall (Thompson et al. (1983) *Brain research* 278:224-228). Representative staining is shown in FIG. 8A. Arrows indicate positive staining while the block arrow indicates nonspecific, or at least non-neuronal staining of the urothelia. While the significance of the urothelial staining is unknown, it has been previously reported (Lutolf et al. (2018) *Neurourology and urodynamics* 2018; 37:952-959; Guan et al. (2015) *British journal of pharmacology* 172: 4024-4037). Quantitatively, the total number of nerves in the bladder wall was decreased in the diabetic mouse (FIG. 8B) in the presence of NLRP3, but this effect was not significant in the NLRP3$^{−/−}$ strain (FIG. 8C). There was no change of bladder wall size in any group (FIG. 8D and FIG. 8E) so changes in nerve density (FIG. 8F and FIG. 8G) directly reflect the changes in nerve number.

Next, the specific nerve types thought to underlie individual bladder symptoms in diabetics were assessed. First, bladder fullness is relayed to the CNS via Aδ-fibers and patients often report a reduced sensation of bladder fullness. Thus, there may be a decrease in the number and/or density of these fibers in the diabetic mice which may be driven by the NLRP3 inflammasome. Because Aδ-fibers are predominantly in the bladder wall, they were quantitated in this compartment. Representative staining is shown in FIG. 8H. As shown in FIG. 8I, there was a significant decrease in the number of Aδ-fibers (NF-200$^+$ cells) in the bladder wall of the diabetic mouse when NLRP3 was present. This decrease was not detected in the NLRP3$^{−/−}$ diabetics (FIG. 8J). Bladder wall size (FIG. 8K and FIG. 8L) remained constant, so changes in Aδ-fiber densities (FIG. 8M and FIG. 8N) reflect changes in fiber number.

C-fibers are associated with an OAB phenotype (38) which is common in early stage diabetic patients and also apparent in our mice at 15 weeks of age (FIG. 7). Thus, there may be an increase in the number and/or density of these fibers with diabetes and this change may be driven by NLRP3. C-fibers are predominately in the urothelia and lamina propria. Representative staining is shown in FIG. 8O. As shown in FIG. 8P, the number of C-fibers (CGRP$^+$) in the urothelium was significantly increased in the diabetic bladders when NLRP3 was intact. This increase did not occur in the diabetic NLRP3$^{−/−}$ mice (FIG. 8Q). Urothelium did not change size (FIG. 8R and FIG. 8S) so density results (FIG. 8T and FIG. 8U) again reflected changes in cell numbers.

Discussion

While traditional concepts of DBD postulated that the sole pathological cause was autonomic neuropathy (Kaplan et al. (1988) *J Diabet Complications* 2:133-139), more conventional views recognize multifactorial disturbances (Liu et al. (2014) Chinese medical journal 127:1357-1364). Considering the known association between peripheral neuropathy and the development of DBD (Tanik et al. (2016) *Int Neurourol J* 2016; 20:232-23), various DBD-related symptoms could result from deleterious effects on the nerves within the bladder and decreased nerve density in the bladder wall in the diabetic mice was observed. Furthermore, the effects on different types of nerves vary. The Aδ-fibers, which sense fullness in the bladder, were decreased in the bladder wall and this may explain why a diminished sense of fullness is often reported with diabetic patients. On the other hand, the C-fiber population in the urothelium increased in the diabetic bladders. C-fibers normally sense pain but they are also associated with the emergence of an overactive bladder phenotype (Fowler (2002) *Urology* 59:37-42) which is common in early stage diabetic patients. Thus, the differential effects of inflammation on these two types of nerves provide a possible explanation for the specific symptoms associated with DBD.

The current study provides a convincing mechanism whereby a plethora of diabetic insults converge on NLRP3 in the urothelia and translate into inflammation and damage to the bladder. These insults include ATP and numerous metabolites but also likely include additional insults such as reactive oxygen species, created from excessive oxidative phosphorylation, and ischemia which is a well-known activator of NLRP3 that recent studies suggest play a role in DBD (Gotoh et al. (2018) *Neurourology and urodynamics* 37:666-672). The signal emanating from the urothelia to trigger effects in the other bladder tissues has unidentified but likely attributable to the major products of the inflammasome, IL-1β and IL-18, acting in a paracrine fashion. Indeed it has been shown that IL-1β is responsible for the decrease in PGP9.5+ nerves in the bladder wall in a rat model of bladder outlet obstruction (Lutolf et al. (2018) *Neurourology and urodynamics* 37:952-959) and that IL-1β is implicated it in bladder smooth muscle hypertrophy (Haldar et al. (2015) *The Journal of biological chemistry* 290:6574-6583).

The central role of NLRP3 in development of DBD suggests a strategy for the prevention and management of this diabetic complication. According to the DCCT trial, only 58% of patients are able to maintain the strict glycemic control favored by the American Diabetic Association (Selvin et al. (2014) Ann Intern Med 160:517-525). While strict regulation does prevent retinopathy, nephropathy and other diabetic complications, bladder dysfunction still remains a problem for these patients (Genuth et al. (2006) Endocr Pract 12 Suppl 1:34-41; Sarma et al. (2009) Urology 73:1203-1209). The present study demonstrates that NLRP3 inhibitors can prevent or treat DBD and possibly other diabetic complications where this pathway plays a central role.

The results clearly show that activation of the NLRP3 inflammasome, possibly by diabetic metabolites, underlies bladder dysfunction and denervation during DBD in mice and therefore may serve as a critical pharmacological target for combating this complication in humans.

Materials and Methods for Examples 8-10

Animals

All protocols adhere to the NIH Guide for the Care and Use of Laboratory Animals and were approved by the Institutional Animal Care and Use committee at Duke University Medical Center. Female Sprague Dawley rats (≈200 grams, 40-50 days of age, Envigo, Indianapolis, IN) were used in all studies.

Cell Isolation

The cell isolation protocol was modified from a previously published method (Hughes et al. (2018) Diabetes 68:430-440; Kloskowski et al. (2014) *Hum Cell.* 27(2):85-93). Briefly, rats were sacrificed and the bladders removed and placed in sterile PBS. Bladders were then inverted over an 18-gauge blunt tip needle, inflated with PBS, and a purse string suture was used to tie off the bladder. The inflated bladder was then submerged in Collagenase P (1 mg/mL in complete media) and shaken for 1 hour at 37° C. Cells were then passed through a 40 μm nylon mesh to remove debris, pelleted and resuspended in complete media [F-12K media (HyClone Laboratories, Logan, UT) supplemented with 10% low-endotoxin dialyzed fetal bovine serum (HyClone Laboratories, Logan, UT), 10 μM non-essential amino acids (HyClone Laboratories, Logan, UT), 1.0 μg/mL hydrocortisone (Sigma-Aldrich, St. Louis, MO), 10 μg/mL insulin (Gibco Laboratories, Gaithersburg, MD), 5 μg/mL transferrin (Gibco Laboratories, Gaithersburg, MD), 6.7 ng/mL selenium (Gibco Laboratories, Gaithersburg, MD), 100 U/mL penicillin (Gibco Laboratories, Gaithersburg, MD), and 100 μg/mL streptomycin (Gibco Laboratories, Gaithersburg, MD)]. Cells were counted and plated at 50,000 cells/well in 90 μL complete media in black-walled 96-well plates. Cells were then incubated in a water-saturated environment for 24 hours at 37° C., 95% air, and 5% $CO_2$. Media was removed and replaced with fresh media (90 μL for agonist studies, 80 μL for inhibitor studies) just prior to the start of experimental treatments.

Experimental Treatments

In vitro experiments were performed essentially as previously described in the Materials and Methods for Examples 1-7. For agonist response studies, CPPD and MSU (InvivoGen, San Diego, CA) were prepared to the stock concentrations of 1.25 mg/mL and 12.5 μg/mL, respectively. Using PBS (for CPPD) or complete media (for MSU), 1:2 serial dilutions were prepared. Wells were then treated with 10 μL of the appropriate dilution of stone DAMP for a final volume of 100 μL. After treatment, cells were incubated for another 24 hours at 37° C.

For inhibition response studies, the general ROS scavenger N-acetylcysteine was prepared to the stock concentration of 5 mM for MSU treatment and to 50 mM for CPPD treatment. Prior to treatment, the stock concentration of NAC was buffered to pH 7.2. Verapamil was prepared to a stock concentration of 1.5 mM for serial dilution and cell treatment. Using complete media for NAC and PBS for Verapamil, 1:2 serial dilutions were prepared. Cells were treated with 10 μL of NAC or Verapamil and incubated at 37° C. for 1 or 4 hours, respectively. After pre-treatment, cells were then treated with 10 μL of CPPD (62.5 μM final) or MSU (1.25 μM final) to a final volume of 100 μL. Plates were then incubated for an additional 24 hours at 37° C. One hour prior to the end of the incubation, untreated control wells were administered 1.25 mM ATP to serve as a standard for maximal caspase response.

Caspase-1 Assay

The caspase-1 assay was performed as reported (Hughes et al. (2015) *Int Urol Nephrol.* 47(12):1953-1964). Briefly, media was removed and cells lysed in 50 μL lysis buffer (10 mM $MgCl_2$ and 0.25% Igepal CA-630) for 5 minutes. An additional 50 μL of storage buffer (40 mM HEPES (pH 7.4), 20 mM NaCl, 2 mM EDTA and 20% glycerol) was added, and the plates frozen at −80° C. until use (>30 minutes). Plates were then thawed and 50 μL of 50 mM Hepes with 10% Sucrose and 0.1% CHAPS, 10 μL dithiothreitol (final concentration of 5.5 mM), and 20 μL Z-YVAD-AFC substrate (final concentration of 110 μM) were added to each well. Plates were then incubated in the dark for 1 hour at 37° C. with mild shaking. Florescence was then measured (excitation 400 nm, emission 505 nm). Florescence in untreated wells (0 mM stone DAMP) was subtracted from all wells and results normalized to the ATP response. Results were reported as a percentage of ATP response.

Statistical Analysis

Statistical analysis was performed by a one-way analysis of variance followed by a Dunnett's post-hoc analysis using GraphPad InStat software (La Jolla, CA).

Example 8: CPPD, MSU, and Calcium Oxalate Produce a Dose-Dependent Increase in Caspase-1 Activation To determine if stone DAMPs activate caspase-1, urothelial cells were incubated overnight prior to treatment with calcium pyrophosphate (CPPD), monosodium urate (MSU), or calcium oxalate for 24 hours. Additional wells were treated with 1.25 mM ATP for 1 hour to indicate maximal caspase-1 activation and DAMP-treated wells were normalized to these ATP-treated wells. CPPD triggers a robust and dose-dependent activation of caspase-1 in isolated urothelium in vitro, with a maximal response of approximately 50% of the ATP response and an $EC_{50}$ of 62.5 µg/mL (FIG. 9A). MSU was less efficacious yet more potent than CPPD, with a maximal response of 25% of the ATP response but an $EC_{50}$ of 0.156 µg/mL (FIG. 9B). The dose response curve for CaOx is shown in FIG. 9C.

Example 9: N-Acetylcysteine Inhibits Caspase-1 Activation in Cells Treated with Stone DAMPs To determine if CPPD and MSU signal for inflammasome activation in the urothelia through ROS, the general ROS scavenger N-acetylcysteine (NAC) was utilized. Urothelial cells were incubated overnight and then treated with decreasing concentrations of NAC for 1 hour before treatment with 62.5 µg/mL CPPD or 1.25 µg/mL MSU for 24 hours. The caspase-1 assay was then performed as described in the Materials and Methods section. CPPD-treated cells had a higher $IC_{50}$ (625 µM) versus MSU-treated cells ($IC_{50}$=31.25 µM). As shown in FIG. 10A, a NAC concentration of 5 mM was sufficient to completely suppress caspase-1 activation in cells treated with CPPD ($IC_{50}$=625 µM). However, as shown in FIG. 10B, a NAC concentration of just 500 µM was sufficient to completely suppress caspase-1 activation in MSU-treated cells ($IC_{50}$=31.25 µM).

Discussion

This study provides the first exploration into the urinary DAMP-ROS-NLRP3 inflammasome pathway within the urothelium. It was found that NLRP3 is activated in vitro in urothelial cells by two common stone-forming components. Importantly, it was also found that NLRP3 is mediated through an upregulation in intracellular ROS and release of TXNIP from thioredoxin. Specifically, the general ROS scavenger NAC was able to prevent inflammasome activation in both CPPD and MSU-treated urothelial cells. Further, directed targeting of a ROS-responsive protein (TXNIP) that forms a structural component of the NLRP3 inflammasome was also able to prevent inflammasome activity. These findings demonstrate a ROS-driven pathway in stone-induced urothelial inflammation that relies on the TXNIP protein for functionality.

Example 10: Verapamil Inhibits Caspase-1 Activation

Verapamil (Ver) is a calcium channel blocker that has been shown to downregulate the expression of the NLRP3 binding protein TXNIP (Melone et al. (2018) *Pharm Res.* 35(2):44; Xu et al. (2012) *Diabetes* 61(4):848-856), and thus has been used in several studies to assess a role for this critical structural component of the NLRP3 inflammasome in DAMP pathways mediated by ROS (Abais et al. (2014) *J Biological Chem* 289(39):27159-27168; Xu et al. (2019) *Oxid Med Cell Longev* 1896041). Urothelial cells were incubated overnight and then treated with decreasing concentrations of Verapamil for 4 hours before treatment with 62.5 µg/mL CPPD or 1.25 µg/mL MSU for 24 hours. The caspase-1 assay was then performed as described in the Materials and Methods section. Both CPPD and MSU-treated cells had the same $IC_{50}$ (100 µM). As shown in FIG. 11A, a dose of 150 µM of Verapamil was sufficient to completely inhibit CPPD-mediated caspase-1 activation ($IC_{50}$=100 µM). In a similar fashion, shown in FIG. 11B, MSU-induced caspase-1 activation was also completely suppressed in cells by 150 µM Verapamil ($IC_{50}$=100 µM).

Discussion

Interestingly, while NAC and Verapamil both were able to abolish inflammasome activation by CPPD and MSU, there were exciting differences in their respective abilities to do so. First, NAC doses required to completely inhibit inflammasome activation were higher in cells treated with CPPD (5 mM) compared to MSU (500 µM). This differential response is possibly the result of differences in intracellular ROS production by the various stone DAMPs. Second, there were no differences in treatment dose of Verapamil required to completely inhibit inflammasome activation in either CPPD or MSU-treated cells. Maximal inhibition of caspase-1 activity was seen at a Verapamil dose of 150 µM after treatment with either stone DAMP. Therefore, it appears that functional TXNIP is required for the activation of NLRP3 regardless of the magnitude of ROS production. Based on these findings, targeted therapies aimed at impeding different steps within this pathway may be useful to inhibit stone-mediated inflammasome activity.

NAC is an FDA-approved medication that functions as a general ROS scavenger and acts as a precursor molecule for the regeneration of intracellular glutathione, another scavenger of ROS (Mokhtari et al. (2017) *Cell J.* 19(1):11-17). Clinically, NAC is very effective in a number of patient populations, such as acetaminophen overdose, polycystic ovarian syndrome, and chronic bronchitis. While the usefulness of NAC in these patient populations is well-established, its potential in treating urinary DAMP-mediated bladder inflammation has never before been explored. Our findings suggest that this drug may be a useful tool in turning off bladder inflammation caused by urinary DAMPs, thereby allowing for reduction in inflammatory complications.

Verapamil is a non-dihydropyridine calcium channel blocker used in a number of medical conditions, such as hypertension, angina, and cluster headaches. An early study suggested that its calcium channel blocking ability might reduce the level of stone forming components in the urine, but a subsequent study did not corroborate this finding (Iguchi et al. (1993) *Hinyokika Kiyo.* 39(5):425-431; Sarica et al. (2007) *Urological research* 35(1):23-27). However, in this study, verapamil's ability to downregulate expression of TXNIP (Chen et al. (2009) *American J. of physiology Endocrinology and metabolism.* 296(5):E1133-1139; Al-Gayyar et al. (2011) *British J. of pharmacology* 164(1):170-180) proved a useful tool to block stone-DAMP activation of NLRP3. Therefore, while it may not affect the concentration of stone forming moieties, it may actually protect the urinary tract from these pro-inflammatory urinary components.

This study demonstrates that urinary stone-forming DAMPS activate NLRP3 in urothelial cells via ROS production and require the presence of TXNIP. This pathway is effectively blocked by the administration of the anti-oxidant, NAC, or by down-regulating TXNIP expression with verapamil. These agents can be useful in preventing lower urinary tract inflammation, pain, and risk of fibrosis and scarring in stone forming patients. More broadly, and the subject of future studies, many other urinary DAMPs could also activate the NLRP3 inflammasome and provoke an urothelial inflammatory response via the same pathway demonstrated in this investigation. It is well-known that consumption of certain foods, such as chocolate, alcohol, acidic juices, can exacerbate lower urinary tract symptoms in sensitive patients. Abstinence from these dietary factors is very effective, but that requires the identification of the specific item which can be challenging. If the pathway elucidated here is common to many other urinary DAMPs, then targeting ROS production, TXNIP expression and/or NLRP3 activation could be implemented as a treatment strategy even if the inciting factor is unknown. Additionally, it has been shown in Example 1 that diabetic metabolites are capable of activating NLRP3 in urothelium and this contributes to the development of diabetic bladder dysfunction (DBD). If future studies demonstrate that these metabolites have the same mechanism of action as the stone DAMPs (uric acid being an example of both) then targeting ROS production or TXNIP expression may be useful in preventing DBD.

Conclusion

Urinary stones are comprised of components that induce a state of inflammation, which can affect patients in a number of clinically meaningful ways. The present study suggests that this inflammation is due, in part, to the activation of the NLRP3 inflammasome by increased intracellular concentrations of ROS that impinge upon TXNIP. Importantly, this study illuminates steps in the pathway that can be pharmacologically targeted to potentially reduce complications of inflammation in stone patients.

Materials and Methods for Examples 11-15

Animals

All protocols adhere to the NIH Guide for the Care and Use of Laboratory animals and were approved by the Institutional Animal Care and Use Committee at Duke University Medical Center. Female Sprague Dawley Rats (~200 g) were randomly divided into groups to receive the various treatments shown in Table 1.

TABLE 1

| Groups and Treatments | | | | | |
| --- | --- | --- | --- | --- | --- |
| Group | Vehicle | Gly | CP | Mesna | Fluoxetine |
| Control | 10% EtOH | | | | |
| Glyburide | | 2.5 mg/kg | | | |
| CP | | | 150 mg/kg | | |
| CP + Gly | | 2.5 mg/kg | 150 mg/kg | | |
| CP + Mesna | | | 150 mg/kg | 40 mg/kg | |
| CP fluoxetine | | | | | 5 mg/kg |

Not all treatments groups were used for all end points. The rats were then subjected to the dosing regimen shown in FIG. 12. Basically, animals were injected i.p. with a single dose of CP (150 mg/kg) or PBS as a control and 24 hr later end point analysis began. However, depending on the experiment, rats were also pretreated/treated with various inhibitors to assess the role of various pathways. To assess a role for NLRP3, rats were given the NLRP3 inhibitor glyburide (Lamkanfi et al. (2009) *The Journal of cell biology* 187: 61-70) (GLY; 2.5 mg/kg in 10% ethanol in PBS, ≈800 μL/rat, p.o., (Hughes et al. (2014) *American journal of physiology Renal physiology* 306: F299-308) or vehicle as the control. GLY was given in the evening prior to CP administration (5 PM) and again 16 h later (9 AM). Four h later (1 PM), CP or PBS alone was injected (i.p). Additional doses of GLY were given 4 h (5 PM) and 20 h (9 AM) after CP injection. 24 h after CP injection animals were sacrificed or entered into the Evans blue protocol or behavior assays. To assess a role for acrolein-induced cystitis, Mesna (40 mg/kg, (Ali et al. (2014) *Indian J Pharmacol* 46: 105-108) was administered to a group of animals 4 h before CP, immediately before CP, 4 h and 16 h after CP. For behavior assays, an additional group of rats was administered the antidepressant fluoxetine (FLU) as a control. FLU was given 48 h, 24 h and 4 h prior to CP administration (and 20 h after). This proved to minimum time necessary to see effects of fluoxetine, which are most noted chronically but acute effects have been reported (Silva et al. (1999) *Braz J Med Biol Res* 32: 333-339).

Bladder Weight

Bladder weights were recorded at the time of euthanasia.

Evans Blue Assay and Gross Analysis

Inflammation in the bladder and inflammation/blood brain barrier permeability in the brain was measured using Evans blue dye (Belayev et al. (1996) *Brain research* 739: 88-96; Michels et al. (2015) *Brain Behav Immun* 43: 54-59). Rats were injected i.v. in the tail vein (2%, 3 ml/kg). One hour after injection, rats were euthanized and transcardially perfused through a ventricular catheter to remove intravascular dye. For gross analysis brains were isolated and sectioned coronally using a scalpel and photographed. For other analyses bladders were removed, weighed and placed into 1 ml formamide. The hippocampus and pons were dissected out, weighed and placed into 250 μL formamide. Samples were then incubated at 56° C. overnight with shaking. Absorbance was measured (620 nm) and the results calculated as pg Evans blue/μg tissue using a standard curve of Evans blue absorbance.

Caspase-1 Activity

Caspase-1 activity was measured using a fluorometric assay as previously described (28). Briefly, samples were homogenized in 200 μl of Lysis Buffer (10 mM MgCl$_2$, 0.25% Igepal CA-630), centrifuged (10,000×g, 10 min) and the supernatant mixed with equal parts Storage Buffer [40 mM Hepes (pH 7.4), 20 mM NaCl, 2 mM EDTA, 20% glycerol. Extract (75 μl) was combined with 25 μl of a 1:1 combination of Lysis and Storage buffer, 50 μl assay buffer [25 mm HEPES (pH 7.5), 5% sucrose, 0.05% CHAPS], 10 μl 100 mM DTT and 20 μl 1 mM N-acetyl-Tyr-Val-Ala-Asp-7-Amino-4-trifluoromethylcoumarin (Ac-YVAD-AFC) in blacked-walled 96-well plates. Plates were incubated at 37° C. for 1 hour in the dark with mild shaking. Fluorescence (excitation: 400 nm, emission: 505 nm) was measured and compared with a standard curve of fluorescence versus free AFC to determine the rate of product production. Protein concentrations of sample aliquots were assessed by Bradford assay (Bradford (2004) *Anal Biochem* 72: 248-254) and rates were normalized to protein to calculate the specific activity of caspase-1.

Quantitative PCR (qPCR)

qPCR was performed by Gene Master LLC (Cary, NC) using their standard techniques. RNA was extracted using Trizol (Thermo Fisher, Waltham, MA) according to manufacturer's protocol and samples stored at −20° C. until transferred to Gene Master (<2 weeks). cDNA was then generated (Invitrogen Superscript III kit) and qPCR run in triplicate with validated primers (pro-IL-1β: forward primer: caccttctttccttcatctttg (SEQ ID NO:01), reverse primer: tcgttgcttgtctctccttg (SEQ ID NO:02); pro-IL-18: forward primer: aggctcttgtgtcaacttcaaa (SEQ ID NO:03), reverse primer: agtctggtctgggattcgtt (SEQ ID NO:04); NLRP3: forward primer: gaagattaccccacccgagaaa (SEQ ID NO:05), reverse primer: ccagcaaacctatccactcc (SEQ ID NO:06); ASC: forward primer: atctggaggggtatggcttg (SEQ ID NO:07), reverse primer: cttgttttggttgggggtct (SEQ ID NO:08)) using β-actin (forward primer: cccattgaacacggcatt (SEQ ID NO:09), reverse primer: accagaggcatacagggaca (SEQ ID NO:10)) as an internal control. Gene expression levels of vehicle-treated rats were averaged and normalized to a value of one. Results are presented as relative expression (fold increase) of the studied genes in treated rats compared to vehicle.

Histological Analysis

Whole brains were immersed in 10% neutral buffered formalin (RT, 48 h), sliced coronally and embedded in paraffin blocks with the cut hippocampal plane on the block face. Sections (10 μm) were then cut and stained with hematoxylin and eosin using routine methods. Sections were visualized using Olympus Vanox BH-2 microscope and analyzed by a board-certified pathologist (WTH) for evidence of inflammation and changes in microglia.

Immunocytochemistry and Quantitation of Microglia

Coronal sections (10 m) of the hippocampus were stained with anti-IbA1/AIF1 (1:500) (catalog NBP2-19019; Novus Biologicals, Centennial, CO) using standard methods and citrate antigen retrieval. HRP development was accomplished with the Vectastain ABC Staining Kit (Vector Laboratories, Burlingame, CA) using a secondary antibody provided. All sections were imaged on a Zeiss Axio Imager 2 microscope (Zeiss, Oberkochen, Germany) running Zen software (Zeiss), using the tiling and stitching feature to ensure the entire fascia dentata was visualized. Images were imported into NIS-Elements software (Nikon Co., Tokyo, Japan). One hemisphere was chosen and 600,000-700,000 μm² of the fascia dentata was demarcated as the region of interest (ROI). The number of microglia within this region was then counted. Microglia cells were defined as black/brown spots with two or greater associated tendrils and the number present in the ROI was counted. Microglial density was then calculated.

Behavioral Assays

Depressive symptoms were measured using the sucrose preference assay and the forced swim assay. These assays began 24 h after CP treatment and required 24-48 h to complete. No additional medications were given to the animals during this period. In the sucrose preference assay, animals were presented two bottles simultaneously, one containing a 2% sucrose solution and the other containing drinking water. The amount of liquid consumed in each bottle during the 24 h of testing was measured. The location of the two bottles was varied during this period. The sucrose preference score was expressed as percent of total liquid intake.

In the forced swim assay, rats were placed in tap water (25-27° C.) within a large, clear cylinder (Harvard Apparatus; Holliston, MA Cat #76-0494), such that the animal's legs nor their tail touched the bottom. Rats were left in this cylinder for a 10 min training period. 24 h later (48 h after CP), rats were then placed back in the cylinder and recorded for 5 min (Logitech Webcam; Silicon Valley, CA). The recordings were quantified for time spent immobile by several blinded individuals and the average score used in each individual measurement. Immobility was defined as absence of movement except for those necessary for keeping the nose above water.

Statistical Analysis

Statistical differences were assessed using a two-tail Students t-test or ANOVA followed by a Student-Newman-Keuls post-hoc analysis, as indicated in the figure legends.

All statistical analyses were conducted using Graph Pad In Stat Software (La Jolla, CA) and results were considered significant if $p<0.05$.

Example 11: CP Administration Increased Bladder Weight and Inflammation

Bladder weight and inflammation was used to confirm effective induction of cystitis. As shown in FIG. 13A, rat bladder weights were significantly increased 24 h after CP administration. Additionally, there was a significant increase in inflammation as indicated by extravasation of Evans blue (FIG. 13B). Both bladder weight and inflammation were reduced when CP-treated rats also received GLY, although the levels were still higher than vehicle-treated or GLY-only treated rats (FIG. 13A and FIG. 13B). As expected, concomitant treatment with Mesna blocked the changes in both endpoints to levels not significantly different from vehicle-treated controls (FIG. 13A and FIG. 13B).

Example 12: Caspase-1 Activity is Increased in the Hippocampus, but not in the Pons CNS tissue was harvested and processed as described in the Materials and Methods section. As shown in FIG. 14A, there was a significant increase in caspase-1 activity, a marker of inflammasome activation, in the hippocampus of CP-treated rats at 24 h. This increase was not present in the pons (FIG. 14B). This suggests that central activation of the inflammasome in response to CP-induced cystitis is occurring, at least in part, within the hippocampus and that this effect is specific and not a general response in the brain to CP or its metabolites.

Discussion

Chronic inflammatory syndromes are present in every specialty in medicine. Whether it is irritable bowel syndrome in gastroenterology or interstitial cystitis in urology, these conditions present a myriad of challenges to physicians and patients. These patients have high rates of co-morbid depression, anxiety and other related psychiatric disorders and recent studies have begun to demonstrate this adverse psychosocial consequence may be due to neuroinflammation mediated by the NLRP3 inflammasome (Miller et al. (2016) *Nature reviews Immunology* 16: 22-34). The present study has shown for the first time that an acute insult to the bladder in an animal model can also result in neuroinflammation in the CNS and the associated symptoms of depression.

The studies began by looking for signs of inflammasome activation (caspase-1 activity) in the hippocampus, due to its known association with depression, and the pons, due to its well-known function in micturition. An increase within the hippocampus 24 h after CP-treatment was found, but there were no significant changes in the pons. This differential response suggests the effect is specific to this region and not a non-specific, perhaps toxic, response of the brain to CP or its metabolites.

Example 13: Pro-IL-1β and Pro-IL-18 mRNA Expression are Increased in the Hippocampus Gene expression of pro-IL-1β and pro-IL-18 was measured in the hippocampus and pons. FIG. 15A demonstrates a significant increase in pro-IL-1β expression in the hippocampus of CP-treated rats while no change in expression was found within the pons (FIG. 15B). A significant increase of pro-IL-18 gene expression was also found in the hippocampus of CP-treated rats (FIG. 15C). Interestingly, there was also an increase in pro-IL-18 expression in the pons of CP-treated rats (FIG. 15D).

NLRP3, and other critical components of the inflammasome such as the associated speck-like protein containing a COOH-terminal caspase recruitment domain (ASC), have been found to be upregulated in many other inflammatory conditions, although their expression is regulated by mechanisms different than those regulating pro-IL-1β and pro-IL-18 (54). However, as shown in in FIG. 15E-FIG. 15H, no significant changes were observed in either NLRP3 or ASC in the hippocampus or pons of CP-treated rats.

Discussion

Often associated with inflammasome activation is an increase in expression of pro-IL-1β and/or pro-IL-18. Increased mRNA expression of both of these pro-inflammatory cytokines in the hippocampus was observed, consistent with inflammasome activation or at least the beginning of an inflammatory response. Surprisingly, pro-IL-18 was significantly increased in the pons suggesting this region of the brain is actually responding to CP. However, no other indication of an inflammatory reaction was observed.

Example 14: CP-Induced Cystitis Induces NLRP3-Dependent Inflammation in the Hippocampus Breakdown of the blood brain barrier is one of the known consequences of NLRP3-induced inflammation within the central nervous system (Song et al. (2017) *Front Cell Neurosci* 11: 63). In order to evaluate this change, the Evans blue assay was performed. In the hippocampus from CP-treated rats, a significant increase in Evans blue extravasation compared to vehicle-treated or GLY only-treated controls was detected, indicating inflammation and disruption of the blood brain barrier (FIG. 16A). Critically, the administration of either GLY or Mesna at the times indicated in FIG. 12 reduced the dye extravasation to levels not significantly different from controls. In the pons (FIG. 16B) there was no significant change in dye extravasation in response to CP, clearly demonstrating the effect in the hippocampus was specific and not a general breakdown of this barrier. When gross cross sections of the brain from CP-treated rats were examined (FIG. 16C), areas of Evans blue dye were apparent in the periventricular region of the hippocampal formation, where the dye was permeating through areas of true blood-brain barrier breakdown and not through the circumventricular organs. These blue areas were not observed in any other group (data not shown).

Histologically, the hippocampus demonstrated evidence of inflammation in the CP-treated rats (FIG. 16D). In particular, cells with morphology of activated microglia were present in the CP-treated samples (arrows in upper right and lower right panels). These inflammatory changes were found predominantly in and around the fascia dentata (indicated by brackets in the upper left panel). The activated microglia were not present when the CP-treated rats were administered GLY (CP+GLY group shown in lower left panel, all other groups—data not shown). To quantitate these changes, hippocampal sections were stained for IbA1/AIF1, a marker of activated microglia, and the density of activated microglia in the fascia dentata region quantitated. FIG. 16E shows a typical staining pattern for control, CP and CP+GLY samples (other groups not shown). FIG. 16F shows the results of this quantitation with a significantly increased density of microglia in the CP-treated rat. This increase was blocked to levels not significantly different from controls when rats were treated with either GLY or Mesna. Qualitatively, we also noted an increase in microglial processes in brains from CP-treated rats (arrows in FIG. 15E lower right panel).

Discussion

One of the most significant changes discovered was that CP-induced cystitis triggers breakdown of the blood-brain barrier within the hippocampus, but not the pons. The demarcation between the hippocampus and pons confirms that neither CP itself nor its metabolites are directly causing this breakdown. If direct effects were involved, the breakdown could be expected to occur throughout the CNS and not localize to the hippocampus. It should be noted that these experiments do not rule out inflammation and inflammasome activation in other parts of the brain. Importantly, glyburide prevented this blood brain barrier breakdown. Seeing as glyburide is an inhibitor of NLRP3 with little or no effects on other inflammasomes (Lamkanfi et al. (2009) *The Journal of cell biology* 187: 61-70), these results specifically implicate the NLRP3 inflammasome in this response. Finally, the breakdown of this barrier was also blocked with Mesna which is well-known to bind acrolein in the urine and prevent it from harming urothelia. Mesna undergoes rapid oxidation in plasma with only a very small portion remaining in circulation. Thus, urinary Mesna concentration vastly exceed that in plasma, essentially restricting this compound to the urinary system (Carless et al. (2008) *17th Expert Committee on the Selection and Use of Essential Medicines*; Jenkins (2014) London Cancer). Indeed, doses up to 100 mg/kg (compare to 40 mg/kg used in this study) have produced no apparent effects on bone marrow, hepatic, renal or CNS function (Id.). Thus, Mesna's effectiveness in this study strongly argues that the breakdown of the blood brain barrier in the hippocampus is a direct result of the cystitis triggered by CP in the bladder.

While Evan's blue does detect breakdown of the blood brain barrier it is also a harbinger of inflammation in a tissue. Indeed, histological evidence of inflammation was found in the CP-treated rats within the fascia dentata. Quantitation of the activated microglia in this region clearly showed an increased density and this increase was again blocked by both glyburide and Mesna. Thus, these results demonstrate that the NLRP3 inflammasome plays a critical role in inducing inflammation in the hippocampus in response to CP-induced cystitis. Therapeutically, administration of an NLRP3 inhibitor at the time of an acute inflammatory event, can serve as a critical intervention to prevent the emergence of neuroinflammatory changes.

At this time, the mechanism by which inflammation in the bladder results in inflammation in the hippocampus is unclear. Currently there are 3 distinct pathways that may contribute to varying degrees (Miller et al. (2016) *Nature reviews Immunology*). The first pathway, called the humoral pathway, includes the leaking of peripheral cytokines directly into the CNS through areas of blood brain barrier breakdown. Given serum pro-inflammatory cytokines (such as IL-1β, TNF-α, and IL-6) are increased in response to CP (Kim et al. (2015) *Biomol Ther* (Seoul) 23: 180-188), and given that barrier breakdown was detected as described herein, this pathway likely contributes to CP-induction of neuroinflammation. Peripheral cytokines may also be directly transported across the barrier through saturable transport molecules (Miller et al. (2016) *Nature reviews Immunology* 16: 22-34). The second pathway, the neural pathway, involves cytokine stimulation of afferent nerves that carry retrograde transmission of a signal for inflammation through ascending fibers and into the brain where they are translated back into central cytokine signals (Miller et al. (2009) *Biol Psychiatry* 65: 732-741). Recent evidence has established an inflammatory phenotype within the L6-S1 dorsal quadrants of the spinal cord in CP-cystitis (Liu et al. (2016) *Mol Pain* 12), suggesting that neural transfer of an inflammatory response may also be playing a role in moving the signal from the bladder to the CNS. Likewise, CP-cystitis is well known to cause bladder pain and acute pain itself can directly stimulate symptoms of depression (Michaelides et al. (2019) *Postgrad Med* 131: 438-444), most likely through this neural transfer pathway. Finally, a third pathway, called the cellular pathway, has been found to contribute to the transfer of inflammatory signals (D'Mello et al. (2009) *J Neurosci* 29: 2089-2102). This pathway involves movement of immune cells that have been activated in the periphery directly to the brain vasculature and parenchyma. This pathway was discovered in studies of the inflamed liver, which releases TNF-α. TNF-α crosses the blood brain barrier and stimulates the release of CC-chemokine ligand 2 (CCL2) from microglia which, in turn, passes back into the periphery and triggers the chemotaxis of monocytes into the brain (Id.). As stated earlier, there are increases in serum levels of TNF-α in response to CP (Kim et al (2015) *Biomol Ther* (Seoul) 23: 180-188), so it is possible this pathway is involved as well.

Example 15: CP-Induced Cystitis Results in NLRP3-Dependent Symptoms of Depression To determine if CP-induced cystitis results in depressive symptoms, two independent behavioral assays were performed, the sucrose preference assay and the forced swim assay. For these studies, an additional control group of CP-treated rats were administered the antidepressant fluoxetine to differentiate true depression symptoms from sick behavior, which would not be effected by the antidepressant. In the sucrose preference assay (FIG. 17A), CP-treated rats consumed a significantly lower percentage of sucrose-laden water. Importantly, this change was prevented when CP-treated rats were treated with GLY, Mesna or fluoxetine. In the forced swim assay (FIG. 17B), CP-treated rats spent significantly more time immobile when compared to control. Critically, this change was also prevented by GLY, Mesna and fluoxetine.

DISCUSSION

Regardless of how the peripheral inflammatory signal is transferred, once the brain is inflamed it is well known to bring about symptoms of depression and other negative psychosocial behaviors (Miller et al. (2009) *Biol Psychiatry* 65:732-741; Miller et al. (2016) *Nature reviews Immunology* 16:22-34; Noto et al. (2014) *Neuroimmunomodulation* 21:131-139; Sayana et al. (2017) *J Psychiatr Res* 92:160-182; Teixeira et al. (2014) *Neuroimmunomodulation* 21: 71). Indeed, using two distinct and well-established assays of depression, it was found that symptoms of depression strongly correlated with neuroinflammation in the present study. While these studies do not address how neuroinflammation actually brings about these symptoms, numerous theories abound in the literature (Miller et al. (2009) *Biol*

*Psychiatry* 65:732-741; Miller et al. (2016) *Nature reviews Immunology* 16:22-34) suggesting the mechanism may be multifactorial. For example, cytokines signals are known to influence the availability of mood-relevant neurotransmitters, particularly the monoamines (Miller (2009) *Brain Behav Immun* 23: 149-158). Many of these signals, working through well-known STAT, IRF, NF-κB and MAPK pathways (Fujigaki et al. (2006) *J Biochem* 139:655-662), activate indoleamine 2,3 dioxygenase (IDO) which shifts tryptophan metabolism toward kynurenine and away from serotonin, thus reducing serotonin availability (Dantzer et al. (2008) *Nat Rev Neurosci* 9:46-56; Schwarcz et al. (2002) *The Journal of pharmacology and experimental therapeutics* 303:1-10).

Kynurenine (converted to kynurenic acid in microglia) also inhibits release of glutamate and, by extension, dopamine (Borland et al. (2004) *J Neurochem* 91:220-229). Other work on potential pathways leading to depression demonstrate that cytokine signals may significantly affect neural plasticity, triggering decreased neurotrophic support, decreased neurogenesis, increased oxidative stress and even increased apoptosis in the CNS (Buntinx et al. (2004) *J Neurosci Res* 76:834-845; Goshen et al. (2007) *Psychoneuroendocrinology* 32:1106-1115; Koo et al. (2008) *Proceedings of the National Academy of Sciences of the United States of America* 105:751-756; Li et al. (2008) *J Neurosci* 28:5321-5330; McTigue et al. (2008) *J Neurochem* 107:1-19). Perhaps effects on neural plasticity may explain why, in some disorders of the genitourinary tract such as interstitial cystitis, debilitating psychiatric effects can persist long after any localized inflammation is measureable.

Finally, cytokines may have dramatic effects on the hypothalamic-pituitary-adrenal (TPA) axis (Goshen et al. (2008) *Mol Psychiatry* 13:717-728) and dysregulation of the HPA-axis has been suggested to underlie increased psychological stress levels in overactive bladder and interstitial cystitis patients, at least those exposed to chronic early life stress (Taylor (2010) *PNAS* 107: 8507-8512. The contributions off these various pathways to the mood disorders experienced by patients with diseases of the lower urinary tract represents important and exciting areas for exploration while offering the promise of targeted pharmacological interventions to alleviate the high morbidity and health-care costs associated with the mental suffering of urology patients.

In conclusion, this study has shown in an animal model that an acute insult in the bladder can trigger significant neuroinflammation in the hippocampus which brings about symptoms of depression. Moreover, the inflammation/depression responsive is dependent on activation of the NLRP3 inflammasome. Thus, this study proposes the first-ever causative explanation of the previously anecdotal link between benign bladder disorders and mood disorders.

Materials and Methods for Examples 16-19

Animals

Animal protocols were approved by the Institutional Animal Care and Use Committee at Duke University Medical Center and were performed in accordance with the guidelines set forth in the Guide for the Care and Use of Laboratory Animals published by the National Institutes of Health (USA). Sprague Dawley Rats (female, ≈50 days of age, ≈200 g) were purchased from Envigo (Indianapolis, IA) used in all experiments. Although in humans BOO occurs most frequently in males, the standard for BOO studies in rodents has long been the female rat. The primary reason is the tortuosity of the male urethra which can lead to physical damage, and consequently inflammation, during catheterization. Other concerns are complications arising from ducts associated with the prostatic gland and seminal vesicles. Thus, male animals are contraindicated in studies of BOO, particularly when examining inflammation and the results of inflammation.

For most studies rats were assigned to 4 groups; 1) Control, 2) Sham, 3) BOO or 4) BOO+ glyburide (Gly). An additional group (BOO+ fluoxetine) was used for behavior assays. For Sham and all BOO groups, animals were anesthetized [ketamine hydrochloride (90 mg/kg), xylazine (10 mg/kg); i.p.] and a 1 mm o.d. catheter (P50 tubing) inserted transurethrally. BOO was created by urethral ligation over a 1 mm catheter. A 5-0 silk suture was passed around the urethra and tied securely for BOO and loosely for Sham. The catheter was removed and the abdominal wall closed. For BOO+Gly, a subcutaneous pocket was made on the side of the neck and a single 50 mg, 21-day slow release pellet (Innovative Research of America, Sarasota, FL) inserted and the incision closed. A new pellet was placed (contralateral side) after 21 days. Sides were alternated thereafter. No signs of urinary tract infection were ever seen in any animal.

In the behavior assays, an additional group of BOO rats were provided with fluoxetine (Sigma, St Louis, MO) in the drinking water (0.50 mg/mL) for the last 4 weeks of the experiments. Twice weekly fluoxetine dose was adjusted to insure ≈20 mg/kg/day.

Evans Blue Assay

Rats were weighed and then injected (i.v. 3 ml/kg) with 2% Evan's blue dye in sterile saline by an investigator blinded to the groups (Belayev et al. (1996) *Brain Res* 739: 88-96). After one hour, rats were euthanized and transcardially perfused with cold PBS to remove intravascular dye. The brain was isolated and the hippocampus dissected, weighed and placed into formamide (0.25 ml) overnight (56° C.). Absorbance (620 nm) was measured and compared to a standard curve to calculate pg Evans blue/μg tissue.

Immunocytochemistry and Quantitation of Microglia and Neurogenesis

Brains were fixed (10% neutral buffered formalin; 48 h, rt) and grossly cut (coronally) to the hippocampus before being embedded in paraffin with the plane of the hippocampus on the block face. Citrate antigen retrieval was used prior to staining 10 μm coronal sections with anti-IbA1/AIF1 (1:500) (NBP2-19019; Novus Biologicals, Centennial, CO) or Anti-Ki67 (1:500) (ab15580; Abcam, Cambridge, MA) via standard methodology. IbA1 was visualized via HRP development (Vectastain ABC Kit; Vector, Burlingame, CA), biotinylated secondary antibody provided). Ki-67 was visualized using a goat anti-rabbit secondary antibody conjugated to Alexa Fluor 488 (111-545-144; Jackson ImmunoResearch Labs, West Grove, PA). All slides were coverslipped using Vectashield Antifade Mounting medium with DAPI (Vector, Burlingame, CA).

A Zeiss Axio Imager 2 microscope (Zeiss, Oberkochen, Germany) running Zen software (Zeiss) using the tiling and stitching feature was used to scan one entire hemisphere. Images were exported as TIFFs and imported into NIS-Elements software (Nikon Co., Tokyo, Japan) then calibrated. Slides were quantitated by a researcher blinded to the groups. For microglia, we demarcated 600,000-700,000 μm² of the fascia dentata, counted the number of black/brown spots with two or greater associated tendrils and calculated microglial density. For Ki-67⁺ cells we demarcated the entire dentate gyrus, CA1, CA2 and CA3 regions, quantitated nuclei (DAPI⁺) that were Ki-67⁺ (green florescence) and calculated the density.

Behavioral Assays

Open field—Rats are placed in an acrylic open-topped box (45 cm×45 cm×30 cm; L×W×H) and video recorded for 10 min. The bottom is white while the sides are clear. The floor was divided into 16 equal squares. After recording, the video is scored by individuals blinded to treatment and the amount of time in which two or more of the rats paws are inside the central 4 squares (time in middle) recorded.

Sucrose preference—rats are simultaneously provided with bottles containing 2% sucrose or drinking water. The location of the bottles are switched after 24 h. After 48 h the remaining liquid was measured and sucrose preference calculated as a percentage of the total liquid intake.

Statistical Analysis

Statistical assessments were conducted with Graph Pad In Stat Software (La Jolla, CA). ANOVA was used to examine differences across the four groups, followed by a Student-Newman-Keuls post-hoc analysis that enabled pairwise comparisons. To examine the effect of BOO on inflammation, bladder weight, neurogenesis and behavioral dysfunction in the hippocampus, we compared control (and sham) group to the untreated obstructed group. To examine whether treatment returned outcomes to baseline, neurogenesis and behavioral dysfunction, we compared control (and sham) group to the treated obstructed group. Lastly, to examine whether treatment ameliorated inflammation, we compared untreated and treated obstructed groups. Results were considered statistically significant if $p < 0.05$.

Example 16: BOO Increased Bladder Weight and this was Partially Blocked by Inhibiting NLRP3

Bladders from the various groups indicated in FIG. 18 were weighed when they were removed for the various endpoints in this experiment. As shown in FIG. 18, there was no difference in bladder weight in sham-operated rats compared to control. However, after 12 weeks of BOO bladder weights increased well over 10-fold. Glyburide suppresses this increase, although the values were considerably larger than controls.

Discussion

At 12 weeks of BOO, bladder weight increased even in the presence of glyburide, although the increase was attenuated in the drug-treated animals. The reason for the bladder weight gain in the glyburide-treated rats was not directly examined, but weight gain is composed of inflammation/edema and muscle hypertrophy and, while glyburide can be expected to blunt the inflammation/edema it is less likely to do so for muscle hypertrophy caused by overuse of the detrusor muscle.

Example 17: BOO Triggers NLRP3-Dependent Inflammation in the Hippocampus

To determine whether BOO triggers NLRP3-dependent inflammation in the hippocampus, BOO rats were treated with vehicle or glyburide and inflammation was assessed by the Evans blue assay as described in the Materials and Methods section. As shown in FIG. 19, BOO triggered a statistically significant increase in the leakage of Evan's blue into the hippocampus, indicating inflammation and disruption of the blood brain barrier. This leakage was reduced back to control levels by glyburide treatment. There was no difference between sham and control. To confirm this result, the density of microglia in the fascia dentate was quantitated. Activated microglia in 10 μm sections of brain were stained for IbA1/AIF1 and then visualized and quantitated as described in the Materials and Method section. FIG. 20 shows that there was no difference in the sham-operated groups but a statistically significant increase in the density of activated microglia in the hippocampus following 12 weeks of BOO. Again this difference was reduced back to control levels by glyburide.

Discussion

Critical to the hypothesis was the detection of inflammation in the hippocampus, initially ascertained using the Evans blue assay which measures the extravasation potential of the capillaries. When one considers the blood vessels traversing the brain, this assay also equates to a measurement of the integrity of the blood brain barrier (Belayev et al. (1996) Brain Res 739: 88-96). Thus, after 12 weeks BOO has precipitated a notable degradation of the blood brain barrier. The presence of inflammation suggested by the Evans blue assay was confirmed by the increase in activated microglia, the main drivers of neuroinflammation and the cells in the brain possessing NLRP3 (along with astrocytes).

Importantly, both the Evan's blue extravasation and the increase in microglia were blocked by glyburide, indicating their absolute dependence on NLRP3. While that fact is irrefutable, it is somewhat unclear where, exactly, the glyburide is functioning; at the level of the bladder, the brain or both. Undoubtedly, glyburide is acting in the bladder urothelia (Hughes et al. (2016) *J Urol* 195: 1598-1605; Hughes et al. (2019) Am J Physiol-Renal 316: F113-F120; Lutolf et al. (2018) *Neurourol Urodyn* 37: 952-959), as there are several publications showing just that. These urothelial effects also support the proposed inflammatory bladder-brain axis. Glyburide activity in the brain is not so clear. In the serum, glyburide is mostly albumin-bound and does not cross the blood brain barrier (Lahmann et al. (2015) LoS One 10: e0134476). However, in the event of a breakdown in the barrier, even transiently, glyburide can cross into the brain (Stokum et al. (2017) Behav Brain Res 333: 43-53) where it could function to block NLRP3 in microglia (and perhaps astrocytes), minimize neuroinflammation and preserve psychiatric health. Thus, the initial, major and perhaps only effect of glyburide is in the bladder but, if its protective effect is overwhelmed and there is breakdown of the blood brain barrier, it may enter the brain and directly prevent a neuroinflammatory response.

Example 18: BOO Causes a Decrease in the Number of Proliferating Cells in the Hippocampus To determine if BOO causes a decrease in the number of proliferating cells in the hippocampus, cells in 10 μm sections of brain were stained for Ki-67 and then visualized and quantitated as described in the Materials and Method section. As shown in FIG. 21, there was a statistically significant decrease in the concentration of proliferating cells (Ki-67$^+$) in the hippocampus following BOO. The decrease was blocked with concomitant administration of glyburide. There was no difference between sham and control.

Discussion

In the hippocampus BOO caused a statistically significant decrease in proliferating cells (Ki-67$^+$). Decreases in neurogenesis, and more generally plasticity, in the hippocampus have been directly linked with neuroinflammation and depression (Liu et al. (2017) *Neural Plast* 6871089), so given the neuroinflammation detected with the Evans blue and microglial activation assays, along with the signs of depression detected with the open field and sucrose preference assays, we feel the difference in Ki-67$^+$ cells likely reflect differences in neurogenesis. It is thought that these changes may lead to permanent, or at least long lasting, differences in cognitive function or mood that persists after the initiating stimulus is gone (in the case of BOO, after a TURP is performed). This decrease was also blocked by glyburide demonstrating the central role of NLRP3 and suggesting that NLRP3 inhibitors may further help prevent BOO-induced neurodeterioration by suppressing negative changes in neuroplasticity.

Example 19: BOO Rats Show NLRP-3 Dependent Signs of Depression; Anxiety and Anhedonia Two different behavior assays that assess different signs associated with depression were performed. The open field test measures anxiety as a function of the rat's propensity to explore the middle region of a square open field. Normal rats, being somewhat curious, will naturally explore this region while anxious rats refrain. The assay was performed as described in the Materials and Methods section and scored by a blinded investigator. As shown in FIG. 22A, BOO rats spent less than half the time of the control and sham rats exploring the middle of the field. Interestingly, glyburide restored this behavior demonstrating that this anxious behavior is NLRP3-dependent. In addition, a separate set of BOO rats were given the antidepressant fluoxetine. Fluoxetine helps to differentiate true depression-related behavior from sick behavior, which is not affected by this antidepressant. As shown in FIG. 22A, fluoxetine alleviated the depression and restored the exploratory behavior of these rats back to levels not statistically different from control.

Next, the sucrose preference assay that assesses anhedonia or the inability to feel pleasure was performed. The assay was performed as described in the Materials and Methods section. As shown in FIG. 22B there was a statistically significant decrease in the preference for sugar laden water in the BOO rats. Importantly, this preference was restored by treatment with glyburide. Fluoxetine also restored sucrose preference back to levels not statistically different from control. There was no difference between sham and control.

Discussion

Initial studies on the response of the innate immune system to BOO focused on the local response in the bladder (Hughes et al. (2016) *J Urol* 195: 1598-1605; Hughes et al. (2019) Am J Physiol-Renal 316: F113-F120; Lutolf et al. (2018) *Neurourol Urodyn* 37: 952-959). Those studies found that BOO activates the NLRP3 inflammasome in the urothelia to initiate inflammation, fibrosis and denervation. In this study we have greatly expanded that work to examine BOO-induced inflammation in the brain and changes it may make in behavior. Initially, hippocampal inflammation was found after 6 weeks but differences in sucrose preference at that time point were undetectable FIG. 23A and FIG. 23B, which necessitated performing this project after 12 weeks of obstruction. Thus, inflammatory differences likely preceded development of anhedonia and anxiety by several weeks suggesting, not surprisingly, a sequential series of events in which inflammation precedes behavioral alterations.

The most important observation in this study was the behavioral differences in the BOO rats. Untreated, obstructed animals showed statistically significant signs of anxiety and anhedonia, two core symptoms of depression, and these behavioral differences were blocked by glyburide demonstrating the centrality of this inflammasome in these mood changes. Importantly, the behavioral differences could also be prevented by the antidepressant fluoxetine demonstrating they are not due simply to pain or "sick" behavior as fluoxetine would not be expected to help in those situations.

One intriguing question that arises is the nature of the peripheral-to-central inflammatory signal. This is a hotly debated topic and currently three possible pathways are in vogue that are not mutually exclusive (Miller et al. (2016) Nat Rev Immunol 16: 22-34). The first pathway, the humoral pathway, could result from cytokines produced locally in the bladder travelling systemically via the vascular system, first to the blood brain barrier where they trigger breakdown, and subsequently into the CNS where they initiate microglial activation and neuroinflammation. Given the breakdown of the blood brain barrier in this study, this pathway is likely to contribute to BOO-induced neuroinflammation. Another possibility is the neural pathway where sensory input along afferent nerves carries a retrograde signal for inflammation back to the hippocampus where it is translates into cytokine production. Finally, a cellular pathway could involve transmigration of immune cells activated in the bladder directly across the blood brain barrier and into the brain vasculature and parenchyma. All three of these potential pathways warrant testing in future studies.

This study clearly shows that inflammatory injury to the bladder during BOO causes central inflammation and mood disorders. It implies, therefore, that relieving the obstruction will relieve the mood disorder. This work provides the first experimental animal data tying benign bladder dysfunction to mood disorders, and provides an exciting mechanism that might drive initiation and progression.

Any patents or publications mentioned in this specification are indicative of the levels of those skilled in the art to which the disclosure pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present disclosure is well adapted to carry out the objects and obtain the ends and advantages mentioned, as well as those inherent therein. The present disclosure is presently representative of embodiments, are exemplary, and are not intended as limitations on the scope of the invention. Changes therein and other uses will occur to those skilled in the art which are encompassed within the spirit of the disclosure as defined by the scope of the claims.

---

What is claimed is:

1. A method of treating inflammation in a bladder, the method comprising:

administering to a subject in need thereof a therapeutically effective amount of an NOD-like receptor family pyrin domain containing 3 (NLRP3) inflammasome inhibitor, whereby the inflammation is treated, wherein the NLRP3 inflammasome inhibitor is an Apoptosis-Associated Speck-like Protein C (ASC) inhibitor, NIMA-related kinase 7 (NEK7) inhibitor, Gasdermin D inhibitor, caspase-11 inhibitor, interleukin-1 β(IL-β) inhibitor, IL-18 inhibitor, or combinations thereof.

2. The method of claim 1, wherein the inflammation in the subject's bladder is an acute inflammation or a chronic inflammation.

3. The method of claim 1, wherein the inflammation in the subject's bladder is induced by a danger associated molecular pattern (DAMP) or a pathogen associated molecular pattern (PAMP).

4. The method of claim 3, wherein the PAMP is a fungus, bacteria, or virus.

5. The method of claim 1, wherein the subject is a human.

6. The method of claim 1, wherein the subject is diagnosed with diabetes, urinary tract infection, urinary frequency, fibrosis, bladder outlet obstruction, interstitial cystitis, cyclophosphamide (CP)-induced cystitis, depression, anxiety, neuroinflammation, a gynecologic cancer, kidney stones, a pelvic inflammatory disorder, endometriosis, Crohn's disease, diverticulitis, lupus, tuberculosis, and combinations thereof.

7. The method of claim 1, wherein the subject had been exposed to chemotherapy, radiation, a catheter, or a urinary stent.

8. The method of claim 1, the method further comprising repeating the administering of the therapeutically effective amount of the NLRP3 inflammasome inhibitor to the subject.

9. The method of claim 1, the method further comprising administering to the subject a therapeutically effective amount of an antidepressant agent.

10. The method of claim 9, wherein the antidepressant agent is selected from a selective serotonin reuptake inhibitor (SSRI), a norepinephrine-dopamine reuptake inhibitor (NDRI), a monoamine oxidase inhibitor (MAOI), or any combination thereof.

* * * * *